(12) United States Patent
Nakano et al.

(10) Patent No.: US 8,461,365 B2
(45) Date of Patent: Jun. 11, 2013

(54) METALLOCENE COMPLEX AND POLYMERIZATION METHOD OF OLEFIN

(75) Inventors: Masato Nakano, Yokkaichi (JP); Hideshi Uchino, Yokkaichi (JP); Naoshi Iwama, Yokkaichi (JP); Masami Kashimoto, Yokohama (JP); Tomohiro Kato, Yokohama (JP)

(73) Assignee: Japan Polypropylene Corporation, Tokyo (JP)

( * ) Notice: Subject to any disclaimer, the term of this patent is extended or adjusted under 35 U.S.C. 154(b) by 224 days.

(21) Appl. No.: 13/131,301

(22) PCT Filed: Dec. 14, 2009

(86) PCT No.: PCT/JP2009/070809
§ 371 (c)(1),
(2), (4) Date: May 26, 2011

(87) PCT Pub. No.: WO2010/071099
PCT Pub. Date: Jun. 24, 2010

(65) Prior Publication Data
US 2011/0230622 A1    Sep. 22, 2011

(30) Foreign Application Priority Data
Dec. 17, 2008    (JP) .................... 2008-320703

(51) Int. Cl.
*C08F 299/00*    (2006.01)
*C08F 4/76*    (2006.01)
*C07F 7/08*    (2006.01)
*B01J 31/14*    (2006.01)
*B01J 21/16*    (2006.01)

(52) U.S. Cl.
USPC .......... 556/11; 556/12; 556/53; 502/62; 502/103; 502/117; 502/152; 549/209; 525/245; 526/126; 526/127; 526/160; 526/943

(58) Field of Classification Search
USPC .......... 556/11, 12, 53; 502/62, 103, 117, 502/152; 549/209; 525/245; 526/126, 127, 526/160, 943
See application file for complete search history.

(56) References Cited

U.S. PATENT DOCUMENTS

| 6,995,279 B2 | 2/2006 | Ushioda et al. |
| 2004/0127731 A1 | 7/2004 | Ushioda et al. |
| 2005/0037919 A1* | 2/2005 | Burkhardt et al. ............ 502/117 |
| 2007/0155919 A1 | 7/2007 | Okumura et al. |

FOREIGN PATENT DOCUMENTS

| JP | 4 337308 | 11/1992 |
| JP | 6 287257 | 10/1994 |
| JP | 11 240909 | 9/1999 |
| JP | 2003 206325 | 7/2003 |
| JP | 2004 352707 | 12/2004 |
| JP | 2005 511751 | 4/2005 |
| JP | 2007 513906 | 5/2007 |

OTHER PUBLICATIONS

Extended European Search Report Issued Feb. 22, 2012, in European Patent Application No. 09833402.2.
Shin, Y. et al., "Synthesis and Characterization of Ethylene-Propylene Random Copolymers With Isotactic Propylene Sequence", Polymer, vol. 42, pp. 9611-9615, (2001).
International Search Report issued Jan. 19, 2010 in PCT/JP09/070809 filed Dec. 14, 2009.

* cited by examiner

*Primary Examiner* — Mark Kaucher
(74) *Attorney, Agent, or Firm* — Oblon, Spivak, McClelland, Maier & Neustadt, L.L.P.

(57) ABSTRACT

A metallocene complex by which high uptake efficiency of ethylene and/or α-olefin can be obtained compared with the conventional metallocene catalyst, and robber component having high molecular weight can be polymerized, and polymerization method of olefin. Metallocene complex (metallocene complex having furyl or thienyl group in which substituent exists at 5-position of indenyl ring, and substituent may exist at 2-position of indenyl ring, and the like) represented by the general formula [II], the catalyst for olefin polymerization characterized by comprising said metallocene complex, and polymerization method of olefin characterized that polymerization or copolymerization of olefin is carried out using said polymerization catalyst for olefin, and the like.

16 Claims, No Drawings

METALLOCENE COMPLEX AND POLYMERIZATION METHOD OF OLEFIN

TECHNICAL FIELD

The present invention relates to a metallocene complex and a polymerization method of olefin, and in more detail, to the metallocene complex, which have high uptake efficiency of ethylene and can produce copolymerized rubber component of ethylene-propylene having high molecular weight and is introduced the substituent into specified position, and the polymerization method of olefin.

BACKGROUND ART

Crystalline polypropylene has been widely used for various molding fields because of excellent mechanical property, chemical resistance and the like. However, propylene homo-polymer or random copolymer with small amount of α-olefin has high stiffness, but may be deficient in impact resistance.

Therefore, methods for adding rubber components such as ethylene-propylene copolymer (EPR) to propylene homo-polymer, or production of so-called impact copolymer containing rubber components by copolymerizing propylene and ethylene or α-olefin successively after homo-polymerization of propylene, has been employed for improvement of impact resistance. Further, by increase of rubber content of this impact copolymer, flexibility and impact resistance can be improved.

As another problems different from these points, in the impact copolymer obtained by polymerization in the presence of conventional Ziegler-Natta type catalyst, component of low molecular weight (oligomer component and the like) is present due to the nature of catalyst. In particular, recently, there is a tendency for further improving moldability of the obtained impact copolymer by increasing the flow property.

However, when flow property of rubber parts is enhanced too much, production ratio of low molecular weight component increases along with this, consequently, it has been known that this low molecular weight component becomes the causes of the various problems that generation of smoke, unusual malodor and the like are caused at molding, and even after molding, adverse effect is affected to odor or taste, and anti-blocking property is deteriorated by sticking, and the like. When powder properties of polymerized polymer are deteriorated, stable production cannot be achieved, therefore, this is a problem. On the other hand, when difference of average molecular weight of crystalline polypropylene and rubber parts becomes large, problems that evolution of gel increases at molding or linear expansion rate becomes high, are caused.

On the other hand, it has been known that isotactic polypropylene can be obtained by polymerizing propylene using metallocene type catalyst different from the conventional Ziegler-Natta type catalyst. In addition, it has been known that the impact copolymer can be produced by copolymerizing ethylene and propylene successively after homo-polymerization of propylene using similar catalyst (for example, refer to Patent Reference-1, 2). Further, the impact copolymer excellent in stiffness and impact resistance has been disclosed (for example, refer to Patent Reference-3).

In particular, in the impact copolymer, in order to exhibit high impact resistance, it is necessary to show, for example, lower glass transition temperature and in order to satisfy this, copolymerization of propylene and ethylene or α-olefin is preferred to be carried out so that each contents of these can satisfy some ranges (for example, refer to Non-Patent Reference-1).

And, many examples of transition metal compounds constituting the above-described metallocene type catalysts have already been known. Particularly, in order to improve the stiffness of the impact copolymer, also, transition metal compounds which provide the homo-polypropylene having high melting point have been known already (for example, refer to Patent Reference-4).

However, when these propylene type impact copolymers are produced by using metallocene type catalyst, the following technical problems have been occurred due to the reactivity difference of propylene and the other co-monomers.

That is, when copolymerization of propylene and ethylene or α-olefin is carried out by the conventional method using metallocene type catalyst after homo-polymerization of propylene, gas composition ratio of propylene/(ethylene or α-olefin) in polymerization atmosphere is greatly different from the polymerized amount ratio of amount of propylene/ (amount of ethylene or amount of α-olefin) polymerized in this atmosphere, and the case of decreasing the polymerized amount of (ethylene or α-olefin) in the polymer is occurred. That is, in order to obtain the copolymer having the desired content of ethylene or α-olefin, monomer gas having the greatly different monomers ratio from the contents of monomers in copolymer is needed to provide to polymerize, and it was the problem on the production. Further, in the extreme case, copolymer having the desired contents could not be produced due to restriction of the polymerization equipment.

Thus, in catalyst using metallocene complex, difference of ethylene content in ethylene/propylene mixed gas and ethylene content in the polymer becomes large, therefore, development of the production method having high uptake efficiency of ethylene and α-olefin for resolving these problems is needed.

In addition, the case of using the metallocene catalyst known until now has a problem that when copolymerization of propylene and ethylene or α-olefin is carried out in gas-phase, molecular weight of the resulting copolymer is low. In propylene-ethylene block copolymer, molecular weight of the copolymer is needed to keep more than a certain level to exhibit high impact resistance, and also, the production method by which the copolymer having high molecular weight can be produced is desired. In addition, in order to reduce the catalyst cost per unit polymer or to increase the content of rubber part, development of the catalyst having high rubber activity have been desired.

On the other hand, Patent Reference-5 describes the complex having a substituent at 5-position of indenyl ring, and discloses the metallocene complex by which propylene homo-polymer and copolymer having high melting point and high molecular weight can be provided.

However, this is the method having low uptake efficiency of ethylene, and it is not possible to recognize that polymerization performance such as melting point of resulting homo-polymer, and polymerization activity are satisfactory, further high-performance metallocene complex is desired to be created.

PRIOR ART DOCUMENTS

Patent Documents

PATENT DOCUMENT-1: JP-A-H4-337308;
PATENT DOCUMENT-2: JP-A-H6-287257;
PATENT DOCUMENT-3: JP-A-2003-206325;

PATENT DOCUMENT-4: JP-A-H11-240909;
PATENT DOCUMENT-5: JP-T-2005-511751;

Non-Patent Documents

NON-PATENT DOCUMENT-1: Polymer, 2001, vol. 42, p 9611.

SUMMARY OF INVENTION

Problem to be Solved by the Invention

In consideration of the above-described conventional technical problems, it is an object of the present invention to provide a metallocene complex which has the higher uptake efficiency of ethylene and α-olefin than one of the conventional metallocene catalyst, and by which the rubber components having high molecular weight can be polymerized, and polymerization method of olefin.

In addition, another object of the present invention is to provide the metallocene complex by which homo-polypropylene having high melting point can be obtained, and the copolymer can be with high activity obtained, and a polymerization method of olefin.

Means for Solving the Problem

In order to solve the above-described problems, as a result of intensive studies carried out by the present inventors, it has been found that by using the metallocene complex which has specified substituent, particularly, has substituent at 5-position of indenyl ring, and furyl group which may have substituent or thienyl group which may have substituent at 2-position of indenyl ring, uptake efficiency of ethylene and α-olefin improves, high molecular-weight rubber component can be obtained, and the present invention has been completed based on these knowledge.

That is, according to the first invention of the present invention, a metallocene complex represented by the following general formula [I] is provided.

[Formula 1]

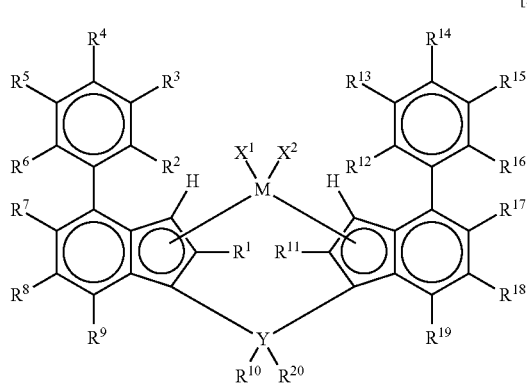

(wherein M is Ti, Zr or Hf, Y is carbon, silicon or germanium, $X^1$ and $X^2$ are each independently a ligand forming σ-bond with M. $R^1$ and $R^{11}$ may be each other same or different, and are hydrogen, alkyl group having 1 to 6 carbon number, alkoxy group having 1 to carbon number, furyl group, thienyl group, furyl group having substituent, or thienyl group having substituent. And one or both of $R^1$ and $R^{11}$ are necessarily any of furyl group, thienyl group, furyl group having substituent, or thienyl group having substituent. $R^7$ and $R^{17}$ may be each other same or different, and are hydrogen, halogen atom, alkyl group having 1 to 6 carbon number, alkoxy group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number or halogen-containing aryl group having 6 to 18 carbon number. Provided that, when any one of $R^7$ and $R^{17}$ is hydrogen, the other group is a substituent group except hydrogen. $R^2$, $R^3$, $R^4$, $R^5$, $R^6$, $R^8$, $R^9$, $R^{12}$, $R^{13}$, $R^{14}$, $R^{15}$, $R^{16}$, $R^{18}$ and $R^{19}$ may be same or different, and are hydrogen, halogen atom, alkyl group having 1 to 6 carbon number, alkoxy group having 1 to 6 carbon number, alkenyl group having 1 to 6 carbon number, halogen-containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen-containing aryl group having 6 to 18 carbon number, or heterocyclic group constituting 5-membered ring or 6-membered ring which may have substituent, in addition, 6 to 7-membered ring may be formed together with both of the adjacently located R and 6 to 7-membered ring may have unsaturated bond. $R^{10}$ and $R^{20}$ may be same or different, and are hydrogen, alkyl group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen-containing aryl group having 6 to 18 carbon number, or heterocyclic group forming 5-membered ring or 6-membered ring which may have substituent, 4 to 7-membered ring may be formed together with $R^{10}$ and $R^{20}$.)

According to the second invention of the present invention, there is provided the metallocene complex characterized in that, in the first invention, in the general formula [I], $R^1$ and $R^{11}$ may be each other same or different, and are hydrogen, alkyl group having 1 to 6 carbon number, alkoxy group having 1 to 6 carbon number, or the substituent represented by the formula [II], and one or both of $R^1$ and $R^{11}$ are necessarily substituent represented by the formula [II].

[Formula 2]

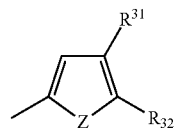

(wherein Z is oxygen atom or sulfur atom, $R^{31}$ and $R^{32}$ may be same or different, and are hydrogen, halogen atom, alkyl group having 1 to 6 carbon number, alkoxy group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number or halogen-containing aryl group having 6 to 18 carbon number. In addition, $R^{31}$ and $R^{32}$ may form 6-membered ring, and 6-membered ring may comprise unsaturated bond.)

According to the third invention of the present invention, there is provided the metallocene complex characterized in that, in the second invention, in the general formula [I], $R^1$ and $R^{11}$ may be each other same or different, and are the substituent represented by the formula [II].

In addition, according to the fourth invention of the present invention, there is provided the metallocene complex characterized in that, in the second invention, in the general formula [I], $R^7$ and $R^{17}$ may be each other same or different, and are the alkyl group having 1 to 6 carbon number.

Further, according to the fifth invention of the present invention there is provided the metallocene complex characterized in that, in the fourth invention, in the general formula [I], $R^7$ and $R^{17}$ are methyl groups.

According to the sixth invention of the present invention, there is provided the metallocene complex characterized in that, in fourth invention, in the general formula [I], $R^2$, $R^3$, $R^4$, $R^5$, $R^6$, $R^8$, $R^9$, $R^{12}$, $R^{13}$, $R^{14}$, $R^{15}$, $R^{16}$, $R^{18}$ and $R^{19}$ may be each other same or different, and are hydrogen, halogen atom, alkyl group having 1 to 6 carbon number, alkoxy group having 1 to 6 carbon number, aryl group having 6 to 18 carbon number, or halogen containing aryl group having 6 to 18 carbon number, in addition, 6 to 7-membered ring may be formed together with the adjacently located R, and 6 to 7-membered ring may comprise unsaturated bond.

In addition, according to the seventh invention of the present invention there is provided the metallocene complex characterized in that, in sixth invention, in the general formula [I], $R^8$, $R^9$, $R^{18}$ and $R^{19}$ are hydrogen.

In addition, according to the eighth invention of the present invention there is provided the metallocene complex characterized in that, in sixth invention, in the general formula [I], $R^2$, $R^8$, $R^9$, $R^{12}$, $R^{18}$ and $R^{19}$ are hydrogen.

According to the ninth invention of the present invention there is provided the catalyst for olefin polymerization characterized by comprising the metallocene complex relevant to any of the first to the eighth invention.

In addition, according to the tenth invention of the present invention there is provided the catalyst for olefin polymerization characterized by comprising the following (A), (B) and (C) components respectively, in the ninth invention.

component (A): the metallocene complex relevant to any of the first to the eighth invention;

component (B): a compound reacting with component (A) to form ionic pair, or a ion-exchanging layered silicate;

component (C): an organic aluminum compound.

Further, according to the eleventh invention of the present invention, there is provided the catalyst for olefin polymerization characterized in that component (B) is the ion-exchanging layered silicate, in the tenth invention.

Furthermore, according to the twelfth invention of the present invention there is provided the catalyst for olefin polymerization characterized in that prepolymerization treatment was carried out when producing the catalyst, in the ninth invention.

According to the thirteenth invention of the present invention there is provided the method for olefin polymerization characterized in carrying out olefin polymerization or copolymerization using the catalyst for olefin polymerization relevant to the ninth invention.

In addition, according to the fourteenth invention of the present invention there is provided the multi-step polymerization method of propylene type polymer characterized in that by using the catalyst for olefin polymerization relevant to ninth invention, the following steps are contained:

(i) a step of polymerizing 90 to 100% by weight of propylene, 10% by weight or less of ethylene and/or α-olefin having 4 or more carbon number relative to total monomer component; and (ii) a step of polymerizing 10 to 90% by weight of propylene, 10 to 90% by weight of ethylene and/or α-olefin having 4 or more carbon number relative to total monomer component.

Further, according to the fifteenth invention of the present invention there is provided a two-step polymerization method of propylene type polymer characterized in that, in the fourteenth invention, first step is:

(i) a bulk polymerization wherein propylene is used as solvent or gas-phase polymerization maintaining the monomers as gas phase in which 90 to 100% by weight of propylene, 10% by weight or less of ethylene and/or α-olefin having 4 or more carbon number relative to total monomer component; and the second step is:

(ii) a gas-phase polymerization in which 10 to 90% by weight of propylene, 10 to 90% by weight of ethylene and/or α-olefin having 4 or more carbon number relative to total monomer component are carried out.

Furthermore, according to the sixteenth invention of the present invention there is provided the two-step polymerization method of propylene type polymer characterized in that, in fifteenth invention, first step is:

(i) a step that only propylene is used as the total monomer component.

Effect of the Invention

By using the metallocene complex of the present invention as the polymerization catalyst, the uptake efficiency of ethylene or α-olefin is improved by comparison with the conventional metallocene complex, and rubber component having high molecular weight, particularly, component of ethylene/propylene copolymer can be obtained. In addition, propylene homo-polymer having high melting point can be obtained.

Therefore, propylene type polymer having excellent flexibility and impact resistance can be efficiently produced, thus, novel metallocene complex and method of olefin polymerization of the present invention are significantly useful in industrial viewpoint.

Modes for Carrying Out the Invention the production method of propylene type polymer using the metallocene complex of the present invention is described below with respect to each items in detail.

1. Metallocene Complex

The metallocene complex of the present invention is the metallocene complex having specified substituent represented by the general formula [1].

[Formula 3]

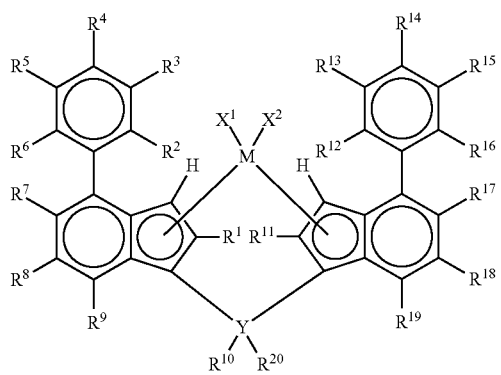

[I]

(wherein M is Ti, Zr or Hf, Y is a carbon, a silicon or a germanium, $X^1$ and $X^2$ are each independently a ligand forming σ-bond with M. $R^1$ and $R^{11}$ may be each other same or different, and are hydrogen, alkyl group having 1 to 6 carbon number, alkoxy group having 1 to 6 carbon number, furyl group, thienyl group, furyl group having substituent, or thienyl group having substituent. And one or both of $R^1$ and $R^{11}$ are necessarily any of furyl group, thienyl group, furyl group having substituent, or thienyl group having substituent. $R^7$ and $R^{17}$ may be each other same or different, and are hydrogen, halogen atom, alkyl group having 1 to 6 carbon number, alkoxy group having 1 to carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number or halogen-containing aryl group having 6 to 18 carbon number. Provided that, when any one of $R^7$ and $R^{17}$ is hydrogen, the other group is a substituent group except hydrogen. $R^2$, $R^3$, $R^4$, $R^5$, $R^6$, $R^8$, $R^9$, $R^{12}$, $R^{13}$, $R^{14}$, $R^{15}$, $R^{16}$, $R^{18}$ and $R^{19}$ may be same or different, and are hydrogen, halogen atom, alkyl group having 1 to 6 carbon number, alkoxy group having 1 to 6 carbon number, alkenyl group having 1 to 6 carbon number, halogen-containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen-containing aryl group having 6 to 18 carbon number, or heterocyclic group constituting 5-membered ring or 6-membered ring which may have substituent, in addition, 6 to 7-membered ring may be formed together with both of the adjacently located R, and 6 to 7-membered ring may have unsaturated bond. $R^{10}$ and $R^{20}$ may be same or different, and are hydrogen, alkyl group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen-containing aryl group having 6 to 18 carbon number, or heterocyclic group forming 5-membered ring or 6-membered ring which may have substituent, 4 to 7-membered ring may be formed together with $R^{10}$ and $R^{20}$.)

In the general formula [I], specific examples of alkyl group having 1 to 6 carbon number include methyl, ethyl, n-propyl, i-propyl, n-butyl, i-butyl, s-butyl, t-butyl, n-pentyl, n-hexyl, cyclopropyl, cyclopentyl, cyclohexyl and the like.

In addition, specific examples of alkoxy group having 1 to 6 carbon number include methoxy, ethoxy, n-propoxy, i-propoxy, n-butoxy, i-butoxy, tert-butoxy, phenoxy and the like.

In the general formula [I], specific examples of furyl group, thienyl group, furyl group having substituent, or thienyl group having substituent include 2-furyl, 2-(5-methylfuryl), 2-(5-ethylfuryl), 2-(5-n-propylfuryl), 2-(5-i-propylfuryl), 2-(5-t-butylfuryl), 2-(5-trimethylsilylfuryl), 2-(5-triethylsilylfuryl), 2-(5-phenylfuryl), 2-(5-tolylfuryl), 2-(5-fluorophenylfuryl), 2-(5-chlorophenylfuryl), 2-(4,5-dimethylfuryl), 2-(3,5-dimethylfuryl), 2-benzofuryl, 3-furyl, 3-(5-methylfuryl), 3-(5-ethylfuryl), 3-(5-n-propylfuryl), 3-(5-i-propylfuryl), 3-(5-t-butylfuryl), 3-(5-trimethylsilylfuryl), 3-(5-triethylsilylfuryl), 3-(5-phenylfuryl), 3-(5-tolylfuryl), 3-(5-fluorophenylfuryl), 3-(5-chlorophenylfuryl), 3-(4,5-dimethylfuryl), 3-benzofuryl, 2-thienyl, 2-(5-methylthienyl), 2-(5-ethylthienyl), 2-(5-n-propylthienyl), 2-(5-i-propylthienyl), 2-(5-t-butylthienyl), 2-(5-trimethylsilylthienyl), 2-(5-triethylsilylthienyl), 2-(5-phenylthienyl), 2-(5-tolylthienyl), 2-(5-fluorophenylthienyl), 2-(5-chlorophenylthienyl), 2-(4,5-dimethylthienyl), 2-(3,5-dimethylthienyl), 2-benzothienyl, 3-thienyl, 3-(5-methylthienyl), 3-(5-ethylthienyl), 3-(5-n-propylthienyl), 3-(5-i-propylthienyl), 3-(5-t-butylthienyl), 3-(5-trimethylsilylthienyl), 3-(5-triethylsilylthienyl), 3-(5-phenylthienyl), 3-(5-tolylthienyl), 3-(5-fluorophenylthienyl), 3-(5-chlorophenylthienyl), 3-(4,5-dimethylthienyl), 3-benzothienyl and the like.

In the general formula [I], halogen atoms include chlorine, bromine, iodine, fluorine, in addition, specific examples of alkenyl group having 1 to 6 carbon number include vinyl, propenyl, allyl, butenyl, cyclohexenyl and the like.

In addition, halogen atoms in the halogen containing alkyl group having 1 to 6 carbon number include fluorine atom, chlorine atom, bromine atom, iodine atom, and halogen containing alkyl group having 1 to 6 carbon number is one in which halogen atom is substituted for hydrogen on the skeleton in alkyl group having 1 to 6 carbon number. Specific examples can include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, 5-chloropentyl, 5,5,5-trichloropentyl, 5-fluoropentyl, 5,5,5-trifluoropentyl, 6-chlorohexyl, 6,6,6-trichlorohexyl, 6-fluorohexyl, 6,6,6-trifluorohexyl.

In the general formula [I], trialkylsilyl group containing alkyl group having 1 to 6 carbon number is one in which trialkylsilyl group which is substituted with alkyl group having 1 to 3 carbon number on silicon is substituted for alkyl group having 1 to 6 carbon number, specific examples include trimethylsilylmethyl, trimethylsilylethyl.

silyl group containing hydrocarbon group having 1 to 6 carbon number containing is the group in which 3 hydrocarbon groups having 1 to 6 carbon number, which may be different, are substituted on silicon, hydrocarbon group having 1 to 6 carbon number include alkyl group having 1 to 6 carbon number in the general formula [I], alkoxy group having 1 to 6 carbon number, alkenyl group having 1 to 6 carbon number, halogen containing alkyl group having 1 to 6 carbon number and phenyl group, and substituent may be contained on phenyl group. Specific examples include trimethylsilyl, triethylsilyl, tri-n-butylsilyl, t-butyldimethylsilyl, trivinylsilyl, triallylsilyl, triphenylsilyl.

In the general formula [I], aryl group having 6 to 18 carbon number may be substituted with hydrocarbon group having 1 to 6 carbon number, specific examples include phenyl, tolyl, dimethylphenyl, ethylphenyl, trimethylphenyl, t-butylphenyl, biphenyl, 1-naphthyl, 2-naphthyl, acenaphthyl, phenanthryl, anthryl and the like.

In addition, specific examples of halogen containing aryl group having 6 to 18 carbon number is one obtained by substituting hydrogen atom of the aryl group having 6 to 18 carbon number with halogen, specifically, 2-,3-,4-substituted each fluorophenyl, 2-,3-,4-substituted each chlorophenyl, 2-,3-,4-substituted each bromophenyl, 2,4-, 2,5-, 2,6-, 3,5-substituted each difluorophenyl, 2,4-, 2,5-, 2,6-, 3,5-substituted each dichlorophenyl, 2,4,6-, 2,3,4-, 2,4,5-, 3,4,5-substituted each trifluorophenyl, 2,4,6-, 2,3,4-, 2,4,5-, 3,4,5-substituted each trichlorophenyl, pentafluorophenyl, pentachlorophenyl, 3,5-dimethyl-4-chlorophenyl, 3,5-dichloro-4-biphenyl and the like.

In the general formula [I], heterocyclic group constituting 5-membered ring or 6-membered ring which may have substituent is one which does not directly bond to alkadienyl group at hetero atom, specific examples of heterocyclic groups include pyrrolidyl, pyridyl, pyrimidyl, quinolyl, isoquinolyl, carbazolyl, furyl, thienyl, thianofuryl, imidazolyl, pyrazolyl, pyrrolyl, oxazolyl, thiazolyl, isothiazolyl, isooxazolyl, and these heterocyclic groups may have substituents of alkyl group having 1 to 6 carbon number, alkenyl group having 1 to 6 carbon number, halogen containing alkyl group having 1 to 6 carbon number, silyl group containing hydrocarbon group having 1 to 6 carbon number, aryl group having 6 to 18 carbon number or halogen containing aryl group having 6 to 18 carbon number, and may form 5 to 7-membered ring together with the adjacently located atoms, and may contain unsaturated bond in this ring, and 5 to 7-membered ring may have hetero atom. These groups include the furyl group, thienyl group, furyl group having substituent, or thienyl group having substituent.

In the general formula [I], M is Ti, Zr or Hf, preferably Zr, Hf, particularly preferably Zr. Y is a carbon, a silicon or a germanium, preferably a silicon, a germanium. In addition, substituents $R^{10}$ and $R^{20}$ on Y may constitute 4 to 7-membered ring, and specific examples include silacyclobutane, silacyclopentane, 2,5-dimethylsilacyclopentane, silacyclohexane, silafluorene.

$X^1$ and $X^2$ are each independently a ligand forming σ-bonding with M, and is not particularly limited, preferable $X^1$ and $X^2$ include halogen atom, hydrocarbon group having 1 to 20 carbon number, substituted amino group having 1 to 20 carbon number, nitrogen containing hydrocarbon group having 1 to 20 carbon number, and halogen containing hydrocarbon group having 1 to 20 carbon number and the like. $X^1$ and $X^2$ may form cross-linked structure. Specifically, chlorine atom, bromine atom, iodine atom, fluorine atom, methyl group, ethyl group, propyl group, n-butyl group, i-butyl group, phenyl group, benzyl group, dimethylamino group or diethylamino group and the like, are included.

Among them, halogen atom, hydrocarbon group having 1 to 7 carbon number are preferable, specifically, chlorine atom, methyl group, i-butyl group, phenyl group or benzyl group is particularly preferable.

$R^2$, $R^3$, $R^4$, $R^5$, $R^6$, $R^8$, $R^9$, $R^{12}$, $R^{13}$, $R^{14}$, $R^{15}$, $R^{16}$, $R^{18}$ and $R^{19}$ may form 6 to 7-membered ring together with the adjacently located R, and 6 to 7-membered ring may contain unsaturated bond. Specifically, substituents at 4-position of indenyl ring include 1-naphthyl, 2-naphthyl, 5,6,7,8-tetrahydro-1-naphthyl, 5,6,7,8-tetrahydro-2-naphthyl, phenanthryl, anthryl and the like.

Substituents of $R^1$ and $R^{11}$ are preferably alkyl group having 1 to 6 carbon number, furyl group or thienyl group which may contain substituent, and in alkyl group having 1 to 6 carbon number, methyl, ethyl, n-propyl, n-butyl, i-propyl, i-butyl are preferable, and methyl group is particularly preferable. In addition, as substituent of $R^1$ and $R^{11}$, furyl group, thienyl group, furyl group having substituent, or thienyl group having substituent can be particularly preferably represented by the following formula [II].

[Formula 4]

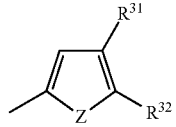

[II]

(wherein Z is oxygen atom or sulfur atom, $R^{31}$ and $R^{32}$ may be same or different, and are hydrogen, halogen atom, alkyl group having 1 to 6 carbon number, alkoxy group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number or halogen-containing aryl group having 6 to 18 carbon number. In addition, $R^{31}$ and $R^{32}$ may form 6-membered ring, and 6-membered ring may comprise unsaturated bond.)

The meaning of substituent in the general formula [II] is the same as one in the general formula [I], and substituents of $R^{31}$, $R^{32}$ are preferably halogen atom, alkyl group having 1 to 6 carbon number, aryl group having 6 to 18 carbon number, preferably alkyl group having 1 to 6 carbon number, aryl group having 6 to 18 carbon number.

$R^1$ and $R^{11}$ are preferably furyl group, thienyl group, furyl group having substituent or thienyl group having substituent, more preferably furyl group having substituent or thienyl group having substituent in view of high uptake efficiency of ethylene, further preferably furyl group having substituent.

It should be noted that, when metallocene complex is synthesized, generally isomers such as racemic form or meso form are generated by approximately 1:1. Usually, as a polymerization catalyst for propylene, racemic form is used, therefore, racemic form is needed to separate from mixture of racemic form/meso form.

However, in metallocene complex relevant to the present invention, one in which substituents ($R^1$ and $R^{11}$) at 2-position of indenyl ring are simultaneously substituted to furyl group, thienyl group, furyl group having substituent or thienyl group having substituent together, forms a racemic form by 80% or more of selectivity in complexation, and separation is easily carried out, therefore, racemic form can be obtained by high yield, thus such structure is useful for synthesis.

Ethylene/propylene copolymer having high molecular weight can be obtained when any one of $R^7$ and $R^{17}$ is substituent except hydrogen, preferably when both of $R^7$ and $R^{17}$ are substituent except hydrogen, ethylene/propylene copolymer having higher molecular weight can be obtained.

Preferable substituents of $R^7$ and $R^{17}$ are halogen atom, alkyl group having 1 to 6 carbon number, alkenyl group having 1 to 6 carbon number, halogen containing alkyl group having 1 to 6 carbon number, aryl group having 6 to 18 carbon number, halogen containing aryl group having 6 to 18 carbon number, particularly preferably halogen atom, alkyl group having 1 to 6 carbon number, further preferably alkyl group having 1 to 6 carbon number, furthermore preferably methyl group.

In view of high rubber activity, $R^2$, $R^8$, $R^9$, $R^{12}$, $R^{18}$ and $R^{19}$ are preferably simultaneously hydrogen, further preferably, $R^2$, $R^6$, $R^8$, $R^9$, $R^{12}$, $R^{16}$, $R^{18}$ and $R^{19}$ are simultaneously hydrogen.

In addition, as substituents ($R^2$, $R^3$, $R^4$, $R^5$, $R^6$, $R^{12}$, $R^{13}$, $R^{14}$, $R^{15}$, $R^{16}$) on phenyl group at 4-position of indenyl ring, any one or more of $R^3$, $R^4$, $R^5$, $R^{13}$, $R^{14}$, $R^{15}$ preferably have substituent, further preferably, any one or more of $R^3$, $R^4$, $R^5$ and any one or more of $R^{13}$, $R^{14}$, $R^{15}$ have substituent. More preferably, $R^3$, $R^5$, $R^{13}$, $R^{15}$ have substituent simultaneously.

Preferable substituents are halogen atom, alkyl group having 1 to 6 carbon number, alkoxy group having 1 to 6 carbon number, halogen containing alkyl group having 1 to 6 carbon number, silyl group containing hydrocarbon group having 1 to 6 carbon number, aryl group having 6 to 18 carbon number, halogen containing aryl group having 6 to 18 carbon number.

In addition, in view of high rubber activity, $R^4$, $R^{14}$ preferably have substituent, preferable substituents are halogen atom, alkyl group having 1 to carbon number, alkoxy group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen containing aryl group having 6 to 18 carbon number, more preferably alkyl group having 1 to 6 carbon number, halogen containing alkyl group having 1 to 6 carbon number, silyl group containing hydrocarbon group having 1 to 6 carbon number, aryl group having 6 to 18 carbon number.

Specific Examples of Metallocene Complex:

Specific examples of metallocene complex of the present invention are shown below:

dimethylsilylenebis(2-(2-(5-methylfuryl))-4-phenyl-5-methylindenyl)zirconium dichloride;
dimethylsilylenebis(2-(2-(5-methylfuryl))-4-(2-methylphenyl)-5-methylindenyl)zirconium dichloride;
dimethylsilylenebis(2-(2-(5-methylfuryl))-4-(2-ethylphenyl)-5-methylindenyl)zirconium dichloride;
dimethylsilylenebis(2-(2-(5-methylfuryl))-4-(2-methoxyphenyl)-5-methylindenyl)zirconium dichloride;
dimethylsilylenebis(2-(2-(5-methylfuryl))-4-(2-chlorophenyl)-5-methylindenyl)zirconium dichloride;
dimethylsilylenebis(2-(2-(5-methylfuryl))-4-(2-biphenyl)-5-methylindenyl)zirconium dichloride;
dimethylsilylenebis(2-(2-(5-methylfuryl))-4-(3-methylphenyl)-5-methylindenyl)zirconium dichloride;
dimethylsilylenebis(2-(2-(5-methylfuryl))-4-(3-ethylphenyl)-5-methylindenyl)zirconium dichloride;
dimethylsilylenebis(2-(2-(5-methylfuryl))-4-(3-methoxyphenyl)-5-methylindenyl)zirconium dichloride;
dimethylsilylenebis(2-(2-(5-methylfuryl))-4-(3-chlorophenyl)-5-methylindenyl)zirconium dichloride;
dimethylsilylenebis(2-(2-(5-methylfuryl))-4-(3-biphenyl)-5-methylindenyl)zirconium dichloride;
dimethylsilylenebis(2-(2-(5-methylfuryl))-4-(4-methylphenyl)-5-methylindenyl)zirconium dichloride;
dimethylsilylenebis(2-(2-(5-methylfuryl))-4-(4-ethylphenyl)-5-methylindenyl)zirconium dichloride;
dimethylsilylenebis(2-(2-(5-methylfuryl))-4-(4-i-propylphenyl)-5-methylindenyl)zirconium dichloride;
dimethylsilylenebis(2-(2-(5-methylfuryl))-4-(4-t-butylphenyl)-5-methylindenyl)zirconium dichloride;
dimethylsilylenebis(2-(2-(5-methylfuryl))-4-(4-biphenyl)-5-methylindenyl)zirconium dichloride;
dimethylsilylenebis(2-(2-(5-methylfuryl))-4-(4-methoxyphenyl)-5-methylindenyl)zirconium dichloride;
dimethylsilylenebis(2-(2-(5-methylfuryl))-4-(4-trifluoromethylphenyl)-5-methylindenyl)zirconium dichloride;
dimethylsilylenebis(2-(2-(5-methylfuryl))-4-(4-trimethylsilylphenyl)-5-methylindenyl)zirconium dichloride;
dimethylsilylenebis(2-(2-(5-methylfuryl))-4-(3,5-dimethylphenyl)-5-methylindenyl)zirconium dichloride;
dimethylsilylenebis(2-(2-(5-methylfuryl))-4-(3,5-diethylphenyl)-5-methylindenyl)zirconium dichloride;
dimethylsilylenebis(2-(2-(5-methylfuryl))-4-(3,5-di-1-propylphenyl)-5-methylindenyl)zirconium dichloride;
dimethylsilylenebis(2-(2-(5-methylfuryl))-4-(3,5-di-t-butylphenyl)-5-methylindenyl)zirconium dichloride;
dimethylsilylenebis(2-(2-(5-methylfuryl))-4-(3,5-di-methoxyphenyl)-5-methylindenyl)zirconium dichloride;
dimethylsilylenebis(2-(2-(5-methylfuryl))-4-(3,5-di-trimethylsilylphenyl)-5-methylindenyl)zirconium dichloride;
dimethylsilylenebis(2-(2-(5-methylfuryl))-4-(3,5-di-trifluoromethylphenyl)-5-methylindenyl)zirconium dichloride,
dimethylsilylenebis(2-(2-(5-methylfuryl))-4-(3,4,5-trimethylphenyl)-5-methylindenyl)zirconium dichloride;
dimethylsilylenebis(2-(2-(5-methylfuryl))-4-(3,5-dimethyl-4-trimethylsilylphenyl)-5-methylindenyl)zirconium dichloride;
dimethylsilylenebis(2-(2-(5-methylfuryl))-4-(3,5-dimethyl-4-biphenyl)-5-methylindenyl)zirconium dichloride,
dimethylsilylenebis(2-(2-(5-methylfuryl))-4-(3,5-dimethyl-4-methoxyphenyl)-5-methylindenyl)zirconium dichloride;
dimethylsilylenebis(2-(2-(5-methylfuryl))-4-(3,5-dichloro-4-trimethylsilylphenyl)-5-methylindenyl)zirconium dichloride;
dimethylsilylenebis(2-(2-(5-methylfuryl))-4-(3,5-dichloro-4-biphenyl)-5-methylindenyl)zirconium dichloride;
dimethylsilylenebis(2-(2-(5-methylfuryl))-4-(3,5-dichloro-4-methoxyphenyl)-5-methylindenyl)zirconium dichloride,
dimethylsilylenebis(2-(2-(5-methylfuryl))-4-(1-naphthyl)-5-methylindenyl)zirconium dichloride;
dimethylsilylenebis(2-(2-(5-methylfuryl))-4-(2-naphthyl)-5-methylindenyl)zirconium dichloride;
dimethylsilylenebis(2-(2-(5-methylfuryl))-4-(9-phenanthryl)-5-methylindenyl)zirconium dichloride;
dimethylsilylenebis(2-(2-(5-methylfuryl))-4-(2-phenanthryl)-5-methylindenyl)zirconium dichloride;
dimethylsilylenebis(2-(2-(5-methylfuryl))-4-phenyl-5-ethylindenyl)zirconium dichloride;
dimethylsilylenebis(2-(2-(5-methylfuryl))-4-(2-methylphenyl)-5-ethylindenyl)zirconium dichloride;
dimethylsilylenebis(2-(2-(5-methylfuryl))-4-(2-ethylphenyl)-5-ethylindenyl)zirconium dichloride;
dimethylsilylenebis(2-(2-(5-methylfuryl))-4-(2-methoxyphenyl)-5-ethylindenyl)zirconium dichloride;
dimethylsilylenebis(2-(2-(5-methylfuryl))-4-(2-chlorophenyl)-5-ethylindenyl)zirconium dichloride;
dimethylsilylenebis(2-(2-(5-methylfuryl))-4-(2-biphenyl)-5-ethylindenyl)zirconium dichloride;
dimethylsilylenebis(2-(2-(5-methylfuryl))-4-(3-methylphenyl)-5-ethylindenyl)zirconium dichloride;
dimethylsilylenebis(2-(2-(5-methylfuryl))-4-(3-ethylphenyl)-5-ethylindenyl)zirconium dichloride;
dimethylsilylenebis(2-(2-(5-methylfuryl))-4-(3-methoxyphenyl)-5-ethylindenyl)zirconium dichloride;
dimethylsilylenebis(2-(2-(5-methylfuryl))-4-(3-chlorophenyl)-5-ethylindenyl)zirconium dichloride;

dimethylsilylenebis(2-(2-(5-methylfuryl))-4-(3-biphenyl)-5-ethylindenyl)zirconium dichloride;
dimethylsilylenebis(2-(2-(5-methylfuryl))-4-(4-methylphenyl)-5-ethylindenyl)zirconium dichloride;
dimethylsilylenebis(2-(2-(5-methylfuryl))-4-(4-ethylphenyl)-5-ethylindenyl)zirconium dichloride;
dimethylsilylenebis(2-(2-(5-methylfuryl))-4-(4-i-propylphenyl)-5-ethylindenyl)zirconium dichloride;
dimethylsilylenebis(2-(2-(5-methylfuryl))-4-(4-t-butylphenyl)-5-ethylindenyl)zirconium dichloride;
dimethylsilylenebis(2-(2-(5-methylfuryl))-4-(4-biphenyl)-5-ethylindenyl)zirconium dichloride;
dimethylsilylenebis(2-(2-(5-methylfuryl))-4-(4-methoxyphenyl)-5-ethylindenyl)zirconium dichloride;
dimethylsilylenebis(2-(2-(5-methylfuryl))-4-(4-trifluoromethylphenyl)-5-ethylindenyl)zirconium dichloride;
dimethylsilylenebis(2-(2-(5-methylfuryl))-4-(4-trimethylsilylphenyl)-5-ethylindenyl)zirconium dichloride;
dimethylsilylenebis(2-(2-(5-methylfuryl))-4-(3,5-dimethylphenyl)-5-ethylindenyl)zirconium dichloride;
dimethylsilylenebis(2-(2-(5-methylfuryl))-4-(3,5-diethylphenyl)-5-ethylindenyl)zirconium dichloride;
dimethylsilylenebis(2-(2-(5-methylfuryl))-4-(3,5-di-1-propylphenyl)-5-ethylindenyl)zirconium dichloride;
dimethylsilylenebis(2-(2-(5-methylfuryl))-4-(3,5-di-t-butylphenyl)-5-ethylindenyl)zirconium dichloride;
dimethylsilylenebis(2-(2-(5-methylfuryl))-4-(3,5-di-methoxyphenyl)-5-ethylindenyl)zirconium dichloride;
dimethylsilylenebis(2-(2-(5-methylfuryl))-4-(3,5-di-trimethylsilylphenyl)-5-ethylindenyl)zirconium dichloride;
dimethylsilylenebis(2-(2-(5-methylfuryl))-4-(3,5-di-trifluoromethylphenyl)-5-ethylindenyl)zirconium dichloride;
dimethylsilylenebis(2-(2-(5-methylfuryl))-4-(3,4,5-trimethylphenyl)-5-ethylindenyl)zirconium dichloride,
dimethylsilylenebis(2-(2-(5-methylfuryl))-4-(3,5-dimethyl-4-trimethylsilylphenyl)-5-ethylindenyl)zirconium dichloride;
dimethylsilylenebis(2-(2-(5-methylfuryl))-4-(3,5-dimethyl-4-biphenyl)-5-ethylindenyl)zirconium dichloride;
dimethylsilylenebis(2-(2-(5-methylfuryl))-4-(3,5-dimethyl-4-methoxyphenyl)-5-ethylindenyl)zirconium dichloride;
dimethylsilylenebis(2-(2-(5-methylfuryl))-4-(3,5-dichloro-4-trimethylsilylphenyl)-5-ethylindenyl)zirconium dichloride;
dimethylsilylenebis(2-(2-(5-methylfuryl))-4-(3,5-dichloro-4-biphenyl)-5-ethylindenyl)zirconium dichloride;
dimethylsilylenebis(2-(2-(5-methylfuryl))-4-(3,5-dichloro-4-methoxyphenyl)-5-ethylindenyl)zirconium dichloride;
dimethylsilylenebis(2-(2-(5-methylfuryl))-4-(1-naphthyl)-5-ethylindenyl)zirconium dichloride;
dimethylsilylenebis(2-(2-(5-methylfuryl))-4-(2-naphthyl)-5-ethylindenyl)zirconium dichloride;
dimethylsilylenebis(2-(2-(5-methylfuryl))-4-(9-phenanthryl)-5-ethylindenyl)zirconium dichloride;
dimethylsilylenebis(2-(2-(5-methylfuryl))-4-(2-phenanthryl)-5-ethylindenyl)zirconium dichloride;
dimethylsilylenebis(2-(2-(4,5-dimethylfuryl))-4-phenyl-5-methylindenyl)zirconium dichloride;
dimethylsilylenebis(2-(2-(4,5-dimethylfuryl))-4-(2-methylphenyl)-5-methylindenyl)zirconium dichloride;
dimethylsilylenebis(2-(2-(4,5-dimethylfuryl))-4-(2-ethylphenyl)-5-methylindenyl)zirconium dichloride;
dimethylsilylenebis(2-(2-(4,5-dimethylfuryl))-4-(2-methoxyphenyl)-5-methylindenyl)zirconium dichloride;
dimethylsilylenebis(2-(2-(4,5-dimethylfuryl))-4-(2-chlorophenyl)-5-methylindenyl)zirconium dichloride;
dimethylsilylenebis(2-(2-(4,5-dimethylfuryl))-4-(2-biphenyl)-5-methylindenyl)zirconium dichloride;
dimethylsilylenebis(2-(2-(4,5-dimethylfuryl))-4-(3-methylphenyl)-5-methylindenyl)zirconium dichloride;
dimethylsilylenebis(2-(2-(4,5-dimethylfuryl))-4-(3-ethylphenyl)-5-methylindenyl)zirconium dichloride;
dimethylsilylenebis(2-(2-(4,5-dimethylfuryl))-4-(3-methoxyphenyl)-5-methylindenyl)zirconium dichloride;
dimethylsilylenebis(2-(2-(4,5-dimethylfuryl))-4-(3-chlorophenyl)-5-methylindenyl)zirconium dichloride;
dimethylsilylenebis(2-(2-(4,5-dimethylfuryl))-4-(3-biphenyl)-5-methylindenyl)zirconium dichloride;
dimethylsilylenebis(2-(2-(4,5-dimethylfuryl))-4-(4-methylphenyl)-5-methylindenyl)zirconium dichloride;
dimethylsilylenebis(2-(2-(4,5-dimethylfuryl))-4-(4-ethylphenyl)-5-methylindenyl)zirconium dichloride;
dimethylsilylenebis(2-(2-(4,5-dimethylfuryl))-4-(4-i-propylphenyl)-5-methylindenyl)zirconium dichloride;
dimethylsilylenebis(2-(2-(4,5-dimethylfuryl))-4-(4-t-butylphenyl)-5-methylindenyl)zirconium dichloride;
dimethylsilylenebis(2-(2-(4,5-dimethylfuryl))-4-(4-biphenyl)-5-methylindenyl)zirconium dichloride;
dimethylsilylenebis(2-(2-(4,5-dimethylfuryl))-4-(4-methoxyphenyl)-5-methylindenyl)zirconium dichloride;
dimethylsilylenebis(2-(2-(4,5-dimethylfuryl))-4-(4-trifluoromethylphenyl)-5-methylindenyl)zirconium dichloride;
dimethylsilylenebis(2-(2-(4,5-dimethylfuryl))-4-(4-trimethylsilylphenyl)-5-methylindenyl)zirconium dichloride;
dimethylsilylenebis(2-(2-(4,5-dimethylfuryl))-4-(3,5-dimethylphenyl)-5-methylindenyl)zirconium dichloride;
dimethylsilylenebis(2-(2-(4,5-dimethylfuryl))-4-(3,5-diethylphenyl)-5-methylindenyl)zirconium dichloride;
dimethylsilylenebis(2-(2-(4,5-dimethylfuryl))-4-(3,5-di-i-propylphenyl)-5-methylindenyl)zirconium dichloride;
dimethylsilylenebis(2-(2-(4,5-dimethylfuryl))-4-(3,5-di-t-butylphenyl)-5-methylindenyl)zirconium dichloride;
dimethylsilylenebis(2-(2-(4,5-dimethylfuryl))-4-(3,5-di-methoxyphenyl)-5-methylindenyl)zirconium dichloride;
dimethylsilylenebis(2-(2-(4,5-dimethylfuryl))-4-(3,5-di-trimethylsilylphenyl)-5-methylindenyl)zirconium dichloride;
dimethylsilylenebis(2-(2-(4,5-dimethylfuryl))-4-(3,5-di-trifluoromethylphenyl)-5-methylindenyl)zirconium dichloride;
dimethylsilylenebis(2-(2-(4,5-dimethylfuryl))-4-(3,4,5-trimethylphenyl)-5-methylindenyl)zirconium dichloride;
dimethylsilylenebis(2-(2-(4,5-dimethylfuryl))-4-(3,5-dimethyl-4-trimethylsilylphenyl)-5-methylindenyl)zirconium dichloride;
dimethylsilylenebis(2-(2-(4,5-dimethylfuryl))-4-(3,5-dimethyl-4-biphenyl)-5-methylindenyl)zirconium dichloride;
dimethylsilylenebis(2-(2-(4,5-dimethylfuryl))-4-(3,5-dimethyl-4-methoxyphenyl)-5-methylindenyl)zirconium dichloride;
dimethylsilylenebis(2-(2-(4,5-dimethylfuryl))-4-(3,5-dichloro-4-trimethylsilylphenyl)-5-methylindenyl)zirconium dichloride;
dimethylsilylenebis(2-(2-(4,5-dimethylfuryl))-4-(3,5-dichloro-4-biphenyl)-5-methylindenyl)zirconium dichloride;
dimethylsilylenebis(2-(2-(4,5-dimethylfuryl))-4-(3,5-dichloro-4-methoxyphenyl)-5-methylindenyl)zirconium dichloride;
dimethylsilylenebis(2-(2-(4,5-dimethylfuryl))-4-(1-naphthyl)-5-methylindenyl)zirconium dichloride;
dimethylsilylenebis(2-(2-(4,5-dimethylfuryl))-4-(2-naphthyl)-5-methylindenyl)zirconium dichloride;

dimethylsilylenebis(2-(2-(4,5-dimethylfuryl))-4-(9-phenanthryl)-5-methylindenyl)zirconium dichloride;
dimethylsilylenebis(2-(2-(4,5-dimethylfuryl))-4-(2-phenanthryl)-5-methylindenyl)zirconium dichloride;
dimethylsilylenebis(2-(2-(4,5-dimethylfuryl))-4-phenyl-5-ethylindenyl)zirconium dichloride;
dimethylsilylenebis(2-(2-(4,5-dimethylfuryl))-4-(2-methylphenyl)-5-ethylindenyl)zirconium dichloride;
dimethylsilylenebis(2-(2-(4,5-dimethylfuryl))-4-(2-ethylphenyl)-5-ethylindenyl)zirconium dichloride;
dimethylsilylenebis(2-(2-(4,5-dimethylfuryl))-4-(2-methoxyphenyl)-5-ethylindenyl)zirconium dichloride;
dimethylsilylenebis(2-(2-(4,5-dimethylfuryl))-4-(2-chlorophenyl)-5-ethylindenyl)zirconium dichloride;
dimethylsilylenebis(2-(2-(4,5-dimethylfuryl))-4-(2-biphenyl)-5-ethylindenyl)zirconium dichloride;
dimethylsilylenebis(2-(2-(4,5-dimethylfuryl))-4-(3-methylphenyl)-5-ethylindenyl)zirconium dichloride;
dimethylsilylenebis(2-(2-(4,5-dimethylfuryl))-4-(3-ethylphenyl)-5-ethylindenyl)zirconium dichloride;
dimethylsilylenebis(2-(2-(4,5-dimethylfuryl))-4-(3-methoxyphenyl)-5-ethylindenyl)zirconium dichloride;
dimethylsilylenebis(2-(2-(4,5-dimethylfuryl))-4-(3-chlorophenyl)-5-ethylindenyl)zirconium dichloride;
dimethylsilylenebis(2-(2-(4,5-dimethylfuryl))-4-(3-biphenyl)-5-ethylindenyl)zirconium dichloride;
dimethylsilylenebis(2-(2-(4,5-dimethylfuryl))-4-(4-methylphenyl)-5-ethylindenyl)zirconium dichloride;
dimethylsilylenebis(2-(2-(4,5-dimethylfuryl))-4-(4-ethylphenyl)-5-ethylindenyl)zirconium dichloride;
dimethylsilylenebis(2-(2-(4,5-dimethylfuryl))-4-(4-i-propylphenyl)-5-ethylindenyl)zirconium dichloride;
dimethylsilylenebis(2-(2-(4,5-dimethylfuryl))-4-(4-t-butylphenyl)-5-ethylindenyl)zirconium dichloride;
dimethylsilylenebis(2-(2-(4,5-dimethylfuryl))-4-(4-biphenyl)-5-ethylindenyl)zirconium dichloride;
dimethylsilylenebis(2-(2-(4,5-dimethylfuryl))-4-(4-methoxyphenyl)-5-ethylindenyl)zirconium dichloride;
dimethylsilylenebis(2-(2-(4,5-dimethylfuryl))-4-(4-trifluoromethylphenyl)-5-ethylindenyl)zirconium dichloride;
dimethylsilylenebis(2-(2-(4,5-dimethylfuryl))-4-(4-trimethylsilylphenyl)-5-ethylindenyl)zirconium dichloride;
dimethylsilylenebis(2-(2-(4,5-dimethylfuryl))-4-(3,5-dimethylphenyl)-5-ethylindenyl)zirconium dichloride;
dimethylsilylenebis(2-(2-(4,5-dimethylfuryl))-4-(3,5-diethylphenyl)-5-ethylindenyl)zirconium dichloride;
dimethylsilylenebis(2-(2-(4,5-dimethylfuryl))-4-(3,5-di-i-propylphenyl)-5-ethylindenyl)zirconium dichloride;
dimethylsilylenebis(2-(2-(4,5-dimethylfuryl))-4-(3,5-di-t-butylphenyl)-5-ethylindenyl)zirconium dichloride;
dimethylsilylenebis(2-(2-(4,5-dimethylfuryl))-4-(3,5-dimethoxyphenyl)-5-ethylindenyl)zirconium dichloride;
dimethylsilylenebis(2-(2-(4,5-dimethylfuryl))-4-(3,5-di-trimethylsilylphenyl)-5-ethylindenyl)zirconium dichloride;
dimethylsilylenebis(2-(2-(4,5-dimethylfuryl))-4-(3,5-di-trifluoromethylphenyl)-5-ethylindenyl)zirconium dichloride;
dimethylsilylenebis(2-(2-(4,5-dimethylfuryl))-4-(3,4,5-trimethylphenyl)-5-ethylindenyl)zirconium dichloride;
dimethylsilylenebis(2-(2-(4,5-dimethylfuryl))-4-(3,5-dimethyl-4-trimethylsilylphenyl)-5-ethylindenyl)zirconium dichloride;
dimethylsilylenebis(2-(2-(4,5-dimethylfuryl))-4-(3,5-dimethyl-4-biphenyl)-5-ethylindenyl)zirconium dichloride;
dimethylsilylenebis(2-(2-(4,5-dimethylfuryl))-4-(3,5-dimethyl-4-methoxyphenyl)-5-ethylindenyl)zirconium dichloride;
dimethylsilylenebis(2-(2-(4,5-dimethylfuryl))-4-(3,5-dichloro-4-trimethylsilylphenyl)-5-ethylindenyl)zirconium dichloride;
dimethylsilylenebis(2-(2-(4,5-dimethylfuryl))-4-(3,5-dichloro-4-biphenyl)-5-ethylindenyl)zirconium dichloride;
dimethylsilylenebis(2-(2-(4,5-dimethylfuryl))-4-(3,5-dichloro-4-methoxyphenyl)-5-ethylindenyl)zirconium dichloride;
dimethylsilylenebis(2-(2-(4,5-dimethylfuryl))-4-(1-naphthyl)-5-ethylindenyl)zirconium dichloride;
dimethylsilylenebis(2-(2-(4,5-dimethylfuryl))-4-(2-naphthyl)-5-ethylindenyl)zirconium dichloride;
dimethylsilylenebis(2-(2-(4,5-dimethylfuryl))-4-(9-phenanthryl)-5-ethylindenyl)zirconium dichloride;
dimethylsilylenebis(2-(2-(4,5-dimethylfuryl))-4-(2-phenanthryl)-5-ethylindenyl)zirconium dichloride;
dimethylsilylenebis(2-(2-(4,5-benzofuryl))-4-phenyl-5-methylindenyl)zirconium dichloride;
dimethylsilylenebis(2-(2-(4,5-benzofuryl))-4-(2-methylphenyl)-5-methylindenyl)zirconium dichloride;
dimethylsilylenebis(2-(2-(4,5-benzofuryl))-4-(2-ethylphenyl)-5-methylindenyl)zirconium dichloride;
dimethylsilylenebis(2-(2-(4,5-benzofuryl))-4-(2-methoxyphenyl)-5-methylindenyl)zirconium dichloride;
dimethylsilylenebis(2-(2-(4,5-benzofuryl))-4-(2-chlorophenyl)-5-methylindenyl)zirconium dichloride;
dimethylsilylenebis(2-(2-(4,5-benzofuryl))-4-(2-biphenyl)-5-methylindenyl)zirconium dichloride;
dimethylsilylenebis(2-(2-(4,5-benzofuryl))-4-(3-methylphenyl)-5-methylindenyl)zirconium dichloride;
dimethylsilylenebis(2-(2-(4,5-benzofuryl))-4-(3-ethylphenyl)-5-methylindenyl)zirconium dichloride;
dimethylsilylenebis(2-(2-(4,5-benzofuryl))-4-(3-methoxyphenyl)-5-methylindenyl)zirconium dichloride;
dimethylsilylenebis(2-(2-(4,5-benzofuryl))-4-(3-chlorophenyl)-5-methylindenyl)zirconium dichloride;
dimethylsilylenebis(2-(2-(4,5-benzofuryl))-4-(3-biphenyl)-5-methylindenyl)zirconium dichloride;
dimethylsilylenebis(2-(2-(4,5-benzofuryl))-4-(4-methylphenyl)-5-methylindenyl)zirconium dichloride;
dimethylsilylenebis(2-(2-(4,5-benzofuryl))-4-(4-ethylphenyl)-5-methylindenyl)zirconium dichloride;
dimethylsilylenebis(2-(2-(4,5-benzofuryl))-4-(4-1-propylphenyl)-5-methylindenyl)zirconium dichloride;
dimethylsilylenebis(2-(2-(4,5-benzofuryl))-4-(4-t-butylphenyl)-5-methylindenyl)zirconium dichloride;
dimethylsilylenebis(2-(2-(4,5-benzofuryl))-4-(4-biphenyl)-5-methylindenyl)zirconium dichloride;
dimethylsilylenebis(2-(2-(4,5-benzofuryl))-4-(4-methoxyphenyl)-5-methylindenyl)zirconium dichloride;
dimethylsilylenebis(2-(2-(4,5-benzofuryl))-4-(4-trifluoromethylphenyl)-5-methylindenyl)zirconium dichloride;
dimethylsilylenebis(2-(2-(4,5-benzofuryl))-4-(4-trimethylsilylphenyl)-5-methylindenyl)zirconium dichloride;
dimethylsilylenebis(2-(2-(4,5-benzofuryl))-4-(3,5-dimethylphenyl)-5-methylindenyl)zirconium dichloride;
dimethylsilylenebis(2-(2-(4,5-benzofuryl))-4-(3,5-diethylphenyl)-5-methylindenyl)zirconium dichloride;
dimethylsilylenebis(2-(2-(4,5-benzofuryl))-4-(3,5-di-i-propylphenyl)-5-methylindenyl)zirconium dichloride;
dimethylsilylenebis(2-(2-(4,5-benzofuryl))-4-(3,5-di-t-butylphenyl)-5-methylindenyl)zirconium dichloride;
dimethylsilylenebis(2-(2-(4,5-benzofuryl))-4-(3,5-di-methoxyphenyl)-5-methylindenyl)zirconium dichloride;
dimethylsilylenebis(2-(2-(4,5-benzofuryl))-4-(3,5-di-trimethylsilylphenyl)-5-methylindenyl)zirconium dichloride;

dimethylsilylenebis(2-(2-(4,5-benzofuryl))-4-(3,5-di-trifluoromethylphenyl)-5-methylindenyl)zirconium dichloride;
dimethylsilylenebis(2-(2-(4,5-benzofuryl))-4-(3,4,5-trimethylphenyl)-5-methylindenyl)zirconium dichloride;
dimethylsilylenebis(2-(2-(4,5-benzofuryl))-4-(3,5-dimethyl-4-trimethylsilylphenyl)-5-methylindenyl)zirconium dichloride;
dimethylsilylenebis(2-(2-(4,5-benzofuryl))-4-(3,5-dimethyl-4-biphenyl)-5-methylindenyl)zirconium dichloride;
dimethylsilylenebis(2-(2-(4,5-benzofuryl))-4-(3,5-dimethyl-4-methoxyphenyl)-5-methylindenyl)zirconium dichloride;
dimethylsilylenebis(2-(2-(4,5-benzofuryl))-4-(3,5-dichloro-4-trimethylsilylphenyl)-5-methylindenyl)zirconium dichloride;
dimethylsilylenebis(2-(2-(4,5-benzofuryl))-4-(3,5-dichloro-4-biphenyl)-5-methylindenyl)zirconium dichloride;
dimethylsilylenebis(2-(2-(4,5-benzofuryl))-4-(3,5-dichloro-4-methoxyphenyl)-5-methylindenyl)zirconium dichloride;
dimethylsilylenebis(2-(2-(4,5-benzofuryl))-4-(1-naphthyl)-5-methylindenyl)zirconium dichloride;
dimethylsilylenebis(2-(2-(4,5-benzofuryl))-4-(2-naphthyl)-5-methylindenyl)zirconium dichloride;
dimethylsilylenebis(2-(2-(4,5-benzofuryl))-4-(9-phenanthryl)-5-methylindenyl)zirconium dichloride;
dimethylsilylenebis(2-(2-(4,5-benzofuryl))-4-(2-phenanthryl)-5-methylindenyl)zirconium dichloride;
dimethylsilylenebis(2-(2-(4,5-benzofuryl))-4-phenyl-5-ethylindenyl)zirconium dichloride;
dimethylsilylenebis(2-(2-(4,5-benzofuryl))-4-(2-methylphenyl)-5-ethylindenyl)zirconium dichloride;
dimethylsilylenebis(2-(2-(4,5-benzofuryl))-4-(2-ethylphenyl)-5-ethylindenyl)zirconium dichloride;
dimethylsilylenebis(2-(2-(4,5-benzofuryl))-4-(2-methoxyphenyl)-5-ethylindenyl)zirconium dichloride;
dimethylsilylenebis(2-(2-(4,5-benzofuryl))-4-(2-chlorophenyl)-5-ethylindenyl)zirconium dichloride;
dimethylsilylenebis(2-(2-(4,5-benzofuryl))-4-(2-biphenyl)-5-ethylindenyl)zirconium dichloride;
dimethylsilylenebis(2-(2-(4,5-benzofuryl))-4-(3-methylphenyl)-5-ethylindenyl)zirconium dichloride;
dimethylsilylenebis(2-(2-(4,5-benzofuryl))-4-(3-ethylphenyl)-5-ethylindenyl)zirconium dichloride;
dimethylsilylenebis(2-(2-(4,5-benzofuryl))-4-(3-methoxyphenyl)-5-ethylindenyl)zirconium dichloride;
dimethylsilylenebis(2-(2-(4,5-benzofuryl))-4-(3-chlorophenyl)-5-ethylindenyl)zirconium dichloride;
dimethylsilylenebis(2-(2-(4,5-benzofuryl))-4-(3-biphenyl)-5-ethylindenyl)zirconium dichloride;
dimethylsilylenebis(2-(2-(4,5-benzofuryl))-4-(4-methylphenyl)-5-ethylindenyl)zirconium dichloride;
dimethylsilylenebis(2-(2-(4,5-benzofuryl))-4-(4-ethylphenyl)-5-ethylindenyl)zirconium dichloride;
dimethylsilylenebis(2-(2-(4,5-benzofuryl))-4-(4-1-propylphenyl)-5-ethylindenyl)zirconium dichloride;
dimethylsilylenebis(2-(2-(4,5-benzofuryl))-4-(4-t-butylphenyl)-5-ethylindenyl)zirconium dichloride;
dimethylsilylenebis(2-(2-(4,5-benzofuryl))-4-(4-biphenyl)-5-ethylindenyl)zirconium dichloride;
dimethylsilylenebis(2-(2-(4,5-benzofuryl))-4-(4-methoxyphenyl)-5-ethylindenyl)zirconium dichloride;
dimethylsilylenebis(2-(2-(4,5-benzofuryl))-4-(4-trifluoromethylphenyl)-5-ethylindenyl)zirconium dichloride;
dimethylsilylenebis(2-(2-(4,5-benzofuryl))-4-(4-trimethylsilylphenyl)-5-ethylindenyl)zirconium dichloride;
dimethylsilylenebis(2-(2-(4,5-benzofuryl))-4-(3,5-dimethylphenyl)-5-ethylindenyl)zirconium dichloride;
dimethylsilylenebis(2-(2-(4,5-benzofuryl))-4-(3,5-diethylphenyl)-5-ethylindenyl)zirconium dichloride;
dimethylsilylenebis(2-(2-(4,5-benzofuryl))-4-(3,5-di-i-propylphenyl)-5-ethylindenyl)zirconium dichloride;
dimethylsilylenebis(2-(2-(4,5-benzofuryl))-4-(3,5-di-t-butylphenyl)-5-ethylindenyl)zirconium dichloride;
dimethylsilylenebis(2-(2-(4,5-benzofuryl))-4-(3,5-di-methoxyphenyl)-5-ethylindenyl)zirconium dichloride;
dimethylsilylenebis(2-(2-(4,5-benzofuryl))-4-(3,5-di-trimethylsilylphenyl)-5-ethylindenyl)zirconium dichloride;
dimethylsilylenebis(2-(2-(4,5-benzofuryl))-4-(3,5-di-trifluoromethylphenyl)-5-ethylindenyl)zirconium dichloride;
dimethylsilylenebis(2-(2-(4,5-benzofuryl))-4-(3,4,5-trimethylphenyl)-5-ethylindenyl)zirconium dichloride;
dimethylsilylenebis(2-(2-(4,5-benzofuryl))-4-(3,5-dimethyl-4-trimethylsilylphenyl)-5-ethylindenyl)zirconium dichloride;
dimethylsilylenebis(2-(2-(4,5-benzofuryl))-4-(3,5-dimethyl-4-biphenyl)-5-ethylindenyl)zirconium dichloride;
dimethylsilylenebis(2-(2-(4,5-benzofuryl))-4-(3,5-dimethyl-4-methoxyphenyl)-5-ethylindenyl)zirconium dichloride;
dimethylsilylenebis(2-(2-(4,5-benzofuryl))-4-(3,5-dichloro-4-trimethylsilylphenyl)-5-ethylindenyl)zirconium dichloride;
dimethylsilylenebis(2-(2-(4,5-benzofuryl))-4-(3,5-dichloro-4-biphenyl)-5-ethylindenyl)zirconium dichloride;
dimethylsilylenebis(2-(2-(4,5-benzofuryl))-4-(3,5-dichloro-4-methoxyphenyl)-5-ethylindenyl)zirconium dichloride;
dimethylsilylenebis(2-(2-(4,5-benzofuryl))-4-(1-naphthyl)-5-ethylindenyl)zirconium dichloride;
dimethylsilylenebis(2-(2-(4,5-benzofuryl))-4-(2-naphthyl)-5-ethylindenyl)zirconium dichloride;
dimethylsilylenebis(2-(2-(4,5-benzofuryl))-4-(9-phenanthryl)-5-ethylindenyl)zirconium dichloride;
dimethylsilylenebis(2-(2-(4,5-benzofuryl))-4-(2-phenanthryl)-5-ethylindenyl)zirconium dichloride;
dimethylsilylene(2-(2-(5-methylfuryl))-4-phenyl-5-methylindenyl)(4-phenyl-5-methylindenyl)zirconium dichloride;
dimethylsilylene(2-(2-(5-methylfuryl))-4-phenyl-5-methylindenyl)(2-methyl-4-phenyl-5-methylindenyl)zirconium dichloride;
dimethylsilylene(2-(2-(5-methylfuryl))-4-phenyl-5-methylindenyl)(2-methyl-4-phenylindenyl)zirconium dichloride;
dimethylsilylene(2-(2-(5-methylfuryl))-4-phenyl-5-methylindenyl)(2-ethyl-4-phenyl-5-methylindenyl)zirconium dichloride;
dimethylsilylene(2-(2-(5-methylfuryl))-4-phenyl-5-methylindenyl)(2-i-propyl-4-phenyl-5-methylindenyl)zirconium dichloride;
dimethylsilylene(2-(2-(5-methylfuryl))-4-phenyl-5-methylindenyl)(2-n-butyl-4-phenyl-5-methylindenyl)zirconium dichloride;
dimethylsilylene(2-(2-(5-methylfuryl))-4-(3,5-dimethylphenyl)-5-methylindenyl)(4-(3,5-dimethylphenyl)-5-methylindenyl)zirconium dichloride;
dimethylsilylene(2-(2-(5-methylfuryl))-4-(3,5-dimethylphenyl)-5-methylindenyl)(2-methyl-4-(3,5-dimethylphenyl)-5-methylindenyl)zirconium dichloride;
dimethylsilylene(2-(2-(5-methylfuryl))-4-(3,5-dimethylphenyl)-5-methylindenyl)(2-methyl-4-(3,5-dimethylphenyl)indenyl)zirconium dichloride;
dimethylsilylene(2-(2-(5-methylfuryl))-4-(3,5-dimethylphenyl)-5-methylindenyl)(2-ethyl-4-(3,5-dimethylphenyl)-5-methylindenyl)zirconium dichloride;

dimethylsilylene(2-(2-(5-methylfuryl))-4-(3,5-dimethylphenyl)-5-methylindenyl)(2-i-propyl-4-(3,5-dimethylphenyl)-5-methylindenyl)zirconium dichloride;
dimethylsilylene(2-(2-(5-methylfuryl))-4-(3,5-dimethylphenyl)-5-methylindenyl)(2-n-butyl-4-(3,5-dimethylphenyl)-5-methylindenyl)zirconium dichloride;
dimethylsilylene(2-(2-(5-methylfuryl))-4-(4-t-butylphenyl)-5-methylindenyl)(4-(4-t-butylphenyl)-5-methylindenyl)zirconium dichloride;
dimethylsilylene(2-(2-(5-methylfuryl))-4-(4-t-butylphenyl)-5-methylindenyl)(2-methyl-4-(4-t-butylphenyl)-5-methylindenyl)zirconium dichloride;
dimethylsilylene(2-(2-(5-methylfuryl))-4-(4-t-butylphenyl)-5-methylindenyl)(2-methyl-4-(4-t-butylphenyl)indenyl)zirconium dichloride;
dimethylsilylene(2-(2-(5-methylfuryl))-4-(4-t-butylphenyl)-5-methylindenyl)(2-ethyl-4-(4-t-butylphenyl)-5-methylindenyl)zirconium dichloride;
dimethylsilylene(2-(2-(5-methylfuryl))-4-(4-t-butylphenyl)-5-methylindenyl)(2-i-propyl-4-(4-t-butylphenyl)-5-methylindenyl)zirconium dichloride;
dimethylsilylene(2-(2-(5-methylfuryl))-4-(4-t-butylphenyl)-5-methylindenyl)(2-n-butyl-4-(4-t-butylphenyl)-5-methylindenyl)zirconium dichloride;
dimethylsilylene(2-(2-(5-methylfuryl))-4-(4-t-butylphenyl)-5-methylindenyl)(4-(3,5-dimethylphenyl)-5-methylindenyl)zirconium dichloride;
dimethylsilylene(2-(2-(5-methylfuryl))-4-(4-t-butylphenyl)-5-methylindenyl)(2-methyl-4-(3,5-dimethylphenyl)-5-methylindenyl)zirconium dichloride;
dimethylsilylene(2-(2-(5-methylfuryl))-4-(4-t-butylphenyl)-5-methylindenyl)(2-methyl-4-(3,5-dimethylphenyl)indenyl)zirconium dichloride;
dimethylsilylene(2-(2-(5-methylfuryl))-4-(4-t-butylphenyl)-5-methylindenyl)(2-ethyl-4-(3,5-dimethylphenyl)-5-methylindenyl)zirconium dichloride;
dimethylsilylene(2-(2-(5-methylfuryl))-4-(4-t-butylphenyl)-5-methylindenyl)(2-i-propyl-4-(3,5-dimethylphenyl)-5-methylindenyl)zirconium dichloride;
dimethylsilylene(2-(2-(5-methylfuryl))-4-(4-t-butylphenyl)-5-methylindenyl)(2-n-butyl-4-(3,5-dimethylphenyl)-5-methylindenyl)zirconium dichloride.

In addition to this, the compounds in which cross-linking part Y of the exemplified compounds are diethylsilylene, diphenylsilylene, dimethylgermylene, diethylgermylene or diphenylgermylene instead of dimethylsilylene, or the compounds in which one or both of $X^1$, $X^2$ are replaced by bromine atom, iodine atom, methyl group, phenyl group, benzyl group, dimethylamino group, diethylamino group and the like instead of exemplified chlorine can be exemplified.

Synthetic Method of Metallocene Complex:

Metallocene complex (compound) of the present invention can be synthesized by optional method depending on the type of substituent or bonding. One typical example of synthetic pathway is described below.

[Formula 5]

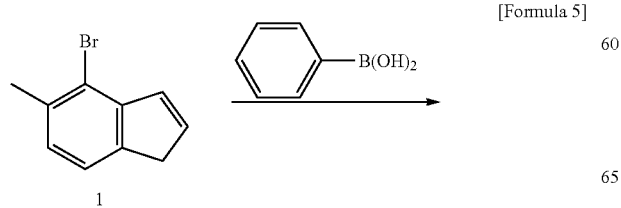

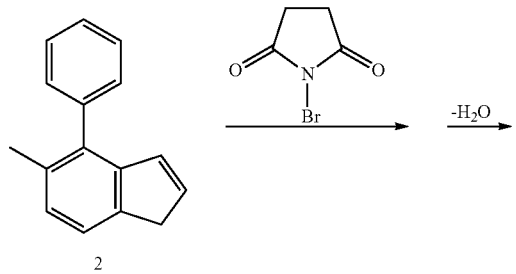

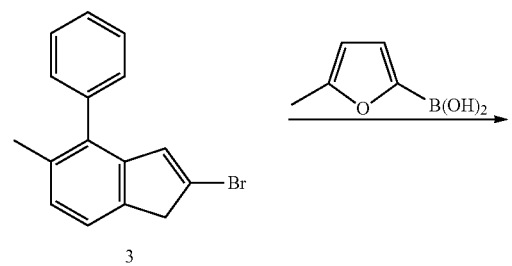

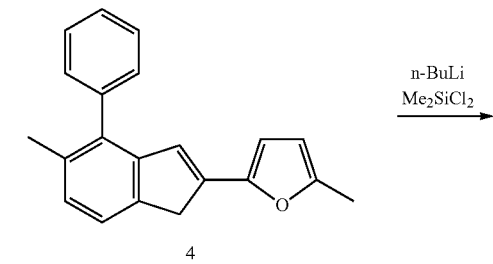

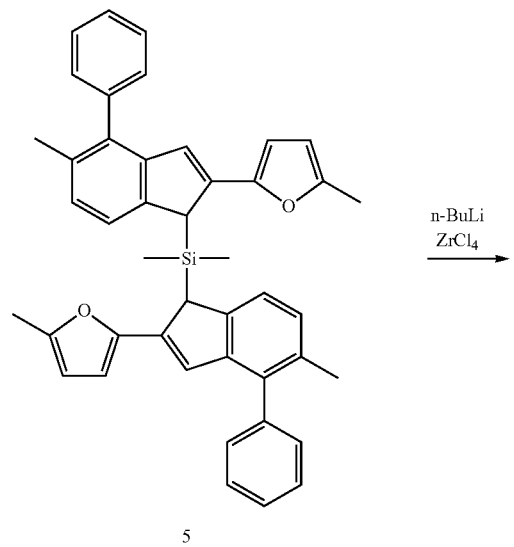

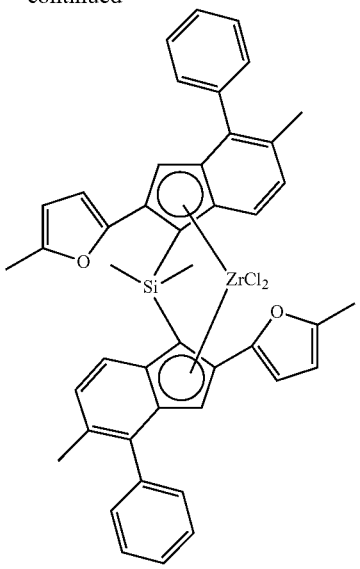

6

In the above-described synthetic pathway, coupling reaction of 1 and phenylboronic acid in the presence of palladium catalyst is carried out to provide 2. Bromination from 2 to 3 can be carried out according to the method described in the reference (J. Org. Chem. 1982, 47, 705-709) and the like, 2 is reacted with N-bromosuccinimide in the presence of water, and is dehydrated by acid such as p-toluene sulfonic acid to obtain 3. Coupling reaction of 3 and 5-methylfuryl-2-boronic acid is carried out in the presence of palladium catalyst to obtain 4. After 4 is anionized by butyllithium and the like, cross-linking form of 5 can be obtained by reacting with dimethyldichlorosilane. After 5 is dianionized by 2 equivalents of butyllithium, metallocene complex 6 can be obtained by reacting with zirconium tetrachloride.

Synthesis of metallocene complex in which substituent was introduced can be carried out by using the corresponding raw material for substitution, and the corresponding 2-position substituent ($R^1$, $R^{11}$) can be introduced by using the corresponding boronic acid, for example, 4,5-dimethylfuryl-2-boronic acid, 2-thienylboronic acid and the like instead of 5-methylfuryl-2-boronic acid, and introduction of alkyl group to 2-position substituent ($R^1$, $R^{11}$) can be carried out by reacting 3 with Grignard reagent in the presence of Ni catalyst as the method described in reference (J. Org. Chem. 1984, 49, 4226).

Synthesis of the metallocene complex having different substituents on two indenyl rings can be carried out by cross-linking of the sequential reactions of differently substituted indenes with $Me_2YCl_2$. In addition, auxiliary reagent of cross-linking such as amine compound (for example, methylimidazole) may exist at cross-linking.

2. Catalyst for Olefin Polymerization

The metallocene complex of the present invention forms a catalyst component for olefin polymerization, said catalyst component can be used as the catalyst for olefin polymerization. For example, said metallocene complex component is contained as a component (A), and is preferably used as the catalyst for olefin polymerization as described below.

(1) Catalyst Component for Olefin Polymerization

The catalyst for olefin polymerization of the present invention contains the following (A), (B) and (C) components:

Component (A): metallocene complex represented by the general formula [I];

Component (B): compound forming ionic pair by reacting with component (A) or the ion-exchanging layered silicate, preferably the ion-exchanging layered silicate;

Component (C): organic aluminum compound.

(2) About Each Components:

As metallocene complexes represented by the general formula [I] of components A, 2 kinds or more of same or different compounds represented by the general formula [I] may be used.

Components (B) of the compound forming ionic pair by reacting component (A) or the ion-exchanging layered silicate include aluminum oxy compound, boron compound, the ion-exchanging layered silicate and the like, preferably it is the ion-exchanging layered silicate. These components (B) may be used alone, or in combination of two or more kinds.

In aluminum oxy compounds, it has been known that aluminum oxy compounds can activate metallocene complex, and such compounds include, specifically, the compounds represented by the following each general formula.

[Formula 6]

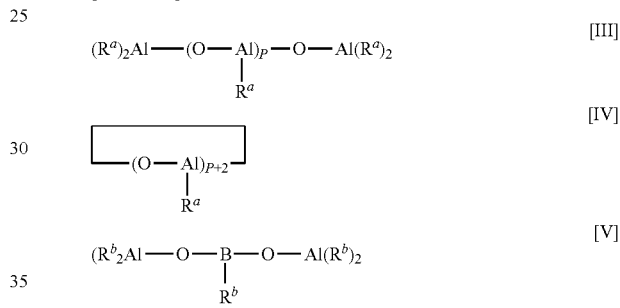

In the above-described each general formula, $R^a$ represents hydrogen or hydrocarbon group, preferably hydrocarbon group having 1 to 10 carbon number, particularly preferably 1 to 6 carbon number. In addition, a plurality of $R^a$ may be same or different respectively. In addition, p represents a integer of 0 to 40, preferably 2 to 30.

In addition, the compounds represented by the general formula [III], [IV] are so-called aluminoxane compound, among them, methyl aluminoxane or methylisobutyl aluminoxane is preferable. These aluminoxanes may be used in combination of the same or different groups of compounds. And, the above-described aluminoxane can be prepared under the known various conditions.

Further, the compound represented by the general formula [V] can be obtained by the reaction of 10:1 to 1:1 (molar ratio) of one or more trialkylaluminum and alkyl boronic acid represented by the general formula $R^bB(OH)_2$. In the general formula, $R^b$ represents hydrocarbon group having 1 to 10 carbon number, preferably 1 to 6 carbon number.

In addition, boron compounds include the complex compound of cation such as carbonium cation, ammonium cation and organic boron compound such as triphenylboron, tris(3,5-difluorophenyl)boron, tris(pentafluorophenyl)boron, or various organic boron compounds, for example, tris(pentafluorophenyl)boron and the like.

The ion-exchanging layered silicate (hereinafter, may be abbreviated only as "silicate") is the silicate compound having a crystal structure in which a plane composed by ionic bonding is each other built up in parallel by bonding force, and the convertibility of containing ions. Various silicates are known, specifically, are described in publication, "Nendo Koubutu Gaku" (Clay Mineralogy) by Haruo Shiromizu, 1995, Asakura Publishing Co., Ltd.

As component (B) of the present invention, smectite group is preferably used, specifically, montmorillonite, sauconite, beidellite, nontronite, saponite, hectorite, stevensite and the like can be exemplified. Among them, montmorillonite is preferable in view of activity of rubber component, molecular weight.

Most of silicates are produced as main component of clay mineral in nature, therefore, the impurities other than the ion-exchanging layered silicate (quartz, cristobalite and the like) are frequently contained, and impurities contained in silicate of smectite group used in the present invention is acceptable.

Granulation of the Ion-Exchanging Layered Silicate:

Silicate may be used as dry state, or may be used as slurry state. In addition, the shape of the ion-exchanging layered silicate is not particularly limited, naturally produced shape or shape when artificially synthesized may be acceptable, in addition, the ion-exchanging layered silicate which shape is processed by the operation such as pulverization, granulation, classification may be used. Among them, use of granulated silicate is particularly preferable because of providing excellent particle shape of polymer.

Shape processing of the ion-exchanging layered silicate such as granulation, pulverization, classification may be carried out before acid treatment, or shape processing may be carried out after acid treatment.

Granulation methods to be used here, include, for example, agitating granulation method, spray granulation method, tumbling granulation method, briquetting, compacting, extrusion granulation method, fluidized bed granulation method, emulsion granulation method, submerged granulation method, compression molding granulation method and the like, and are not particularly limited. Preferably, agitating granulation method, spray granulation method, tumbling granulation method, fluidized bed granulation method are exemplified, and particularly preferably, agitating granulation method, spray granulation method are exemplified.

It should be noted that, when spray granulation method is carried out, as dispersion media of raw material slurry, water or organic solvent such as methanol, ethanol, chloroform, methylene chloride, pentane, hexane, heptane, toluene, xylene is used. Preferably, water is used as dispersion media. Concentration of component (B) in raw material slurry liquid of spray granulation, in which spherical particles is obtained, is 0.1 to 30% by weight, preferably 0.5 to 20% by weight, particularly preferably 1 to 10% by weight. Inlet temperature of hot air in spray granulation, in which spherical particles is obtained, is different depending on dispersion media, in case of water, it is carried out at 80 to 260° C., preferably 100 to 220° C.

To obtain a carrier having high particle strength in granulation, and to improve polymerization activity of propylene, silicate is micronized as needed. Silicate may be micronized by any method. As micronization method, any of dry milling or wet milling can be used. Preferably, wet milling in which water is used as dispersion media and swellability of silicate is utilized is preferable, for example, there are the method by forced agitation method using Polytron and the like, or the method by Dynomill, Pearlmill and the like. Average diameter of particle before granulation is 0.01 to 3 µm, preferably, 0.05 to 1 µm.

In addition, when granulating, organic material, inorganic material, inorganic salt, various binders may be used. The binders to be used include for example, magnesium chloride, aluminum sulfate, aluminum chloride, magnesium sulfate, alcohols, glycols and the like.

Spherical particles obtained by the above-described method preferably have 0.2 MPa or more of the crush strength of particle to inhibit crushing or generation of dust in polymerization process. In addition, particle diameter range of the granulated ion-exchanging layered silicate is 0.1 to 1000 µm, preferably 1 to 500 µm. Pulverizing method is not particularly limited, any of dry pulverization, wet pulverization may be used.

Acid Treatment:

Silicate used in the present invention is used after acid treatment, or may be treated in combination of the other chemical treatment. The other chemical treatments include alkali treatment, salts treatment, organic material treatment and the like.

Acid strength of solid can be changed by acid treatment of silicate. In addition, acid treatment has an effect of removing the impurities of ion-exchanging or surface as well as an effect of dissolving part of cation such as Al, Fe, Mg, Li in the crystal structure.

Acids used in acid treatment include hydrochloric acid, nitric acid, sulfuric acid, phosphoric acid, acetic acid, oxalic acid, benzoic acid, stearic acid, propionic acid, acrylic acid, maleic acid, fumaric acid, phthalic acid and the like. These may be simultaneously used in combination of two or more kinds. Among them, inorganic acid is preferable, sulfuric acid, hydrochloric acid, nitric acid are preferable, sulfuric acid is further preferable.

In addition, combination method of acid treatment and salts treatment is particularly preferable, there are the method of acid treatment after salts treatment, the method of salts treatment after acid treatment, the method of simultaneously carrying out salts treatment and acid treatment, the method of simultaneously carrying out salts treatment and acid treatment after salts treatment, and the like.

As condition by acid treatment, condition that acid concentration is 0.1 to 30% by weight, treatment temperature is the temperature range from room temperature to boiling point of used solvent. treatment time is 5 minutes to 24 hours, is usually selected, and the condition that at least part of the compound to be treated is dissolved, is preferable. In addition, acid is generally used as aqueous solution. For example, when using sulfuric acid, it is preferable that treatment temperature is 80° C. to 100° C., treatment time is 0.5 hours or more and less than 5 hours.

By carrying out salts treatment simultaneously, surface area and interlayer distance can be changed by formation of ionic composite, molecular composite, organic derivatives and the like. For example, by utilizing ion exchangeability, layered substance exhibiting a state of enlarged interlayer can be obtained by replacing interlayer exchangeable ion by the other bulky ion.

When the above-described acid treatment is carried out, shape control may be carried out by using pulverization or granulation before treatment, during treatment, after treatment. In addition, chemical treatment such as alkaline treatment, organic compound treatment, organic metal treatment may be used simultaneously.

Salts to be used in ion exchanging is a compound which comprises cation having at least 1 kind of atom selected from the group consisting of 1 to 14 group atoms, preferably a compound which comprises cation having at least 1 kind of atom selected from the group consisting of 1 to 14 group atoms and anion derived from at least 1 kind of atom or atomic group selected from the group consisting of halogen atom, inorganic acid and organic acid, further preferably, a compound which comprises cation having at least 1 kind of atom selected from the group consisting of 2 to 14 group atoms and at least 1 kind of anion selected from the group consisting of Cl, Br, I, F, $PO_4$, $SO_4$, $NO_3$, $CO_3$, $C_2O_4$, $ClO_3$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH, $OOCCH_2CH_3$, $C_2H_4O_4$, $C_6H_5O_7$. In addition, these salts may be simultaneously used in combination of two or more kinds.

As silicates obtained in this way, pore volume in which radius measured by mercury intrusion technique is 20 Å or more is 0.1 cc/g or more, particularly preferably 0.3 to 5 cc/g. Such silicates contain adsorbed water and interlayer water when treated in aqueous solution. Here, adsorbed water is the water adsorbed on the surface of silicates or crystal fracture surface, and interlayer water is the water existing in interlayer.

Silicates is preferably used after removing the above-described adsorbed water and interlayer water. Although dehydrating method is not particularly limited, heating dehydration, heating dehydration under gas flow, heating dehydration under reduced pressure and azeotropic dehydration with organic solvent and the like can be used. Heating temperature is controlled to the temperature range that adsorbed water and interlayer water cannot remain, and is usually 100° C. or more, preferably 150° C. or more, but high temperature condition in which structural fracture is occurred is not preferable. Heating time is 0.5 hours or more, preferably 1 hour or more. In this case, as a value of weight reduction of silicates after dehydrating drying at the condition of 200° C. of temperature, 1 mmHg of pressure, 2 hours of suction time, 3% or less by weight is preferable. In the present invention, when silicates controlled to 3% or less by weight of weight reduction is used, this is preferably handled so as to keep the same weight reduction in contact with component (A) and component (C).

Composition of Silicates after Acid Treatment:

Acid treated silicates of the component (B) relevant to the present invention, show 0.01 to 0.29 as Al/Si atomic ratio, preferably the range of 0.03 to 0.25, further preferably the range of 0.05 to 0.23 in view of activity of polymerization catalyst, and molecular weight of rubber component.

Al/Si atomic ratio becomes index of acid treatment strength in clay parts, and control of Al/Si atomic ratio can be carried out by adjusting acid species, acid concentration, acid treatment time and acid treatment temperature at carrying out acid treatment.

Aluminum and silicon in silicates are measured by the method that calibration curve is made based on the method of chemical analysis according to JIS method, therefore, and quantitative determination is carried out by fluorescent X-ray spectroscopy.

Component (C):

One example of organic aluminum compound represents the following general formula.

$$AlR_aX_{3-a}$$

In the general formula, R represents hydrocarbon group having 1 to 20 carbon number, X represents hydrogen, halogen, alkoxy group or siloxy group, "a" represents number of more than 0 and 3 or less. Specific examples of organic aluminum compound represented by general formula include trialkylaluminum such as trimethylaluminum, triethylaluminum, tripropylaluminum, triisobutylaluminum; halogen or alkoxy containing alkylaluminum such as diethylaluminum monochloride, diethylaluminum monomethoxide. Among them, trialkylaluminum is preferable. In addition, the above-described organic aluminum compound may be used in combination of two or more kinds.

(3) Preparation Method of Catalyst

In the preparation method of catalyst for olefin polymerization relevant to the present invention, contacting method of component (A), component (B) and component (C) is not particularly limited, the following method can be exemplified:

(i) method of adding component (C) after component (A) and component (B) are contacted;

(ii) method of adding component (B) after component (A) and component (C) are contacted;

(iii) method of adding component (A) after component (B) and component (C) are contacted;

(iv) method of contacting each components (A), (B), (C) simultaneously.

Further, the another kind of component may be used as mixture in each components, and each components may be contacted in the different order. It should be noted that, this contact may be carried out not only in case of preparation of catalyst, but also in case of pre-polymerization by olefin, or polymerization of olefin.

In addition, the component may be separately contacted with each components in such a manner that after component (B) and component (C) is contacted, mixture of component (A) and component (C) is added.

Contact of the above-described components (A), (B), (C) is preferably carried out in inert gas such as nitrogen, and in inert hydrocarbon solvent such as pentane, hexane, heptane, toluene, xylene. Contact can be carried out at the temperature between −20° C. and boiling point of solvent, particularly, can be preferably carried out at the temperature between room temperature and boiling point of solvent.

In the catalyst relevant to the present invention, when component (B) is silicates, preferable use amount of component (A), component (B) and component (C) are 0.001 to 10 mmol of metallocene complex of component (A) relative to 1 g of component (B), more preferably the range of 0.001 to 1 mmol. Use amount of component (C) is 0.1 or more and 100,000 or less as molar ratio of Al/metallocene complex, preferably 1 or more and 10,000 or less. These use ratio shows example of usual ratio, the present invention is not limited by the range of use described-above, as long as the catalyst is in accordance with the object of the present invention.

Before catalyst containing component (A), (B), (C) is used as a catalyst of olefin polymerization (main polymerization), pre-polymerization treatment that olefin such as ethylene, propylene, 1-butene, 1-hexene, 1-octene, 4-methyl-1-pentene, 3-methyl-1-butene, vinylcycloalkane, styrene was preliminarily polymerized in small amount as necessary may be carried out. As method of pre-polymerization, the known method can be used.

As a amount of polymer obtained by pre-polymerization, amount of 1 to 10 times relative to the weight of catalyst is preferably polymerized, as a monomer, ethylene or propylene is preferable.

3. Polymerization Method

In the present invention, as a mode of polymerization, any method can be employed, provided that catalyst for polymerization including metallocene complex represented by the above-described general formula [1] and monomer can be efficiently contacted, and polymerization or copolymerization of olefin can be carried out.

Specifically, slurry method using inert solvent, bulk polymerization method using propylene as solvent without substantially using inert solvent, or gas-phase polymerization method keeping each monomers as gas state without substantially using inert liquid solvent, can be employed.

In polymerization method, method of continuous polymerization, batch-type polymerization or pre-polymerization are applied.

In addition, combination of polymerization mode is not particularly limited, mode such as two stages of bulk polymerization, gas-phase polymerization after bulk polymerization, two stages of gas-phase polymerization can be employed, further, furthermore multi-stages polymerization method can be employed.

In order to obtain the polymer having particularly excellent particle shape, it is preferable that bulk polymerization is carried out in the first step, and gas-phase polymerization is carried out in the second step, or gas-phase polymerization is carried out in both of the first step and the second step.

By using the catalyst of the present invention, high molecular weight copolymer can be produced, in addition, propylene type polymer having stiffness and impact resistance can be produced, and as production method, polymerization method having the following step 1 and step 2 is preferable, particularly preferably, polymerization method that step 2 is carried out successively after step 1. In addition, multi-step polymerization method that polymerization is carried out by three or more stages in combination with the another polymerization condition, can be carried out.

[Step 1]:

Step 1 is the step of polymerizing 90 to 100% by weight of propylene, 10% or less by weight of ethylene or α-olefin relative to total monomer component.

In slurry polymerization, as polymerization solvent, saturated aliphatic or aromatic hydrocarbon such as hexane, heptane, pentane, cyclohexane, benzene, toluene is used alone or in combination thereof.

Polymerization temperature is 0 to 150° C., in addition, hydrogen can be supplementarily used as molecular weight regulation agent. Polymerization pressure is suitable at 0 to 3 MPaG, preferably 0.3 to 2 MPaG.

In case of bulk polymerization, polymerization temperature is 0 to 90° C., preferably, 60 to 80° C. Polymerization pressure is suitable at 0 to 5 MPaG, preferably 1 to 4 MPaG.

In case of gas-phase polymerization, polymerization temperature is 0 to 200° C., preferably, to 120° C., further preferably 60 to 100° C. Polymerization pressure is suitable at 0 to 4 MPaG, preferably 1 to 3 MPaG.

In addition, 0 to 10% of ethylene or α-olefin relative to total monomer component, in which the shape of polymer is not adversely affected, can coexist, and molecular weight, activity, melting point can be adjusted. In addition, as molecular weight regulation agent, hydrogen may be used.

[Step 2]:

Step 2 is the step of polymerizing 10 to 90% by weight of propylene, 10 to 90% by weight of ethylene or α-olefin relative to total monomer component, and rubber component exhibiting suitable impact resistance can be produced. Amount of propylene relative to monomer component is preferably 20 to 80% by weight in view of providing the propylene polymer having high impact resistance, more preferably 20 to 60% by weight.

As polymerization condition of the second step, slurry polymerization, bulk polymerization are the same as the first step, but in case of gas-phase polymerization, polymerization temperature is 0 to 200° C., preferably 20 to 90° C., further preferably 30 to 80° C. because monomer composition is different from the first step. Polymerization pressure is suitable at 0 to 4 MPaG, preferably 1 to 3 MPaG. In addition, as molecular weight regulation agent, hydrogen may be used.

In step 2, when ethylene is used as monomer, in propylene type polymer obtained by the polymerization method of the present invention, part including ethylene can be observed in parts soluble at 100° C. in CFC-IR. Improvement of impact resistance and transparency is estimated by this part including ethylene.

In addition, content of CP part obtained from step 2 in impact copolymer obtained by the present invention is preferably 5 to 60% by weight in view of the balance of stiffness and impact resistance, more preferably 10 to 50% by weight.

[Polymerization Monomer]

In the present invention, "α-olefin" represents olefin having 3 to 20 carbon number, and includes, specifically, propylene, 1-butene, 1-pentene, 1-hexene, 1-heptene, 1-octene, 1-decene, 1-dodecene, 1-hexadecene, 4-methyl-1-pentene, styrene, vinylcyclohexane, diene, triene, cyclic olefin and the like.

A monomer to be used with propylene, is preferably, ethylene, 1-butene, further preferably ethylene. In addition, these monomers can be used in combination.

[Analysis of Characteristic Value of Polymerized Olefin Polymer]

Contents of copolymer component (it is a rubber component, hereinafter, called as "CP") obtained in the second step of propylene type polymer obtained by using the catalyst relevant to the present invention, ethylene in CP, or polymerization ratio of α-olefin are measured by the following methods.

It should be noted that, the following examples are one using ethylene in CP, it is assumed that when α-olefin other than ethylene is used, these values are measured by the method according to the following examples.

(1) Analytical Equipments to be Used (i) Cross-Fractionation Equipment

CFC T-100: manufactured by Dia Instruments Co., Ltd;

(ii) Fourier Transform Infrared Spectroscopy (FT-IR):

1760X: manufactured by Perkin-Elmer Inc;

Wavelength fixed infrared spectrometer equipped as a detector of CFC (cross-fractionation chromatography) is dismounted and FT-IR is mounted to CFC, then, this FT-IR is used as detector.

Transfer-line from outlet of solution eluted from CFC to FT-IR is set to 1 m of length, throughout the measurement, temperature is maintained at 140° C. Flow-cell equipped to FTIR has 1 mm of light path length, 5 mmφ of light breadth length, throughout the measurement, temperature is maintained at 140° C.

(iii) Gel Permeation Chromatography (GPC):

In latter stage of CFC, three pieces of GPC column (AD806MS: manufactured by Shouwa Denkou KK) are connected in series and used.

(2) Measurement Condition of CFC (i) Solvent: ortho-dichlorobenzene (ODCB);

(ii) Sample concentration: 4 mg/mL;

(iii) Injection Volume: 0.4 mL;

(iv) Crystallization: Temperature is decreased from 140° C. to 40° C. for 40 minutes.

(v) Fractionation method:

Fractionation temperature in elution fractionation when temperature is rising is set to 40, 100, 140° C., and fractionation is carried out in 3 fraction in total.

It should be noted that, elution ratio (unit: % by weight) of component (Fraction 1) eluted at the temperature of 40° C. or less, component (Fraction 2) eluted at the temperature range of 40 to 100° C., component (Fraction 3) eluted at the temperature range of 100 to 140° C. are defined as W40, W100, W140 respectively. W40+W100+W140=100. In addition, each fractions fractionated are automatically transferred to FT-IR analytical equipment as it is.

(vi) Elution rate of solvent at elution: 1 mL/min.

(3) Measurement Condition of FT-IR

After elution of sample solution is started from GPC in latter stage of CFC, measurement of FT-IR is carried out as the following condition, and GPC-IR data are collected in the above-described each fractions 1 to 3.

(i) Detector: MCT;
(ii) Resolution Capability: 8 $cm^{-1}$;
(iii) Measurement Interval: 0.2 minute (12 sec);
(iv) Cumulated number per one measurement: 15 times;

(4) Post-Processing and Analysis of Measurement Results

Eluted amount and molecular weight distribution of the components eluted at each temperatures are measured by using absorbance at 2945 $cm^{-1}$ as chromatogram. Eluted volume is normalized so that sum of eluted volume of each eluted components becomes 100%. Conversion of retention volume to molecular weight is carried out by using the calibration curve based on the standard polystyrenes, made in advance. The used standard polystyrenes are the following trade names produced by Tosoh Corporation:
(F380, F288, F128, F80, F40, F20, F10, F4, F1, A5000, A2500, A1000).

Calibration curve is made injecting 0.4 mL of solution, in which is dissolved in ODCB (includes 0.5 mg/mL of BHT) so that each components become 0.5 mg/mL respectively. Calibration curve uses the tertiary equation obtained by approximation using least-square method. Conversion to molecular weight is carried out by using general calibration curve as reference to the publication "Size Exclusion Chromatography" by Sadao Mori, Kyoritsu Shuppan Co., Ltd. Viscosity equation used in this case ($[\eta]=K\times M'$) uses the following numerical value.

(i) In the case of making calibration curve using standard polystyrene:

K=0.000138, α=0.70

(ii) In the case of measuring the sample of propylene type block-copolymer:

K=0.000103, α=0.78

Ethylene content distribution of each elution components (distribution of ethylene content along molecular weight axis) are determined by conversion to ethylene polymerization ratio (mol %) using the ratio of absorbance in 2956 $cm^{-1}$ and absorbance in 2927 $cm^{-1}$ obtained from GPC-IR, based on calibration curve made in advance using ethylene-propylene copolymer (EPR) and the mixture thereof, in which ethylene content is known by measuring polyethylene, polypropylene, $^{13}$C-NMR measurement and the like.

(5) CP Content

CP content of propylene type block-copolymer in the present invention is defined as the following equation (I), and is determined in the following procedure.

$$CP\ content(\%\ by\ weight)=W40\times A40/B40+W100\times A100/B100 \quad (I)$$

In equation (I), W40, W100 are elution ratio in the above-described each fractions (unit: % by weight), and A40, A100 are the average ethylene content (unit: % by weight) measured practically in each fractions corresponding to W40, W100, and B40, B100 are ethylene content (unit: % by weight) in CP contained in each fractions. Determination methods of A40, A100, B40, B100 are described later.

In addition, meaning of equation (I) is as follows.

That is, the first term of right-hand in equation (I) is the term in which amount of CP contained in fraction 1 (parts soluble at 40° C.) is calculated. When fraction 1 contains only CP, and does not contain PP, W40 contributes to content of CP derived from fraction 1 in total as it is, but in fraction 1, small amount of component derived from PP (extremely low molecular weight component and atactic polypropylene) is contained other than the component derived from CP, therefore, this part is needed to correct. Then, amount derived from CP component in fraction 1 is calculated by multiplying W40 by A40/B40. For example, when average ethylene content (A40) in fraction 1 is 30% by weight, and ethylene content in CP (B40) contained in fraction 1 is 40% by weight, amount of 30/40=¾ (i.e. 75% by weight) in fraction 1 is an amount derived from CP, ¼ is amount derived from PP. Thus, in first term of right-hand in equation (I), operation of multiplying A40/B40 means to calculate the contribution of CP from % by weight (W40) in fraction 1. The second term of right-hand is the same as first term, in each fractions, contribution of CP is calculated, then, sum of each contribution is the content of CP.

Average ethylene contents in fraction 1 to 3 (A40, A100, A140) are obtained by sum of product of weight ratio of every data-point in chromatogram of absorbance in 2945 $cm^{-1}$ and ethylene content (obtained from the ratio of absorbance in 2956 $cm^{-1}$ and absorbance in 2927 $cm^{-1}$) of every data-point.

Ethylene content corresponding to peak position in differential molecular weight distribution curve in fraction 1 is defined as B40 (unit: % by weight).

As for fraction 2, rubber part is estimated to dissolve completely, so it cannot be specified by the similar definition, therefore, it is defined as B100=100 in the present invention. B40, B100 are ethylene contents in CP contained in each fractions, however, it is substantially impossible to measure these values analytically. That reason is due to that there is no means to separate PP and PE mixed in fraction completely.

From the results of investigating by using various model samples, it is found that B40 can explain reasonably the improvement effect of material properties when ethylene content corresponding to peak position in differential molecular weight distribution curve in fraction 1 is used. In addition, by two reasons that B100 has crystalline properties derived from ethylene chain and amount of CP contained in these fractions is relatively small comparing with the amount of CP contained in fraction 1, approximation of 100 is near in reality, and error in calculation is not almost occurred. Therefore, analysis is carried out provided that B100=100 is defined.

Therefore, according to the following equation (II), CP content can be obtained.

$$CP\ content(\%\ by\ weight)=W40\times A40/B40+W100\times A100/100 \quad (II)$$

That is, the first item of right-hand of equation (II), W40×A40/B40, shows CP content (% by weight) having non-crystallinity, and the second item, W100×A100/100, shows CP content (% by weight) having crystallinity.

Ethylene content in copolymer component can be obtained by the following equation (III) using contents in copolymer components obtained by equation (II).

$$Ethylene\ content(\%\ by\ weight)\ in\ copolymer\ component=(W40\times A40+W100\times A100+W140\times A140)/[contents\ of\ copolymer\ component\ (\%\ by\ weight)] \quad (III)$$

It should be noted that, meaning of determining the fraction temperature of the above-described 3 kinds is as follows.

In CFC analysis relevant to the present invention, 40° C. has a meaning of necessary and sufficient temperature to fractionate only the polymer (for example, most parts of CP, or the component having the extremely low molecular weight in propylene polymer component (PP), and atactic component) having non-crystallinity. 100° C. is the necessary and sufficient temperature to elute only the component which cannot be dissolved at 40° C. but can be dissolved at 100° C. (for example, in CP, component having crystallinity due to the chain of ethylene and/or propylene, and PP having low crystallinity). 140° C. is the necessary and sufficient temperature to elute only the component (for example, the component having particularly high crystallinity in PP, and the component having extremely high molecular weight and extremely high crystallinity of ethylene in CP) which cannot be dissolved at 100° C., but can be dissolved at 140° C., and to recover the total amount of propylene type block-copolymer to be used in analysis.

It should be noted that, W140 does not contain CP component at all, or contains extremely small content of CP even when CP exists, and can be substantially neglected, therefore, it is excluded from calculation of CP content and ethylene content (6) Polymerization Ratio of Ethylene Ethylene content in CP is calculated from the following equation:

Ethylene content in CP(% by weight)=($W40 \times A40 + W100 \times A100$)/[CP]

provided that [CP] is the CP content (% by weight) determined in advance.

The value of ethylene content in CP (% by weight) obtained here is finally converted to mol % by using the molecular weight of ethylene and propylene.

EXAMPLES

Hereinafter, in order to explain the present invention specifically and clearly, the present invention is explained in reference to examples and comparative examples, and rationality and significance and excellence for conventional technology of the constituent features elements of the present invention are verified.

It should be noted that, in the following examples, all of steps for synthesizing complex, steps for synthesizing catalyst and steps for polymerization are carried out under the atmosphere of purified nitrogen, and solvents were used after by deaerating by bubbling with purified nitrogen and after dehydrating.

In addition, measurement of properties, analysis and the like in the examples are subjected to the above-described method and the following method.

(1) Measurement of MFR:

6 g of acetone solution containing thermal stabilizer (BHT) (0.6% by weight) was added to 6 g of polymer.

Then, after the above-described polymer was dried, it was charged into melt-indexer (230° C.), and left under 2.16 Kg of loading for 5 minutes. Then, extruded amount of polymer was measured, and converted to the amount per 10 minutes, this value was defined as MFR (unit: g/10 min).

(2) Measurement of Melting Point™:

By using DSC (TA-2000 type: manufactured by DuPont Co., or DSC-6200 type: manufactured by Seiko-Instruments Inc), after elevating or lowering temperature at the range of 20 to 200° C. by 10° C./min was carried out by one times, melting point was determined by measurement at the second elevating temperature by 10° C./min.

Example 1

Metallocene Complex A

Synthesis of dimethylsilylenebis(2-(2-(5-methylfuryl))-4-phenyl-5-methylindenyl)zirconium dichloride (1-1) Synthesis of 4-phenyl-5-methylindene phenylboronic acid (8.3 g, 68 mmol) was dissolved in ethylene glycol dimethylether (DME, 100 mL), and aqueous solution (100 mL) of cesium carbonate (30 g), 4-bromo-5-methylindene (10 g, 48 mmol), tetrakis(triphenylphosphine) palladium (3.0 g, 2.6 mmol) were sequentially added. Solution was reacted for 55 hours while heating under reflux, then, reaction solution was added into water (200 mL), and extracted with diisopropylether. Organic layer was washed with 1N hydrochloric acid and saturated aqueous solution of sodium chloride, then was dried over sodium sulfate, and solvent was distilled off under reduced pressure to obtain the crude product. This was purified by silica-gel column chromatography (Silica-gel 60: produced by Kanto Chemical Co., Inc, hexane) to obtain 4-phenyl-5-methylindene (8.5 g, yield: 86%) as colorless liquid.

(1-2) Synthesis of 2-bromo-4-phenyl-5-methylindene 4-phenyl-5-methylindene (8.5 g, 41 mmol) was dissolved in dimethylsulfoxide (100 mL), and water (3.7 mL, 206 mmol) was added. N-Bromosuccinimide (9.6 g, 54 mmol) was slowly added, and reaction solution was stirred for 3 hours at room temperature. Reaction solution was poured into water (300 mL), and extracted with toluene, and organic layer was washed with hydrochloric acid and water. To organic layer, p-toluene sulfonic acid monohydrate (1.18 g, 6.2 mmol) was added. After reacting for 3 hours while heating under reflux, the solution was washed with aqueous solution of sodium carbonate and saturated aqueous solution of sodium chloride. After drying organic layer with sodium sulfate, solvent was distilled off under reduced pressure to obtain crude product.

This was purified by silica-gel column chromatography (Silica-gel 60: produced by Kanto Chemical Co., Inc, hexane) to obtain 2-bromo-4-phenyl-5-methylindene (10.4 g, yield: 88%) as pale yellow crystal.

(1-3) Synthesis of 2-(2-(5-methylfuryl))-4-phenyl-5-methylindene 2-methylfuran (4.0 g, 49 mmol) was dissolved in DME (150 mL), and solution of n-butyllithium in n-hexane (29 mL, 1.66 M, 48 mmol) was dropped at −70° C., and reaction solution was stirred for 3 hours. After cooling at −70° C. again, solution of triisopropyl borate (12.5 mL, 54 mmol) in DME (50 mL) was dropped, and reaction solution was stirred overnight while returning to room temperature. To reaction solution, water (50 mL) was added, then, aqueous solution (100 mL) of sodium carbonate (12 g, 109 mmol); tetrakis (triphenylphosphine)palladium (2.5 g, 2.2 mmol); 2-bromo-4-phenyl-5-methylindene (10.4 g, 37 mmol) were sequentially added, and heated at 80° C., and reacted for 3 hours while removing low boiling point substance. Reaction solution was added in water (200 mL), and extracted with diisopropyl ether. Organic layer was washed with 1N hydrochloric acid, saturated aqueous solution of sodium chloride, then, was dried over sodium sulfate, and solvent was distilled off under reduced pressure to obtain the crude product.

This was purified by silica-gel column chromatography (Silica-gel 60: produced by Kanto Chemical Co., Inc, hexane/dichloromethane) to obtain the desired 2-(2-(5-methylfuryl))-4-phenyl-5-methylindene (7.4 g, yield: 71%) as colorless crystal.

(1-4) Synthesis of dimethylbis(2-(2-(5-methylfuryl))-4-phenyl-5-methylindenyl)silane 2-(2-(5-methylfuryl))-4-phenyl-5-methylindene (7.4 g, 26 mmol) was dissolved in tetrahydrofuran (THF, 150 mL), and solution of n-butyllithium in n-hexane (16 mL, 1.66 M, 27 mmol) was dropped at −70° C. After solution was stirred for 2 hours, N-methylimidazole (0.1 mL, 1.2 mmol) was added, and solution of dichlorodimethylsilane (1.7 g, 13 mmol) in THF (30 mL) was dropped, and stirred overnight while increasing temperature gradually. Water (10 mL) was added to reaction solution. Organic layer was washed with 1N hydrochloric acid, saturated aqueous solution of sodium chloride, then, was dried over magnesium sulfate, and solvent was distilled off under reduced pressure to obtain the crude product.

This was purified by silica-gel column chromatography (Silica-gel 60: produced by Kanto Chemical Co., Inc, hexane/dichloromethane) to obtain dimethylbis(2-(2-(5-methylfuryl))-4-phenyl-5-methylindenyl)silane (7.3 g, yield: 89%).

(1-5) Synthesis of dimethylsilylenebis(2-(2-(5-methylfuryl))-4-phenyl-5-methylindenyl)zirconium dichloride Dimethylbis(2-(2-(5-methylfuryl))-4-phenyl-5-methylindenyl)silane (7.3 g, 12 mmol) was dissolved in diethyl ether (250 mL), and solution of n-butyllithium in n-hexane (14 mL, 1.66 M, 23 mmol) was dropped at −76° C. Reaction solution was stirred for 3 hours while increasing the temperature naturally, solvent was distilled off under reduced pressure. Toluene (250 mL), diethyl ether (13 mL) was sequentially added, and cooled at −75° C., and zirconium tetrachloride (2.7 g, 12 mmol) was added. Then, reaction solution was stirred overnight while increasing the temperature naturally. Solvent was distilled off from the obtained reaction solution under reduced pressure.

This was extracted with n-hexane/dichloromethane, and recrystallized to obtain racemic form of dimethylsilylenebis(2-(2-(5-methylfuryl))-4-phenyl-5-methylindenyl)zirconium dichloride (3.9 g, yield: 43%). $^1$H-NMR (400 MHz, CDCl$_3$) δ 1.09 (s, 6H, S$_1$—CH$_3$), 2.24 (s, 6H, Ph-CH$_3$), 2.40 (s, 6H, Furyl-CH$_3$), 2.40 (s, 6H, Ind-5-CH$_3$), 6.04 (d, 2H, Furyl-H), 6.21 (d, 2H, Furyl-H), 6.53 (s, 2H, Ind-H), 6.65 (d, 2H, Ind-H), 6.77 (d, 2H, Ind-H), 7.15-7.69 (br, 8H, Ph-H)

(1-6) Acid Treatment and Salt Treatment of Smectite Group Ion-Exchanging Layered Silicate Acid Treatment:

Into separable flask, distilled water (1130 g) and 96% sulfuric acid (750 g) were added, inner temperature was maintained at 90° C., and Benclay-SL (average particle diameter: 19 μm, 300 g; produced by Mizusawa Industrial chemicals, Ltd) of granulated montmorillonite was added, and solution was reacted for 2 hours. Suspension solution was cooled down to room temperature for 1 hour, and washed with distilled water up to pH 4. Magnification ratio of washing in this case was 1/10000 or less.

Salt Treatment:

In separable flask, lithium sulfate monohydrate (210 g) was dissolved in distilled water (520 g), then, filtered acid treated clay was added thereto, and the slurry solution was stirred for 120 minutes at room temperature. This slurry was filtered, and distilled water (3000 mL) was added to the obtained solid, and stirred for 5 minutes at room temperature. This slurry was filtered. Distilled water (2500 mL) was added to the obtained solid, and stirred for 5 minutes, then, was filtered again. This operation was further repeated 4 times, after the obtained solid was pre-dried for 2 days at 130° C. under nitrogen stream, crude large particles having 53 μm or more of diameter was removed, and further, by drying at 200° C. for 2 hours, chemically treated montmorillonite was obtained.

(1-7) Preparation of Catalyst Used Metallocene Complex A (Catalyst A)

To flask having 1 L of internal volume, montmorillonite (10.0 g) obtained in the above was weighed, and heptane (65 ml), solution of triisobutylaluminum in heptane (35 mL, 25 mmol) were added, and reaction solution was stirred for 1 hour at room temperature. Then, reaction solution was washed with heptane up to 1/100 of residual liquid ratio, finally, amount of slurry was prepared to 100 mL. Solution of triisobutylaluminum in heptane (1.67 mL, 1.2 mmol) was added hereto, and stirred for 10 minutes at room temperature. Further, solution of metallocene complex A (247 mg, 310 μmol) in toluene (60 mL) was added, and stirred for 60 minutes at room temperature.

Next, to the above-described heptane slurry, heptane (340 mL) was added, and introduced to stirred type autoclave having 1 L of internal volume, and propylene was charged for 120 minutes with constant rate of 10 g/hour at 40° C.

After charging propylene, temperature was elevated at 50° C., and maintained for 4 hours at same temperature. Then, residual gas was purged, and slurry of pre-polymerization catalyst was recovered from autoclave. The recovered pre-polymerization catalyst was left standing, and supernatant solution was taken out. To the residual solid, solution of triisobutylaluminum in heptane (8.5 mL, 6.0 mmol) was added at room temperature, and stirred for 10 minutes, then, was dried under reduced pressure to recover 28.8 g of solid catalyst. Magnification ratio of pre-polymerization (value of amount of pre-polymerized polymer divided by the amount of solid catalyst) was 0.42.

(1-8) Propylene-Propylene Ethylene Block Copolymerisation by Catalyst A

The First Step:

After inside of stirred type autoclave having 3 L of internal volume was sufficiently replaced by propylene, solution of triisobutylaluminum in n-heptane (2.76 mL, 2.02 mmol) was added, and hydrogen (300 mL), subsequently liquid propylene (750 g) was introduced, and temperature was elevated up to 65° C., and this temperature was maintained. Catalyst A was made to slurry in n-heptane, and 40 mg (except weight of pre-polymerized polymer) was injected under pressure as catalyst, to start polymerization. Reactor temperature was maintained at 65° C., after passing 1 hour from introduction of catalyst, residual monomer was purged, and the inside of reactor was replaced by argon gas. Stirring was stopped, Teflon (registered trade mark) tube was inserted into the reactor while flowing argon gas, to take out small content of polypropylene. Taking out amount was 8 g.

The Second Step:

Thereafter, propylene and ethylene were introduced up to 1.8 MPa at 60° C. of inner temperature, to attain propylene/ethylene=50/50, and inner temperature was elevated up to 80° C. Thereafter, while introducing the mixed gas prepared in advance of propylene and ethylene, and adjusting inner pressure to 2.0 MPa, polymerization reaction was controlled for 30 minutes.

As a result, 45 g of propylene-propylene•ethylene block copolymer having excellent particle shape was able to obtain. Average gas molar composition in the reactor when polymerizing propylene and ethylene became propylene/ethylene=54/46.

In the above-described block copolymer, from result of CFC-IR, rubber content (CP content) was 18% by weight, ethylene content in rubber (CP) was 34 mol %, and weight average molecular weight in CP part (Mw) was 508,000. In addition, rubber polymerization activity (CP activity) was 340 (g-CP/g-Cat/hr). Tm of propylene homo-polymer collected separately was 156° C., and MFR was 94 (dg/min).

Example 2

Metallocene Complex B

Synthesis of dimethylsilylenebis(2-(2-(5-methylfuryl))-4-(4-t-butylphenyl)-5-methylindenyl)zirconium dichloride (2-1) Synthesis of 4-(4-t-butylphenyl)-5-methylindene 4-t-butylphenylboronic acid (25 g, 0.14 mol) was dissolved in DME (250 mL), and aqueous solution (120 mL) of potassium carbonate (60 g), 4-bromo-5-methylindene (25 g, 0.11 mol), tetrakis(triphenylphosphine)palladium (5 g, 4.3 mmol) were sequentially added. Solution was reacted for 30 hours while heating under reflux, then, reaction solution was added to water (300 mL), and extracted with diisopropyl ether. Organic layer was washed with 1N hydrochloric acid, saturated aqueous solution of sodium chloride, then, was dried over sodium sulfate, and solvent was distilled off under reduced pressure to obtain the crude product.

This was purified by silica-gel column chromatography (Silica-gel 60: produced by Kanto Chemical Co., Inc, hexane) to obtain 4-(4-t-butylphenyl)-5-methylindene (24.4 g, yield: 82%) as colorless liquid.

(2-2) Synthesis of 2-bromo-4-(4-t-butylphenyl)-5-methylindene 4-(4-t-butylphenyl)-5-methylindene (24.4 g, 93 mmol) was dissolved in dimethylsulfoxide (300 mL), and water (7.2 mL) was added. N-bromosuccinimide (22 g, 0.12 mol) was slowly added, and reaction solution was stirred for 3 hours at room temperature. Reaction solution was poured into water (500 mL), and extracted with toluene, organic layer was washed with hydrochloric acid and water. To organic layer, p-toluene sulfonic acid monohydrate (2.9 g, 15 mmol) was added. After reacting for 2 hours while heating under reflux, reaction solution was washed with aqueous solution of sodium carbonate and saturated aqueous solution of sodium chloride. After drying organic layer over magnesium sulfate, solvent was distilled off under reduced pressure to obtain the crude product.

This was purified by silica-gel column chromatography (Silica-gel 60: produced by Kanto Chemical Co., Inc, hexane) to obtain 2-bromo-4-(4-t-butylphenyl)-5-methylindene (29.1 g, yield: 92%) as yellow liquid.

(2-3) Synthesis of 2-(2-(5-methylfuryl))-4-(4-t-butylphenyl)-5-methylindene 2-methylfuran (9.1 g, 0.11 mol) was dissolved in DME (300 mL), solution of n-butyllithium in n-hexane (68 mL, 1.63 M, 0.11 mol) was dropped at −70° C. Reaction solution was stirred for 3 hours, after cooling at −70° C. again, solution of triisopropyl borate (28 mL, 0.12 mol) in DME (50 mL) was dropped, and reaction solution was stirred overnight while returning the temperature up to room temperature. To reaction solution, water (50 mL) was added, then, aqueous solution (200 mL) of sodium carbonate (23 g, 0.22 mol); tetrakis (triphenylphosphine)palladium (5 g, 4.3 mmol); 2-bromo-4-(t-t-butylphenyl)-5-methylindene (29.1 g, 85 mmol) were sequentially added, heated at 80° C., and reacted for 3 hours while removing low boiling point substance. Reaction solution was added in water (200 mL), and extracted with diisopropyl ether. Organic layer was washed with 1N hydrochloric acid, saturated aqueous solution of sodium chloride, then, was dried over sodium sulfate, and solvent was distilled off under reduced pressure to obtain the crude product.

This was purified by silica-gel column chromatography (Silica-gel 60: produced by Kanto Chemical Co., Inc, hexane/dichloromethane) to obtain the desired 2-(2-(5-methylfuryl))-4-(4-t-butylphenyl)-5-methylindene (23.5 g, yield: 81%) as colorless crystal.

(2-4) Synthesis of dimethylbis(2-(2-(5-methylfuryl))-4-(4-t-butylphenyl)-5-methylindenyl)silane 2-(2-(5-methylfuryl))-4-(4-t-butylphenyl)-5-methylindene (15 g, 44 mmol) was dissolved in THF (200 mL), solution of n-butyllithium in n-hexane (27 mL, 1.66 M, 45 mmol) was dropped at −70° C. After reaction solution was stirred for 2 hours, N-methylimidazol (0.2 mL, 2.4 mmol) was added, solution of dichlorodimethylsilane (2.8 g, 22 mmol) in THF (30 mL) was dropped at −70° C., reaction solution was stirred overnight while elevating temperature gradually. Water (10 mL) was added to reaction solution. Organic layer was washed with 1N hydrochloric acid, saturated aqueous solution of sodium chloride, then, was dried over magnesium sulfate, and solvent was distilled off under reduced pressure to obtain the crude product. This was purified by silica-gel column chromatography (Silica-gel 60: produced by Kanto Chemical Co., Inc, hexane/dichloromethane) to obtain dimethylbis(2-(2-(5-methylfuryl))-4-(4-t-butylphenyl)-5-methylindenyl)silane (16.0 g, yield: 99%).

(2-5) Synthesis of dimethylsilylenebis(2-(2-(5-methylfuryl))-4-(4-t-butylphenyl)-5-methylindenyl)zirconium dichloride Dimethylbis(2-(2-(5-methylfuryl))-4-(4-t-butylphenyl)-5-methylindenyl)silane (16.0 g, 22 mmol) was dissolved in diethyl ether (300 mL), solution of n-butyllithium in n-hexane (26 mL, 1.66 M, 43 mmol) was dropped at −76° C. Reaction solution was stirred for 3 hours while elevating temperature naturally, solvent was distilled off under reduced pressure. Toluene (300 mL), diethyl ether (20 mL) were sequentially added, and cooled at −75° C., and zirconium tetrachloride (5.0 g, 22 mmol) was added. Then, reaction solution was stirred overnight while elevating temperature naturally. Solvent was distilled off from the obtained reaction solution under reduced pressure.

This was extracted with n-hexane/dichloromethane and recrystallized, and racemic form of dimethylsilylenebis(2-(2-(5-methylfuryl))-4-(4-t-butylphenyl)-5-methylindenyl)zirconium dichloride (9.0 g, yield: 46%) was obtained.

$^1$H-NMR (400 MHz, CDCl$_3$) δ 1.07 (s, 6H, Si—CH$_3$), 1.34 (s, 18H, C—(CH$_3$)$_3$), 2.27 (s, 6H, Furyl-CH$_3$), 2.39 (s, 6H, Ind-5-CH$_3$), 6.03 (d, 2H, Furyl-H), 6.22 (d, 2H, Furyl-H), 6.60 (s, 2H, Ind-H), 6.65 (d, 2H, Ind-H), 6.76 (d, 2H, Ind-H), 7.10-7.63 (br, 8H, Ph-H)

(2-6) Preparation of Catalyst using Metallocene Complex B (Catalyst B)

Catalyst B was obtained by the same operation as the preparation of catalyst described in [Example 1](1-7) except that 264 mg (293 µmol) of metallocene complex B was used instead of metallocene complex A.

Magnification ratio of pre-polymerization in this case (value of amount of pre-polymerization polymer divided by amount of solid catalyst) was 1.81.

(2-7) Propylene-propylene ethylene block copolymerization by catalyst B 30 mg of catalyst B was used instead of catalyst A, and the same operation as [Example 1](1-8) was carried out. The average gas molar composition in reactor when polymerizing propylene/ethylene in the second step, became propylene/ethylene=54/46. As a result, 110 g of propylene-propylene•ethylene block copolymer was obtained.

From the result of CFC-IR, the block copolymer obtained in the above had 13% by weight of rubber content (CP content), 32 mol % of ethylene content in rubber (CP), and 507,000 of weight average molecular weight in CP part (Mw). In addition, rubber polymerization activity (CP activity) was 500 (g-CP/g-Cat/hr). Tm of the propylene homo-polymer collected separately was 156° C., and MFR was 25 (dg/min).

(2-8) Propylene-propylene•ethylene Block Copolymerization by Catalyst B

The same operation as [Example 1](1-8) was carried out except that 30 mg of catalyst B was used instead of catalyst A, and hydrogen (15 mL) was added when polymerizing in the second step. The average gas molar composition in reactor when polymerizing propylene/ethylene became propylene/ethylene=53/47. As a result, 282 g of propylene-propylene•ethylene block copolymer was obtained.

From the result of CFC-IR, the block copolymer obtained in the above had 62% by weight of rubber content (CP content), 28 mol % of ethylene content in rubber (CP), and 483,000 of weight average molecular weight in CP part (Mw). In addition, rubber polymerization activity (CP activity) was 6700 (g-CP/g-Cat/hr). Tm of the propylene homo-polymer collected separately was 156° C., and MFR was 29 (dg/min).

(2-9) Propylene-Propylene Ethylene Block Copolymerization by Catalyst B

The same operation as [Example 1](1-8) was carried out except that 30 mg of catalyst B was used instead of catalyst A, and the average gas molar composition in reactor was adjusted so as to be propylene/ethylene=32/68 when polymerizing propylene/ethylene. As a result, 170 g of propylene-propylene•ethylene block copolymer was obtained.

From the result of CFC-IR, the block copolymer obtained in the above had 24% by weight of rubber content (CP content), 51 mol % of ethylene content in rubber (CP), and 778,000 of weight average molecular weight in CP part (Mw). In addition, rubber polymerization activity (CP activity) was 1600 (g-CP/g-Cat/hr). Tm of the other collected propylene homo-polymer was 156° C., and MFR was 23 (dg/min).

Example 3

Metallocene Complex C

Synthesis of dimethylsilylenebis(2-(2-(5-methylfuryl))-4-(3-t-butylphenyl)-5-methylindenyl)zirconium dichloride (3-1) Synthesis of 4-(3-t-butylphenyl)-5-methylindene 3-t-butylphenylboronic acid (10 g, 56.2 mmol) was dissolved in dimethoxyethane (150 mL), and aqueous solution (100 mL) of cesium carbonate (24.3 g, 74.6 mmol), 4-bromo-5-methylindene (7.8 g, 37.3 mmol), tetrakis(triphenylphosphine)palladium (1.7 g) were sequentially added. After solution was reacted for 26 hours while heating under reflux, reaction solution was poured into 1N hydrochloric acid-ice water, and extracted with diethyl ether after stirring. Organic layer was washed with saturated aqueous solution of sodium chloride, and dried over magnesium sulfate, then solvent was distilled off under reduced pressure to obtain the crude product.

This was purified by silica-gel column chromatography to obtain the desired 4-(3-t-butylphenyl)-5-methylindene (7.1 g, yield: 73%).

(3-2) Synthesis of 2-bromo-4-(3-t-butylphenyl)-5-methylindene

The obtained 4-(3-t-butylphenyl)-5-methylindene (7.1 g, 27.1 mmol) was dissolved in dimethylsulfoxide (100 mL), and water (2 mL) was added. N-Bromosuccinimide (6.3 g, 35.4 mmol) was added at 0° C., and reaction solution was stirred for 2.5 hours at room temperature, and quenched by adding water on ice bath, and organic layer was extracted by adding toluene. To organic layer, p-toluene sulfonic acid monohydrate (0.5 g) was added. After reacting for 2 hours while heating under reflux, water was added to reaction solution to separate organic layer. Organic layer was washed with saturated aqueous solution of sodium chloride, and dried over magnesium sulfate, then solvent was distilled off under reduced pressure to obtain the crude product.

This was purified by silica-gel column chromatography to obtain the desired 2-bromo-4-(3-t-butylphenyl)-5-methylindene (8.6 g, yield 93%).

(3-3) Synthesis of 2-{2-(5-methylfuryl)}-4-(3-t-butylphenyl)-5-methylindene 2-methylfuran (3.1 g, 37.8 mmol) was dissolved in dimethoxyethane (40 mL), and solution of n-butyllithium in n-hexane (1.65 M, 22.9 mL) was dropped at −76° C., and after reaction solution was stirred for 3 hours, temperature was elevated up to −50° C., triisopropyl borate (9.3 mL, 40 mmol) was dropped, and reaction solution was stirred for 16 hours at room temperature. Water (5 mL) was added, and reaction solution was stirred for 1 hour. Then, aqueous solution (70 mL) of sodium carbonate (5.3 g, 50 mmol), solution of 2-bromo-4-(3-t-butylphenyl)-5-methylindene (8.6 g, 25.2 mmol) dissolved in dimethoxyethane (40 mL), tetrakis(triphenylphosphine)palladium (0.6 g) were sequentially added, and reacted for 3 hours while heating under reflux. Water was added to the reaction solution to separate organic layer, and organic layer was washed with saturated aqueous solution of sodium chloride, and dried over magnesium sulfate, then solvent was distilled off under reduced pressure.

The obtained crude product was purified by silica-gel column chromatography to obtain the desired 2-{2-(5-methylfuryl)}-4-(3-t-butylphenyl)-5-methylindene (4.0 g, yield: 46%).

(3-4) Synthesis of dimethylbis[2-{2-(2-(5-methylfuryl)}-4-(3-t-butylphenyl)-5-methylindenyl]silane The obtained 2-{2-(5-methylfuryl)}-4-(3-t-butylphenyl)-5-methylindene (4.0 g, 11.7 mmol) was dissolved in tetrahydrofuran (50 mL), and solution of n-butyllithium in hexane (1.65 M, 7.1 mL) was dropped at −76° C. After elevating temperature up to room temperature, reaction solution was stirred for 3 hours, N-methylimidazole (0.02 mL) was added, and dichlorodimethylsilane (0.7 mL, 5.8 mmol) was dropped at −76° C. Reaction solution was stirred for 2 hours at room temperature, and water was added to separate organic layer. Organic layer was washed with saturated aqueous solution of sodium chloride, and dried over magnesium sulfate, then solvent was distilled off under reduced pressure to obtain the crude product.

This was purified by silica-gel column chromatography to obtain the desired dimethylbis[2-{2-(5-methylfuryl)}-4-(3-t-butylphenyl)-5-methylindenyl]silane (3.1 g, yield: 72%).

(3-5) Synthesis of dimethylsilylenebis[2-{2-(5-methylfuryl)}-4-(3-t-butylphenyl)-5-methylindenyl]zirconium dichloride The obtained dimethylbis[2-{2-(5-methylfuryl)}-4-(3-t-butylphenyl)-5-methylindenyl]silane (3.1 g, 4.2 mmol) was dissolved in diethyl ether (120 mL), solution of n-butyllithium in n-hexane (1.65 M, 5.1 mL) was dropped at −76° C. After stirring for 2 hours at room temperature, solvent was distilled off under reduced pressure. Diethyl ether (6 mL), toluene (120 mL) were sequentially added, and reaction solution was cooled at −50° C., zirconium tetrachloride (1.0 g, 4.2 mmol) was added. Reaction solution was immediately elevated up to room temperature, and stirred for 2 hours. The obtained reaction solution was once concentrated, extracted with toluene, and concentrated again to dryness.

This was sequentially washed with n-hexane, mixed solvent of n-hexane-diethyl ether, and extracted with toluene to obtain racemic form of the desired dimethylsilylenebis[2-{2-(5-methylfuryl)}-4-(3-t-butylphenyl)-5-methylindenyl]zirconium dichloride (0.8 g).

$^1$H-NMR (400 MHz, CDCl$_3$, rac-isomer).1.08 (s, 6H, Si(CH$_3$)$_2$), 1.32 (s, 18H, tBu), 2.25 (s, 6H, Furyl-CH$_3$), 2.39 (s, 6H, Indenyl-5-CH$_3$), 6.02 (d, 2H, Furyl-H), 6.20 (d, 2H, Furyl-H), 6.51 (s, 2H, Cp-H), 6.6-7.6 (m, 10H, arm), 7.81 (s, 2H, Ph-H).

(3-6) Preparation of Catalyst Using Metallocene Complex C(Catalyst C)

To the flask having 1 L of internal volume, the chemically treated montmorillonite (5.0 g) obtained in the above was weighed, and heptane (32 ml) and solution of triisobutylaluminum in heptane (17.5 mL, 12.5 mmol) were added, and reaction solution was stirred for 1 hour at room temperature. Then, reaction solution was washed with heptane to obtain 1/100 of residual liquid ratio, finally, amount of slurry was prepared to 50 mL. Solution of triisobutylaluminum in heptane (1.0 mL) was added thereto, and stirred for 10 minutes at room temperature. Further, solution of metallocene complex C (75 mg, 75 μmol) in toluene (30 mL) was added, and stirred for 60 minutes at room temperature.

Next, to the above-described heptane slurry, heptane (270 mL) was added, and introduced to stirred type autoclave having 1 L of internal volume, and propylene was charged for 120 minutes by constant rate of 5 g/hour at 40° C.

After charging propylene, temperature was elevated at 50° C., and maintained for 4 hours at same temperature. Then, residual gas was purged, and slurry of pre-polymerization catalyst was recovered from autoclave. The recovered pre-polymerization catalyst was left standing, and supernatant solution was taken out. To the residual solid, solution of triisobutylaluminum in heptane (4.3 mL) was added at room temperature, and stirred for 10 minutes, then, was dried under reduced pressure to recover solid catalyst. Magnification ratio of pre-polymerization (value of amount of pre-polymerized polymer divided by the amount of solid catalyst) was 1.85.

(3-7) Propylene-propylene•ethylene Block Copolymerization by Catalyst C 50 mg of catalyst C was used instead of catalyst A, and operation similar to [Example 1](1-8) was carried out. The average gas molar composition in reactor became propylene/ethylene=45/55 when polymerizing propylene/ethylene in the second step. As a result, 61 g of propylene-propylene•ethylene block copolymer was obtained.

From the result of CFC-IR, block copolymer obtained in the above had 13% by weight of rubber content (CP content), 38 mol % of ethylene content in rubber (CP), and 430,000 of weight average molecular weight in CP part (Mw). In addition, rubber polymerization activity (CP activity) was 320 (g-CP/g-Cat/hr). Tm of the propylene homo-polymer collected separately was 155° C., and MFR was 81 (dg/min).

Example 4

Metallocene Complex D

Synthesis of dimethylsilylenebis(2-(2-(5-methylfuryl))-4-(2-methylphenyl)-5-methylindenyl)zirconium dichloride (4-1) Synthesis of 2-bromo-4-(2-methylphenyl)-5-methylindene 2-methyl-phenylboronic acid (7.61 g, 56.0 mmol) was dissolved in dimethoxyethane (250 mL), and aqueous solution of barium hydroxide octahydrate (0.8 M, 100 mL), 4-bromo-5-methylindene (8.42 g, 40.3 mmol), tetrakis(triphenylphosphine)palladium (1.66 g, 1.44 mmol) were sequentially added. The solution was reacted for 18 hours while heating under reflux, then was washed with hydrochloric acid and water, and organic layer was extracted with diethyl ether. After organic layer was dried over magnesium sulfate, solvent was distilled off under reduced pressure to obtain the crude product.

This was purified by silica-gel column chromatography to obtain the desired 4-(2-methylphenyl)-5-methylindene (6.53 g, 29.6 mmol).

(4-2) Synthesis of 2-bromo-4-(2-methylphenyl)-5-methylindene

The obtained 4-(2-methylphenyl)-5-methylindene (6.53 g, 29.6 mmol) was dissolved in dimethylsulfoxide (75 mL), and water (2.20 mL, 122 mmol) was added. N-bromosuccinimide (6.85 g, 38.5 mmol) was added at 5° C., and reaction solution was stirred for 13 hours at room temperature after elevating temperature naturally. Reaction solution was slowly added to mixed solvent of toluene and water at 5° C., then, aqueous phase was separated. After organic layer was washed with hydrochloric acid and water to remove aqueous phase, p-toluenesulfonic acid monohydrate (0.88 g, 4.63 mmol) was added. After reacting for 2 hours while heating under reflux, reaction solution was washed with aqueous solution of sodium hydroxide and water, and organic layer was extracted with diethyl ether. Organic layer was dried over magnesium sulfate, then, solvent was distilled off under reduced pressure to obtain the crude product.

This was purified by silica-gel column chromatography to obtain the desired 2-bromo-4-(2-methylphenyl)-5-methylindene (7.44 g, 24.9 mmol).

(4-3) Synthesis of 2-(2-(5-methylfuryl))-4-(2-methylphenyl)-5-methylindene

2-Methylfuran (3.20 mL, 35.7 mmol) was dissolved in dimethoxyethane (55 mL), and solution of n-butyllithium in n-hexane (1.66 M, 22.5 mL) was dropped at −73° C. After the temperature was elevated naturally, reaction solution was stirred for 2 hours at room temperature, then, was cooled at −73° C. again, and solution of triisopropyl borate (9.00 mL, 39.1 mmol) dissolved in dimethoxyethane (15 mL) was dropped. After the temperature was elevated naturally, reaction solution was stirred for 2 hours at room temperature, then, water (15.0 mL, 833 mmol) was added, and stirred for 3 hours. Thereafter, aqueous solution of sodium carbonate (1.4 M, 50 mL), 2-bromo-4-(2-methylphenyl)-5-methylindene (7.44 g, 24.9 mmol), tetrakis(triphenylphosphine)palladium (1.48 g, 1.28 mmol) were sequentially added, and the solution was reacted for 3 hours while heating under reflux, then, was washed with hydrochloric acid and water, and organic layer was extracted with diethyl ether. After organic layer was dried over magnesium sulfate, solvent was distilled off under reduced pressure to obtain the crude product.

This was purified by silica-gel column chromatography to obtain the desired 2-(2-(5-methylfuryl))-4-(2-methylphenyl)-5-methylindene (5.39 g, 17.9 mmol).

(4-4) Synthesis of dimethylbis{2-(2-(5-methylfuryl))-4-(2-methylphenyl)-5-methylindenyl}silane The obtained 2-(2-(5-methylfuryl))-4-(2-methylphenyl)-5-methylindene (5.39 g, 17.9 mmol) was dissolved in tetrahydrofuran (90 mL), and solution of n-butyllithium in n-hexane (1.66 M, 11.4 mL) was dropped at −75° C. After elevating temperature naturally, reaction solution was stirred for 2 hours at room temperature, then, N-methylimidazol (75.0 μL, 0.941 mmol) was added, and solution of dichlorodimethylsilane (1.10 mL, 9.03 mmol) dissolved in tetrahydrofuran (12 mL) was dropped at −76° C. After elevating temperature naturally, reaction solution was stirred for 17 hours at room temperature, and water (5.50 mL, 305 mmol) was added to remove aqueous layer. After organic layer was dried over magnesium sulfate, solvent was distilled off under reduced pressure to obtain the crude product.

This was purified by silica-gel column chromatography to obtain the desired dimethylbis(2-(2-(5-methylfuryl))-4-(2-methylphenyl)-5-methylindenyl)silane (4.17 g, 6.35 mmol).

(4-5) Synthesis of dimethylsilylenebis(2-(2-(5-methylfuryl))-4-(2-methylphenyl)-5-methylindenyl)zirconium dichloride The obtained dimethylbis(2-(2-(5-methylfuryl))-4-(2-methylphenyl)-5-methylindenyl)silane (4.17 g, 6.35 mmol) was dissolved in diethyl ether (150 mL), and solution of n-butyllithium in n-hexane (1.66 M, 8.00 mL) was dropped at −76° C. After elevating temperature naturally, reaction solution was stirred for 2 hours at room temperature, then, solvent was distilled off under reduced pressure. Diethyl ether (7.5 mL), toluene (150 mL) were sequentially added, and cooled at −75° C., and zirconium tetrachloride (1.54 g, 6.61 mmol) was added. After elevating temperature naturally, reaction solution was stirred for 2.5 hours at room temperature. The obtained reaction solution was once concentrated, extracted with toluene, and concentrated to dryness again. This was sequentially washed with n-hexane, diisopropyl ether, diethyl ether, cyclohexane, and further, was sequentially washed with diisopropyl ether, diethyl ether.

As a result, the desired dimethylsilylenebis(2-(2-(5-methylfuryl))-4-(2-methylphenyl)-5-methylindenyl)zirconium dichloride was obtained as a mixture of 2 kinds of racemic forms (rac-A and rac-B), which is considered to be derived from axis asymmetry of substituent located in 4-position of indenyl group (0.528 g; rac-A: rac-B=60:40).

$^1$H-NMR (400 MHz, CDCl$_3$, rac-A) δ 1.09 (s, 6H, Si(CH$_3$)$_2$), 1.85 (s, 6H, Furyl-CH$_3$), 2.10 (s, 6H, Ph-CH$_3$), 2.40 (s, 6H, Ind-5-CH$_3$), 6.05-7.60 (18H, Furyl-H, Ind-H, Ph-H).

$^1$H-NMR (400 MHz, CDCl$_3$, rac-B) 61.04 (s, 3H, Si(CH$_3$)$_2$), 1.12 (s, 3H, Si(CH$_3$)$_2$), 1.83 (s, 3H, Furyl-CH$_3$), 1.85 (s, 3H, Furyl-CH$_3$), 2.08 (s, 3H, Ph-CH$_3$), 2.12 (s, 3H, Ph-CH$_3$), 2.42 (s, 3H, Ind-5-CH$_3$), 2.43 (s, 3H, Ind-5-CH$_3$), 6.05-7.60 (18H, Furyl-H, Ind-H, Ph-H).

(4-6) Preparation of Catalyst Using Metallocene Complex D (Catalyst D)

Catalyst D was obtained by the same operation as the preparation of catalyst described in [Example 3](3-6) except that 75 μmol of metallocene complex D instead of metallocene complex C was used.

Magnification ratio of pre-polymerization in this case (value of amount of pre-polymerized polymer divided by the amount of solid catalyst) was 0.27.

(4-7) Propylene-propylene•ethylene Block Copolymerization by Catalyst D 60 mg of catalyst D instead of catalyst A was used, the operation similar to [Example 1] (1-8) was carried out. The average gas molar composition in reactor became propylene/ethylene=50/50 when polymerizing propylene/ethylene in the second step. As a result, 50 g of propylene-propylene•ethylene block copolymer was obtained.

From the result of CFC-IR, block copolymer obtained in the above had 14% by weight of rubber content (CP content), 50 mol % of ethylene content in rubber (CP), and 476,000 of weight average molecular weight in CP part (Mw). In addition, rubber polymerization activity (CP activity) was 117 (g-CP/g-Cat/hr). Tm of the other collected propylene homo-polymer was 149° C.

Example 5

Metallocene Complex E

Synthesis of dimethylsilylenebis[2-(2-{5-methylfuryl)}-4-(2,5-dimethylphenyl)-5-methylindenyl]zirconium dichloride

(5-1) Synthesis of 4-(2,5-dimethylphenyl)-5-methylindene 2,5-dimethylphenylboronic acid (8.42 g, 56.1 mmol) was dissolved in dimethoxyethane (250 mL), and aqueous solution of barium hydroroxide octahydrate (0.763 M, 100 mL), 4-bromo-5-methylindene (8.48 g, 40.6 mmol), tetrakis(triphenylphosphine)palladium (1.64 g, 1.42 mmol) were sequentially added. After the solution was reacted for 20 hours while heating under reflux, solution was washed with hydrochloric acid and water, and organic layer was extracted with diethyl ether. Organic layer was dried over magnesium sulfate, then, solvent was distilled off under reduced pressure to obtain the crude product.

This was purified by silica-gel column chromatography to obtain the desired 4-(2,5-dimethylphenyl)-5-methylindene (5.29 g, 22.6 mmol).

(5-2) Synthesis of 2-bromo-4-(2,5-dimethylphenyl)-5-methylindene

The obtained 4-(2,5-dimethylphenyl)-5-methylindene (5.29 g, 22.6 mmol) was dissolved in dimethylsulfoxide (50 mL), and water (1.65 mL, 91.6 mmol) was added. N-Bromosuccinimide (5.24 g, 29.4 mmol) was added at 0° C., and reaction solution was stirred for 19 hours at room temperature after elevating temperature naturally. Reaction solution was slowly added to mixed solvent of toluene and water, then, aqueous phase was separated. After organic layer was washed with hydrochloric acid, p-toluenesulfonic acid monohydrate (0.65 g, 3.4 mmol) was added. After reacting for 2 hours while heating under reflux, solution was washed with aqueous solution of sodium hydroxide and water, and organic layer was extracted with diethyl ether. Organic layer was dried over magnesium sulfate, then, solvent was distilled off under reduced pressure to obtain the crude product.

This was purified by silica-gel column chromatography to obtain the desired 2-bromo-4-(2,5-dimethylphenyl)-5-methylindene (6.28 g, 20.0 mmol).

(5-3) Synthesis of 2-{2-(5-methylfuryl)}-4-(2,5-dimethylphenyl)-5-methylindene 2-Methylfuran (2.60 mL, 29.0 mmol) was dissolved in dimethoxyethane (45 mL), and solution of n-butyllithium in n-hexane (1.65 M, 18.20 mL) was dropped at −78° C. After elevating temperature naturally, reaction solution was stirred for 4 hours at room temperature, then, was cooled at −80° C. again, and solution of triisopropyl borate (7.25 mL, 31.5 mmol) dissolved in dimethoxyethane (15 mL) was dropped. After elevating temperature naturally, reaction solution was stirred for 18 hours at room temperature, then, water (12.0 mL, 666 mmol) was added, and stirred for 2 hours. Thereafter, aqueous solution of sodium carbonate (1.44 M, 40 mL), solution of 2-bromo-4-(2,5-dimethylphenyl)-5-methylindene (6.28 g, 20.0 mmol) dissolved in dimethoxyethane (10 mL), tetrakis(triphenylphosphine)palladium (1.17 g, 1.01 mmol) were sequentially added, and the solution was reacted for 5 hours while heating under reflux, then, reaction solution was washed with hydrochloric acid and water, and organic layer was extracted with diethyl ether. After organic layer was dried over magnesium sulfate, solvent was distilled off under reduced pressure to obtain the crude product.

This was purified by silica-gel column chromatography to obtain the desired 2-{2-(5-methylfuryl)}-4-(2,5-dimethylphenyl)-5-methylindene (6.18 g, 19.7 mmol).

(5-4) Synthesis of dimethylbis[2-{2-(5-methylfuryl)}-4-(2,5-dimethylphenyl)-5-methylindenyl]silane The obtained 2-{2-(5-methylfuryl)}-4-(2,5-dimethylphenyl)-5-methylindene (6.18 g, 19.7 mmol) was dissolved in tetrahydrofuran (90 mL), and solution of n-butyllithium in n-hexane (1.65 M, 12.55 mL) was dropped at −81° C. After elevating temperature naturally, reaction solution was stirred for 2 hours at room temperature, then, N-methylimidazole (78.5 µL, 0.985 mmol) was added, and solution of dichlorodimethylsilane (1.20 mL, 9.86 mmol) dissolved in tetrahydrofuran (10 mL) was dropped at −81° C. After elevating temperature naturally, reaction solution was stirred for 19 hours at room temperature, and water (6.00 mL, 333 mmol) was added, aqueous layer was removed. After organic layer was dried over magnesium sulfate, solvent was distilled off to obtain the crude product.

This was purified by silica-gel column chromatography to obtain the desired dimethylbis[2-{2-(5-methylfuryl)}-4-(2,5-dimethylphenyl)-5-methylindenyl]silane (3.75 g, 5.47 mmol).

(5-5) Synthesis of dimethylsilylenebis[2-{2-(5-methylfuryl)}-4-(2,5-dimethylphenyl)-5-methylindenyl]zirconium dichloride The obtained dimethylbis[2-{2-(5-methylfuryl)}-4-(2,5-dimethylphenyl)-5-methylindenyl]silane (3.75 g, 5.47 mmol) was dissolved in diethyl ether (130 mL), and solution of n-butyllithium in n-hexane (1.65 M, 7.00 mL) was dropped at −81° C. After elevating temperature naturally, reaction solution was stirred for 2 hours at room temperature, then, solvent was distilled off under reduced pressure. Diethyl ether (6.5 mL), toluene (130 mL) were sequentially added, and cooled at −75° C., and zirconium tetrachloride (1.29 g, 5.54 mmol) was added. After elevating temperature naturally, reaction solution was stirred for 2 hours at room temperature. The obtained reaction solution was once concentrated, and extracted with toluene, and concentrated again to dryness. This was sequentially washed with n-hexane, diisopropyl ether, and then, was extracted with cyclohexane. Further, after washing with diethyl ether, reaction solution was extracted with cyclohexane.

Consequently, the desired dimethylsilylenebis[2-{2-(5-methylfuryl)}-4-(2,5-dimethylphenyl)-5-methylindenyl]zirconium dichloride was obtained as a mixture of 2 kinds of racemic forms (rac-A and rac-B), which is considered to be derived from axis asymmetry of substituent located in 4-position of indenyl group (0.37 g; rac-A: rac-B=54:46).

$^1$H-NMR (400 MHz, CDCl$_3$, rac-A) 1.06 (s, 6H, Si(CH$_3$)$_2$), 1.83 (s, 6H, Furyl-CH$_3$), 2.12 (s, 6H, Ph-CH$_3$), 2.34 (s, 6H, Ph-CH$_3$), 2.40 (s, 6H, Indenyl-CH$_3$), 6.05-7.47 (16H, Furyl-H, Indenyl-H, Ph-H).

$^1$H-NMR (400 MHz, CDCl$_3$, rac-B) 1.03 (s, 3H, Si(CH$_3$)$_2$), 1.10 (s, 3H, Si(CH$_3$)$_2$), 1.79 (s, 3H, Furyl-CH$_3$), 1.83 (s, 3H, Furyl-CH$_3$), 2.10 (s, 3H, Ph-CH$_3$), 2.12 (s, 3H, Ph-CH$_3$), 2.20 (s, 3H, Ph-CH$_3$), 2.30 (s, 3H, Ph-CH$_3$), 2.38 (s, 3H, Indenyl-CH$_3$), 2.42 (s, 3H, Indenyl-CH$_3$), 6.05-7.47 (16H, Furyl-H, Indenyl-H, Ph-H).

(5-6) Preparation of Catalyst Using Metallocene Complex E (Catalyst E)

Catalyst E was obtained by the same operation as the preparation of catalyst described in [Example 3](3-6) except that 75 μmol of metallocene complex E was used instead of metallocene complex A.

Magnification ratio of pre-polymerization in this case (value of amount of pre-polymerized polymer divided by the amount of solid catalyst) was 1.35.

(5-7) Propylene-propylene•ethylene Block Copolymerization by Catalyst E 100 mg of catalyst E was used instead of catalyst A, and the operation similar to [Example 1](1-8) was carried out. The average gas molar composition in reactor became propylene/ethylene-48/52 when polymerizing propylene/ethylene in the second step. As a result, 202 g of propylene-propylene•ethylene block copolymer was obtained.

From the result of CFC-IR, block copolymer obtained in the above had 56% by weight of rubber content (CP content), 34 mol % of ethylene content in rubber (CP), and 300,000 of weight average molecular weight in CP part (Mw). In addition, rubber polymerization activity (CP activity) was 2200 (g-CP/g-Cat/hr). Tm of the other collected propylene homopolymer was 153° C.

Example 6

Metallocene Complex F

Synthesis of dimethylsilylenebis(2-(2-(5-methylfuryl))-4-(3,5-dimethylphenyl)-5-methylindenyl)zirconium dichloride (6-1) Synthesis of 4-(3,5-dimethylphenyl)-5-methylindene 3,5-dimethylphenylboronic acid (20 g, 0.13 mol) was dissolved in DME (250 mL), and aqueous solution (140 mL) of cesium carbonate (60 g), 4-bromo-5-methylindene (20 g, 90 mmol), tetrakis(triphenylphosphine)palladium (5 g, 4.3 mmol) were sequentially added. After solution was reacted for 44 hours while heating under reflux, reaction solution was added into water (500 mL), and extracted with diisopropyl ether. Organic layer was washed with 1N hydrochloric acid, saturated aqueous solution of sodium chloride, then, was dried over sodium sulfate, and solvent was distilled off under reduced pressure to obtain the crude product.

This was purified by silica-gel column chromatography (Silica-gel 60, hexane: produced by Kanto Chemical Co., Inc) to obtain 4-(3,5-dimethylphenyl)-5-methylindene (20.4 g, yield: 96%) as colorless liquid.

(6-2) Synthesis of 2-bromo-4-(3,5-dimethylphenyl)-5-methylindene 4-(3,5-dimethylphenyl)-5-methylindene (20.4 g, 87 mmol) was dissolved in dimethylsulfoxide (200 mL), and water (6 mL) was added. N-Bromosuccinimide (20 g, 0.11 mol) was slowly dropped. Reaction solution was stirred for 2 hours at room temperature. Reaction solution was poured into water (500 mL), and extracted with toluene, and organic layer was washed with hydrochloric acid, water. To organic layer, p-toluene sulfonic acid monohydrate (2.5 g, 13 mmol) was added. After reacting for 2 hours while heating under reflux, reaction solution was washed with aqueous solution of sodium carbonate and saturated aqueous solution of sodium chloride. After organic layer was dried over magnesium sulfate, solvent was distilled off under reduced pressure to obtain the crude product.

This was purified by silica-gel column chromatography (Silica-gel 60, hexane: produced by Kanto Chemical Co., Inc) to obtain 2-bromo-4-(3,5-dimethylphenyl)-5-methylindene (26.8 g, yield: 98%) as pale yellow liquid.

(6-3) Synthesis of 2-(2-(5-methylfuryl))-4-(3,5-dimethylphenyl)-5-methylindene 2-methylfuran (10 g, 0.12 mol) was dissolved in DME (200 mL), the solution of n-butyllithium in n-hexane (75 ml, 1.63 M, 1.1 mol) was dropped at −70° C., and reaction solution was stirred for 3 hour. After cooling at −73° C. again, solution of triisopropyl borate (31 mL, 0.13 mol) in dimethoxyethane (60 mL) was dropped, and reaction solution was stirred overnight while returning the temperature to room temperature. Water (50 mL) was added to the reaction solution, then, aqueous solution (150 mL) of sodium carbonate (26 g, 0.25 mol), tetrakis(triphenylphosphine)palladium (5 g, 4.3 mmol), 2-bromo-4-(3,5-dimethylphenyl)-5-methylindene (26.8 g, 0.86 mol) were sequentially added, and reaction solution was heated at 80° C., and reacted for 3 hours while removing low boiling substance. Reaction solution was added to water (400 mL), was extracted with diisopropyl ether. After organic layer was washed with 1N hydrochloric acid, saturated aqueous solution of sodium chloride, organic layer was dried over sodium sulfate, and solvent was distilled off under reduced pressure to obtain the crude product.

This was purified by silica-gel column chromatography (Silica-gel 60, hexane/dichloromethane: produced by Kanto Chemical Co., Inc) to obtain the desired 2-(2-(5-methylfuryl))-4-(3,5-dimethylphenyl)-5-methylindene (24.7 g, yield: 92%) as colorless crystal.

(6-4) Synthesis of dimethylbis(2-(2-(5-methylfuryl))-4-(3,5-dimethylphenyl)-5-methylindenyl)silane 2-(2-(5-methylfuryl))-4-(3,5-dimethylphenyl)-5-methylindene (10.2 g, 32 mmol) was dissolved in THF (150 mL), and solution of n-butyllithium in n-hexane (20 mL, 1.63 M, 33 mmol) was dropped at −70° C. After reaction solution was stirred for 6 hours, N-methylimidazol (0.13 mL, 1.6 mmol) was added, and solution of dichlorodimethylsilane (2.1 g, 16 mmol) in THF (20 mL) was dropped at −70° C., and reaction solution was stirred overnight while elevating temperature slowly. Water (10 mL) was added to the reaction solution, and after organic layer was washed with 1N hydrochloric acid, saturated aqueous solution of sodium chloride, organic layer was dried over magnesium sulfate, solvent was distilled off under reduced pressure to obtain the crude product.

This was purified by silica-gel column chromatography (Silica-gel 60: produced by Kanto Chemical Co., Inc, hexane/dichloromethane) to obtain dimethylbis(2-(2-(5-methylfuryl))-4-(3,5-dimethylphenyl)-5-methylindenyl)silane (8.1 g, yield: 73%).

(6-5) Synthesis of dimethylsilylenebis(2-(2-(5-methylfuryl))-4-(3,5-dimethylphenyl)-5-methylindenyl) zirconium dichloride Dimethylbis(2-(2-(5-methylfuryl))-4-(3,5-dimethylphenyl)-5-methylindenyl)silane (8.1 g, 12 mmol) was dissolved in diethyl ether (300 mL), and solution of n-butyllithium in n-hexane (15 mL, 1.63 M, 25 mmol) was dropped at −76° C. Reaction solution was stirred for 3 hours while elevating temperature naturally, then, and solvent was distilled off under reduced pressure. Toluene (300 mL), diethyl ether (15 mL) were sequentially added, and reaction solution was cooled at −75° C., and zirconium tetrachloride (2.8 g, 12 mmol) was added. Then, reaction solution was stirred overnight while elevating temperature naturally. Solvent was distilled off from the obtained reaction solution.

This was extracted with n-hexane/dichloromethane, and recrystallized to obtain the racemic form of dimethylsilylenebis(2-(2-(5-methylfuryl))-4-(3,5-dimethylphenyl)-5-methylindenyl)zirconium dichloride (2.9 g, yield: 29%) as orange crystal.

$^1$H-NMR (400 MHz, CDCl$_3$) δ 1.06 (s, 6H, Si—CH$_3$), 2.27 (s, 6H, Furyl-CH$_3$), 2.29 (s, 6H, Ph-CH$_3$), 2.35 (s, 6H, Ph-CH$_3$), 2.39 (s, 6H, Ind-5-CH$_3$), 6.03 (d, 2H, Furyl-H), 6.22 (d, 2H, Furyl-H), 6.56 (s, 2H, Ind-H), 6.64 (d, 2H, Ind-H), 6.74 (d, 2H, Ind-H), 6.75 (s, 2H, Ph-H), 6.95 (s, 2H, Ph-H), 7.36 (s, 2H, Ph-H)

(6-6) Preparation of Catalyst Using Metallocene Complex F

The operation similar to [Example 1](1-7) was carried out except that 250 mg (296 μmol) of metallocene complex F was used instead of metallocene complex A to obtain catalyst F.

Magnification ratio of pre-polymerization in this case (value of amount of pre-polymerized polymer divided by the amount of solid catalyst) was 1.75.

(6-7) Propylene-propylene ethylene block copolymerization by catalyst F 30 mg of catalyst F was used instead of catalyst A, the operation similar to [Example 1](1-8) was carried out. The average gas molar composition in reactor became propylene/ethylene=52/48 when polymerizing propylene/ethylene in the second step. As a result, 176 g of propylene-propylene•ethylene block copolymer was obtained.

From the result of CFC-IR, block copolymer obtained in the above had 18% by weight of rubber content (CP content), 37 mol % of ethylene content in rubber (CP), and 607,000 of weight average molecular weight in CP (Mw). In addition, rubber polymerization activity (CP activity) was 1200 (g-CP/g-Cat/hr). Tm of the other collected propylene homo-polymer was 157° C. MFR was 6 (dg/min).

Example 7

Metallocene Complex G

Synthesis of dimethylsilylenebis(2-(5-methyl-2-furyl)-4-(3,5-diisopropylphenyl)-5-methyl-indenyl) zirconium dichloride

(7-1) Synthesis of 4-(3,5-diisopropylphenyl)-5-methylindene 3,5-diisopropylbromobenzene was synthesized by the method according to described in "Eur. J. Org. Chem. 2006, p 2727".

To the solution of 3,5-diisopropylbromobenzene (5.76 g, 23.9 mmol) and tetramethylethylenediamine (3.6 mL, 23.9 mmol) in diethyl ether (30 mL), solution of n-butyllithium in n-hexane (14.5 mL, 23.9 mmol) was dropped at −60° C. Reaction solution was stirred for 1.5 hours at −60° C., and further was stirred for 30 minutes at 0° C., then, solution of triisopropyl borate (6.6 mL) in diethyl ether (5 mL) was dropped at −60° C. Reaction solution was stirred for 30 minutes at −60° C., and further, was stirred overnight at room temperature, then, diluted hydrochloric acid (50 mL) was added. Resulting solid part was filtered to obtain the crude product of 3,5-diisopropylphenylboronic acid (5.9 g).

3,5-diisopropylphenylboronic acid (5.9 g, 23.9 mmol) was added to dimethoxyethane (80 mL) and water (15 mL), cesium carbonate (10 g, 32 mmol), 4-bromo-5-methylindene (3.5 g, 15.9 mmol), tetrakis(triphenylphosphine)palladium (0.55 g, 0.448 mmol) were sequentially added. After reaction solution was intermittently reacted for 28 hours while heating under reflux, solution was washed with diluted hydrochloric acid and water, and organic layer was extracted with diethyl ether. Solvent was distilled off to obtain the crude product (7.3 g).

This was purified by silica-gel column chromatography to obtain the desired 4-(3,5-diisopropylphenyl)-5-methylindene (4.69 g, yield: 100%).

(7-2) Synthesis of 2-bromo-4-(3,5-diisopropylphenyl)-5-methylindene

The obtained 4-(3,5-diisopropylphenyl)-5-methylindene (4.69 g, 15.9 mmol) was dissolved in dimethylsulfoxide (40 mL), and water (1.1 g) was added. N-Bromosuccinimide (NBS)(3.1 g, 17.5 mmol) was added at 5 to 10° C., and after elevating the temperature naturally, reaction solution was stirred for 1 hour at room temperature. Reaction solution was slowly added to mixed solution of toluene and water at room temperature, then, aqueous phase was separated. Organic layer was washed with diluted hydrochloric acid, and after aqueous phase was removed, p-toluene sulfonic acid mono hydrate (0.43 g, 2.3 mmol) was added. After reacting for 1.5 hours while heating under reflux, reaction solution was washed with aqueous solution of sodium hydroxide (1N) and water, and organic layer was extracted. Organic layer was dried over magnesium sulfate, then, solvent was distilled off under reduced pressure to obtain the crude product (5.98 g).

(7-3) Synthesis of 2-(2-(5-methylfuryl))-4-(3,5-diisopropylphenyl)-5-methylindene 2-Methylfuran (1.58 mL, 17.5 mmol) was dissolved in dimethoxyethane (30 mL), and solution of n-butyllithium in n-hexane (10.6 mL, 17.5 mmol) was dropped at −30° C. After elevating the temperature naturally, reaction solution was stirred for 4 hour at room temperature, then, was cooled at −30° C. again, and solution (10 mL) of triisopropyl borate (4.2 mL, 18.3 mmoL) in dimethoxyethane was dropped. Reaction solution was stirred for 1 hour at −30° C., and for 15 hour at room temperature, then, water (20 mL), sodium carbonate (4.3 g, 41.3 mmol), the above-described obtained crude product (5.98 g) of 2-bromo-4-(3,5-diisopropylphenyl)-5-methylindene, tetrakis(triphenylphosphine)palladium (0.55 g, 0.47 mmol) were sequentially added, and solution was reacted for 2 hours while heating under reflux, then, reaction solution was washed with diluted hydrochloric acid, and organic layer was extracted by adding diethyl ether. Organic layer was dried over magnesium sulfate, then, solvent was distilled off under reduced pressure to obtain the crude product.

This was purified by silicagel column chromatography to obtain the desired 2-methylfuryl-4-(3,5-diisopropylphenyl)-5-methylindene (4.06 g, yield: 69%).

(7-4) Synthesis of dimethylbis(2-(2-(5-methylfuryl))-4-(3,5-diisopropylphenyl)-5-methylindenyl) silane The obtained 2-methylfuryl-4-(3,5-diisopropylphenyl)-5-methylindene (1.88 g, 5.07 mmol) was dissolved in tetrahydrofuran (30 mL), and solution of n-butyllithium in n-hexane (3.2 mL, 5.3 mmol) was dropped at −60° C. After reaction solution was stirred for 45 minutes at −60° C. and for 2.5 hours at room temperature, N-methylimidazole (10 μL, 0.13 mmol) was added, at −30° C., dichlorodimethylsilane (0.30 mL, 2.5 mmol) was dropped. Reaction solution was stirred for minutes at −30° C. and for 1 hour at room temperature, and diluted hydrochloric acid was added to separate aqueous layer.

After organic layer was dried over magnesium sulfate, solvent was distilled off under reduced pressure to obtain the desired crude product of dimethylbis{2-methylfuryl-4-(3,5-diisopropylphenyl))-5-methylindenyl}silane (2.0 g).

(7-5) Synthesis of dimethylsilylenebis(2-(2-(5-methylfuryl))-4-(3,5-diisopropylphenyl)-5-methylindenyl) zirconium dichloride The obtained crude product (2.0 g, 2.52 mmol) was dissolved in diethylether (20 mL), and solution of n-butyllithium in n-hexane (3.1 mL, 5.04 mmol) was dropped at −20° C., and after reaction solution was stirred for 30 minutes at −20° C. for 2 hours at room temperature, toluene (80 mL) was added, and cooled at −20° C., and zirconium tetrachloride (0.56 g, 2.39 mmol) was added. After elevating temperature naturally, reaction solution was stirred for 2 hours at room temperature. Soluble part was separated by decantation from the obtained reaction solution, and soluble part and insoluble part were divided.

Solid part obtained by distillation off of solvent was washed with hexane (5 times by 10 mL) to obtain racemic form of the desired dichlorodimethylsilylenebis(2-(5-methyl-2-furyl)-(3,5-diisopropylphenyl)-5-methyl-indenyl)zirconium (778 mg, yield: 30%).

$^1$H-NMR (400 MHz, CDCl$_3$).1.06 (s, 6H, Me2Si), 1.22-1.26 (m, 24H, iPr), 2.29 (s, 6H, CH$_3$), 2.39 (s, 6H, CH$_3$), 2.8-3.0 (m, 4H, CH), 6.01 (s, 2H), 6.21 (s, 2H), 6.58 (s, 2H), 6.65 (d, 2H, J=9 Hz), 6.76 (d, 2H, J=9 Hz), 6.86 (s, 2H), 7.00 (s, 2H), 7.53 (s, 2H).

(7-6) Preparation of Catalyst Using Metallocene Complex G (Catalyst G)

Catalyst G was obtained by the same operation as the preparation of catalyst described in [Example 3](3-6) except that 75 μmol of metallocene complex G instead of metallocene complex C was used.

Magnification ratio of pre-polymerization in this case (value of amount of pre-polymerized polymer divided by the amount of solid catalyst) was 1.35.

(7-7) Propylene-propylene•ethylene Block Copolymerization by Catalyst G 100 mg of catalyst G was used instead of catalyst A, and the operation similar to [Example 1](1-8) was carried out. The average gas molar composition in reactor became propylene/ethylene-51/49 when polymerizing propylene/ethylene in the second step. As a result, 143 g of propylene-propylene•ethylene block copolymer was obtained.

From the result of CFC-IR, block copolymer obtained in the above had 22% by weight of rubber content (CP content), 34 mol % of ethylene content in rubber (CP), and 520,000 of weight average molecular weight in CP (Mw). In addition, rubber polymerization activity (CP activity) was 600 (g-CP/g-Cat/hr). Tm of the other collected propylene homo-polymer was 154° C.

Example 8

Metallocene Complex H

Synthesis of dimethylsilylenebis[2-{2-(5-methylfuryl)}-4-(3,5-di-t-butylphenyl)-5-methylindenyl]zirconium dichloride

(8-1) Synthesis of 4-(3,5-di-t-butylphenyl)-5-methylindene 1-bromo-3,5-di-t-butylbenzene (15 g, 158 mmol) was dissolved in diethyl ether (200 mL), and cooled at −30° C., and solution of n-butyllithium in hexane (1.65 M, 35 mL) was dropped, and reaction solution was stirred for 2 hours after elevating the temperature up to room temperature. After reaction solution was cooled at −72° C. again, triisopropyl borate (17.3 mL, 75 mmol) was dropped, and reaction solution was stirred for 16 hours at room temperature. Water (5 mL) was added, and reaction solution was stirred for 3 hours to separate organic layer, and organic layer was washed with saturated solution of sodium chloride, and dried over magnesium sulfate, then, solvent was distilled off under reduced pressure. The obtained white crystal (12.5 g) was dissolved in dimethoxyethane (100 mL), and aqueous solution (100 mL) of cesium carbonate (23 g, 71 mmol), 4-bromo-5-methylindene (7.4 g, 35 mmol), tetrakis(triphenylphosphine)palladium (1.6 g) were sequentially added. Solution was reacted for hours while heating under reflux, then, reaction solution was poured to 1N hydrochloric acid-ice water, and after stirring, organic layer was separated. Organic layer was washed with saturated solution of sodium chloride, and dried over magnesium sulfate, then, solvent was distilled off under reduced pressure to obtain the crude product.

This was purified by silica-gel column chromatography to obtain the desired 4-(3,5-di-t-butylphenyl)-5-methylindene (7.2 g, yield: 64%).

(8-2) Synthesis of 2-bromo-4-(3,5-di-t-butylphenyl)-5-methylindene

The obtained 4-(3,5-di-t-butylphenyl)-5-methylindene (7.2 g, 22.6 mmol) was dissolved in dimethoxyethane (100 mL), and water (3 mL) was added. N-bromosuccinimide (6.0 g, 33.7 mmol) was added at 0° C., and reaction solution was stirred for 2 hours at room temperature. Water was added on ice bath to quench, and reaction solution was extracted with diethyl ether. Organic layer was washed with saturated solution of sodium chloride, and dried over magnesium sulfate, and solvent was distilled off under reduced pressure. Toluene (100 mL) and p-toluenesulfonic acid monohydrate (0.5 g) was added thereto, and solution was reacted for 1 hour while heating under reflux. Water was added to the reaction solution to separate organic layer, and washed with saturated solution of sodium chloride, and dried over magnesium sulfate, then, solvent was distilled off under reduced pressure to obtain the crude product.

This was purified by silica-gel column chromatography to obtain the desired 2-bromo-4-(3,5-di-t-butylphenyl)-5-methylindene (5.0 g, yield: 56%).

(8-3) Synthesis of 2-{2-(5-methylfuryl)}-4-(3,5-di-t-butylphenyl)-5-methylindene 2-Methylfuran (3.7 g, 45 mmol) was dissolved in dimethoxyethane (50 mL), and solution of n-butyllithium in hexane (1.65 M, 27 mL) was dropped at −76° C., and reaction solution was stirred for 2 hours while elevating the temperature slowly, then, was cooled at −50° C., and triisopropyl borate (11 mL, 49 mmol) was dropped, and reaction solution was stirred for 16 hours at room temperature. Water (10 mL) was added, and reaction solution was stirred for 1 hour. Thereafter, aqueous solution (50 mL) of sodium carbonate (4.0 g, 38 mmol), solution of 2-bromo-4-(3,5-di-t-butylphenyl)-5-methylindene (7.5 g, 18.9 mmol) dissolved in dimethoxyethane (40 mL), tetrakis(triphenylphosphine)palladium (0.5 g) were sequentially added, and solution was reacted for 3 hours while heating under reflux. Water was added to the reaction solution to separate organic layer, and washed with saturated solution of sodium chloride, was dried over magnesium sulfate, then, solvent was distilled off under reduced pressure.

The obtained the crude product was purified by silica-gel column chromatography to obtain the desired 2-{2-(5-methylfuryl)}-4-(3,5-di-t-butylphenyl)-5-methylindene (5.4 g, yield: 72%).

(8-4) Synthesis of dimethylbis[2-{2-(5-methylfuryl)}-4-(3,5-di-t-butylphenyl)-5-methylindenyl]silane The obtained 2-{2-(5-methylfuryl)}-4-(3,5-di-t-butylphenyl)-5-methylindene (5.4 g, 13.6 mmol) was dissolved in tetrahydrofuran (60 mL), and solution of n-butyllithium in hexane (1.57 M, 8.7 mL) was dropped at −76° C. Reaction solution was stirred for 3 hours after elevating temperature up to room temperature, then, N-methylimidazole (0.02 mL) was added, and dichlorodimethylsilane (0.8 mL, 6.8 mmol) was added at −76° C. Reaction solution was stirred for 2 hours at room temperature, and water was added to separate organic layer. Organic layer was washed with saturated solution of sodium chloride, and dried over magnesium sulfate, then, solvent was distilled off under reduced pressure to obtain the desired crude product (5.8 g) of dimethylbis[2-{2-(5-methylfuryl)}-4-(3,5-di-t-butylphenyl)-5-methylindenyl]silane.

(8-5) Synthesis of dimethylsilylenebis[2-{2-(5-methylfuryl)}-4-(3,5-di-t-butylphenyl)-5-methylindenyl]zirconium dichloride Crude product (5.8 g) of the obtained dimethylbis[2-{2-(5-methylfuryl)}-4-(3,5-di-t-butylphenyl)-5-methylindenyl]silane) was dissolved in diethyl ether (150 mL), and solution of n-butyllithium in n-hexane (1.57 M, 8.7 mL) was dropped at −76° C. Reaction solution was stirred for 2 hours at room temperature, then, solvent was removed under reduced pressure. Diethyl ether (6 mL), toluene (120 mL) were sequentially added, and reaction solution was cooled at −50° C., and zirconium tetrachloride (1.6 g, 6.8 mmol) was added. After elevating temperature up to room temperature immediately, solution was stirred for 2.5 hours. The obtained reaction solution was once concentrated, and extracted with toluene, and concentrated again to dryness.

This was washed with n-hexane, then, was recrystallized with diethyl ether to obtain racemic form (1.0 g) of the desired dimethylsilylenebis[2-{2-(5-methylfuryl)}-4-(3,5-di-t-butylphenyl)-5-methylindenyl]zirconium dichloride.

$^1$H-NMR (400 MHz, CDCl$_3$, rac isomer) 1.07 (s, 6H, Si(CH$_3$)$_2$), 1.29 (s, 18H, tBu), 1.31 (s, 18H, tBu), 2.27 (s, 6H, Furyl-CH$_3$), 2.39 (s, 6H, Indenyl-5-CH$_3$), 6.02 (dd, 2H, Furyl-H), 6.21 (d, 2H, Furyl-H), 6.58 (s, 2H, Cp-H), 6.66 (d, 2H, Indenyl-H), 6.77 (d, 2H, Indenyl-H), 6.99 (s, 2H, Ph-H), 7.3-7.7 (m, 2H, Ph-H).

(8-6) Preparation of Catalyst Using Metallocene Complex H(Catalyst H)

Catalyst H was obtained by the same operation as the preparation of catalyst described in [Example 3](3-6) except that 75 μmol of metallocene complex H instead of metallocene complex C was used.

Magnification ratio of pre-polymerization in this case (value of amount of pre-polymerized polymer divided by the amount of solid catalyst) was 0.39.

(8-7) Propylene-propylene•ethylene Block Copolymerization by Catalyst H 100 mg of catalyst H was used instead of catalyst A, and the operation similar to [Example 1](1-8) was carried out. The average gas molar composition in reactor became propylene/ethylene=51/49 when polymerizing propylene/ethylene in the second step. As a result, 104 g of propylene-propylene•ethylene block copolymer was obtained.

From the result of CFC-IR, block copolymer obtained in the above had 12% by weight of rubber content (CP content), 33 mol % of ethylene content in rubber (CP), and 540,000 of weight average molecular weight in CP (Mw). In addition, rubber polymerization activity (CP activity) was 250 (g-CP/g-Cat/hr). Tm of the other collected propylene homo-polymer was 153° C.

Example 9

Metallocene Complex I

Synthesis of dimethylsilylenebis[2-{2-(5-methylfuryl)}-4-{2-methyl-4-(t-butyl)phenyl}-5-methylindenyl]zirconium dichloride (9-1) Synthesis of (9-1)1-(t-butyl)-3-methylbenzene 1-Bromo-3-(t-butyl)benzene (20.26 g, 95.1 mmol) was dissolved in diethyl ether (200 mL), {1,1'-bis(diphenylphosphino)ferrocenyl}nickel dichloride (1.00 g, 1.46 mmol) was added. Solution of methylmagnesium bromide in diethyl ether (3.00 M, 35.00 mL) was dropped at −85° C., and after elevating temperature naturally, reaction solution was stirred for 1 hour at −5° C., and water (30 mL) was added. Solution was washed with hydrochloric acid and water, and organic layer was extracted with diethyl ether. Organic layer was dried over magnesium sulfate, then, solvent was distilled off to obtain the crude product.

This was purified by silica-gel column chromatography to obtain the desired 1-(t-butyl)-3-methylbenzene (13.58 g, 91.6 mmol).

(9-2) Synthesis of 1-bromo-2-methyl-4-(t-butyl)benzene

The obtained 1-(t-butyl)-3-methylbenzene (13.58 g, 91.6 mmol) was dissolved in carbon tetrachloride (15 mL), and iron powder (0.0617 g, 1.10 mmol) was added. After cooling at −5° C., solution of bromine (5.10 mL, 99.5 mmol) dissolved in carbon tetrachloride (15 mL) was dropped, then, reaction solution was stirred for 1 hour. Reaction solution was added to ice water, and after removing aqueous layer, organic layer was dried over magnesium sulfate, and solvent was distilled off under reduced to obtain the crude product.

This was purified by distillation under reduced pressure to obtain the desired 1-bromo-2-methyl-4-(t-butyl)benzene (10.70 g, 47.1 mmol).

(9-3) Synthesis of 2-methyl-4-(t-butyl)phenylboronic acid

The obtained 1-bromo-2-methyl-4-(t-butyl)benzene (10.70 g, 47.1 mmol) was dissolved in tetrahydrofuran (50 mL). After cooling at −5° C., solution of n-butyllithium in n-hexane (1.65 M, 31.40 mL) was dropped, and reaction solution was stirred for 1 hour, then, triisopropyl borate (14.10 mL, 61.3 mmol) was dropped, and stirred for 1 hour. Temperature was elevated up to room temperature, then, reaction solution was stirred for 1 hour, then, hydrochloric acid (0.5 M, 30 mL) was added, and reaction solution was stirred for 3 hours. Resulting solid was filtered, and dried under reduced pressure to obtain the desired 2-methyl-4-(t-butyl) phenylboronic acid (7.00 g, 36.4 mmol).

(9-4) Synthesis of 4-{2-methyl-4-(t-butyl)phenyl}-5-methylindene

The obtained 2-methyl-4-(t-butyl)phenylboronic acid (7.00 g, 36.4 mmol) was dissolved in dimethoxyethane (150 mL), and aqueous solution of cesium carbonate (0.988 M, 50 mL), 4-bromo-5-methylindene (5.48 g, 26.2 mmol), tetrakis (triphenylphosphine)palladium (1.05 g, 0.910 mmol) were sequentially added. After solution was reacted for 18 hours while heating under reflux, then, was washed with hydrochloric acid and water, and organic layer was extracted with diethyl ether. After organic layer was dried magnesium sulfate, solvent was distilled off under reduced pressure to obtain the crude product.

This was purified by silica-gel column chromatography to obtain the desired 4-{2-methyl-4-(t-butyl)phenyl}-5-methylindene (5.64 g, 20.4 mmol).

(9-5) Synthesis of 2-bromo-4-{2-methyl-4-(t-butyl) phenyl}-5-methylindene

The obtained 4-{2-methyl-4-(t-butyl)phenyl}-5-methylindene (5.64 g, 20.4 mmol) was dissolved in dimethylsulfoxide (150 mL), and water (1.50 mL, 83.2 mmol) was added. N-Bromosuccinimide (4.73 g, 26.6 mmol) was added at 15° C., after elevating temperature naturally, reaction solution was stirred for 92 hours at room temperature. N-Bromosuccinimide (0.36 g, 2.0 mmol) was added again at 15° C., after elevating temperature naturally, reaction solution was stirred for 2 hours at room temperature. Further, N-bromosuccinimide (0.72 g, 4.0 mmol) was added at 15° C., and after elevating temperature naturally, reaction solution was stirred for 2 hours at room temperature. Reaction solution was slowly added to mixed solution of toluene and water at 2° C., then, aqueous phase was separated. p-Toluenesulfonic acid monohydrate (0.58 g, 3.0 mmol) was added, solution was reacted for 2 hours while heating under reflux. Further, p-toluenesulfonic acid monohydrate (0.58 g, 3.0 mmol) was added, and solution was reacted for 2 hours while heating under reflux. Reaction solution was washed with aqueous solution of sodium hydroxide and water, and organic layer was extracted with diethyl ether. After organic layer was dried over magnesium sulfate, solvent was distilled off under reduced pressure to obtain the crude product.

This was purified by silica-gel column chromatography to obtain the desired 2-bromo-4-{2-methyl-4-(t-butyl)phenyl}-5-methylindene (2.45 g, 6.90 mmol).

The above-described series of reaction was repeatedly carried out by the same method, and, a total of 5.63 g (15.8 mmol) of 2-bromo-4-{2-methyl-4-(t-butyl)phenyl}-5-methylindene was obtained.

(9-6) Synthesis of 2-{2-(5-methylfuryl)}-4-(2-methyl-4-(t-butyl)phenyl)-5-methylindene 2-Methylfuran (2.05 mL, 22.9 mmol) was dissolved in dimethoxyethane (35 mL), and solution of n-butyllithium in n-hexane (1.65 M, 14.40 mL) was dropped at −78° C. After elevating temperature naturally, reaction solution was stirred for 2 hours, then, was cooled at −78° C. again, solution of triisopropyl borate (5.75 mL, 25.0 mmol) dissolved in dimethoxyethane (12 mL) was dropped. After elevating temperature naturally, reaction solution was stirred for 3 hours, then, water (10.0 mL, 555 mmol) was added, and reaction solution was stirred for 2 hours. Then, aqueous solution of sodium carbonate (1.52 M, 30 mL), solution of 2-bromo-4-{2-methyl-4-(t-butyl)phenyl}-5-methylindene (5.63 g, 15.8 mmol) dissolved in dimethoxyethane (10 mL), tetrakis(triphenylphosphine)palladium (0.92 g, 0.80 mmol) were sequentially added, and solution was reacted for 2 hours while heating under reflux, then, was washed with hydrochloric acid and water, and organic layer was extracted with diethyl ether. Organic layer was dried over magnesium sulfate, then, solvent was distilled off under reduced pressure to obtain the crude product.

This was purified with silica-gel column chromatography to obtain the desired 2-{2-(5-methylfuryl)}-4-{2-methyl-4-(t-butyl)phenyl}-5-methylindene (5.11 g, 14.3 mmol).

(9-7) Synthesis of dimethylbis[2-{2-(5-methylfuryl)}-4-{2-methyl-4-(t-butyl)phenyl}-5-methylindenyl]silane The obtained 2-{2-(5-methylfuryl)}-4-{2-methyl-4-(t-butyl)phenyl}-5-methylindene (5.11 g, 14.3 mmol) was dissolved in tetrahydrofuran (70 mL), and solution of n-butyllithium in n-hexane (1.57 M, 9.55 mL) was dropped at −83° C., and after elevating temperature naturally, reaction solution was stirred for 2 hours at room temperature, then, N-methylimidazole (57.0 µL, 0.715 mmol) was added, and solution of dichlorodimethylsilane (0.875 mL, 7.19 mmol) dissolved in tetrahydrofuran (10 mL) was dropped at −82° C. After elevating temperature naturally, reaction solution was stirred for 1.5 hours at room temperature, and water (5.00 mL, 277 mmol) was added to remove aqueous layer. Organic layer was dried over magnesium sulfate, then, solvent was distilled off under reduced pressure to obtain the crude product.

This was purified by silica-gel column chromatography to obtain the desired dimethylbis[2-(2-(5-methylfuryl))-4-{2-methyl-4-(t-butyl)phenyl}-5-methylindenyl]silane (3.73 g, 4.85 mmol).

(9-8) Synthesis of dimethylsilylenebis[2-{2-(5-methylfuryl)}-4-{2-methyl-4-(t-butyl)phenyl}-5-methylindenyl]zirconium dichloride The obtained dimethylbis[2-{2-(5-methylfuryl)}-4-{2-methyl-4-(t-butyl)phenyl}-5-methylindenyl]silane (3.73 g, 4.85 mmol) was dissolved in diethyl ether (120 mL), and solution of n-butyllithium in n-hexane (1.57 M, 6.50 mL) was dropped at −81° C. After elevating temperature naturally, reaction solution was stirred for 2 hour at room temperature, then, solvent was distilled off under reduced pressure. Diethyl ether (6.0 mL), toluene (120 mL) were sequentially added, and reaction solution was cooled at −78° C., and zirconium tetrachloride (1.15 g, 4.93 mmol) was added. After elevating temperature naturally, solution was stirred for 1.5 hours at room temperature. The obtained reaction solution was once concentrated, and extracted with toluene, and concentrated again to dryness. This was sequentially washed with n-hexane, diisopropyl ether, then, re-precipitation was carried out using toluene as rich solvent, n-hexane as poor solvent. Further, reaction solution was washed with cyclohexane, and extracted with toluene.

As a result, the desired dimethylsilylenebis[2-{2-(5-methylfuryl)}-4-{2-methyl-4-(t-butyl)phenyl}-5-methylindenyl] zirconium dichloride was obtained as a mixture of 2 kinds of racemic forms (rac-A and rac-B)(0.33 g; rac-A:rac-B=81:19) which is considered to be derived from axis asymmetry due to 4-position substituent in indenyl group.

$^1$H-NMR (400 MHz, CDCl$_3$, rac-A).1.07 (s, 6H, Si(CH$_3$)$_2$), 1.33 (s, 18H, Ph-C(CH$_3$)$_3$), 1.85 (s, 6H, Furyl-CH$_3$),2.11 (s, 6H, Ph-CH$_3$), 2.40 (s, 6H, Indenyl-CH$_3$),6.04 (dd, 2H, Furyl-H), 6.22 (d, 2H, Furyl-H), 6.38 (s, 2H, Indenyl-H), 6.65 (d, 2H, Indenyl-H), 6.74 (d, 2H, Indenyl-H), 7.19 (s, 2H, Ph-H), 7.26 (d, 2H, Ph-H), 7.50 (d, 2H, Ph-H).

$^1$H-NMR (400 MHz, CDCl$_3$, rac-B).1.03 (s, 3H, Si(CH$_3$)$_2$), 1.09 (s, 3H, Si(CH$_3$)$_2$), 1.32 (s, 9H, Ph-C(CH$_3$)$_3$), 1.33 (s, 9H, Ph-C(CH$_3$)$_3$), 1.83 (s, 3H, Furyl-CH$_3$), 1.85 (s, 3H, Furyl-CH$_3$), 2.09 (s, 3H, Ph-CH$_3$), 2.13 (s, 3H, Ph-CH$_3$), 2.41 (s, 3H, Indenyl-CH$_3$), 2.42 (s, 3H, Indenyl-CH$_3$), 6.04-7.51 (16H, Furyl-H, Indenyl-H, Ph-H).

(9-9) Preparation of Catalyst Using Metallocene Complex I (Catalyst I)

Catalyst I was obtained by the same operation as the preparation of catalyst described in [Example 3](3-6) except that 75 μmol of metallocene complex I instead of metallocene complex C was used.

Magnification ratio of pre-polymerization in this case (value of amount of pre-polymerized polymer divided by the amount of solid catalyst) was 1.86.

(9-10) Propylene-propylene•ethylene Block Copolymerization by Catalyst I 50 mg of catalyst I was used instead of catalyst A, the operation similar to [Example 1](1-8) was carried out. The average gas molar composition in reactor became propylene/ethylene-47/53 when polymerizing propylene/ethylene in the second step. As a result, 113 g of propylene-propylene•ethylene block copolymer was obtained.

From the result of CFC-IR, block copolymer obtained in the above had 23% by weight of rubber content (CP content), 36 mol % of ethylene content in rubber (CP), and 600,000 of weight average molecular weight in CP (Mw). In addition, rubber polymerization activity (CP activity) was 1000 (g-CP/g-Cat/hr). Tm of the other collected propylene homo-polymer was 150° C.

Example 10

Metallocene Complex J

Synthesis of dimethylsilylenebis[2-{2-(5-methylfuryl)}-4-(1-naphthyl)-5-methylindenyl]zirconium dichloride

(10-1) Synthesis of 4-(1-naphthyl)-5-methylindene

1-Naphthylboronic acid (10 g, 58.1 mmol) was dissolved in dimethoxyethane (150 mL), and aqueous solution (100 mL) of cesium carbonate (25.3 g, 78 mmol), 4-bromo-5-methylindene (8.1 g, 39 mmol), tetrakis(triphenylphosphine) palladium (1.8 g) were sequentially added. Solution was reacted for 21 hours while heating under reflux, then, reaction solution was poured into 1N hydrochloric acid-ice water, and after stirring, reaction solution was extracted with diethyl ether. Organic layer was washed with magnesium sulfate, then, solvent was distilled off under reduced pressure to obtain the crude product. This was purified by silica-gel column chromatography to obtain the desired 4-(1-naphthyl)-5-methylindene (8.6 g, yield: 87%).

(10-2) Synthesis of 2-bromo-4-(1-naphthyl)-5-methylindene

The obtained 4-(1-naphthyl)-5-methylindene (8.6 g, 33.0 mmol) was dissolved in dimethylsulfoxide (130 mL), and water (3 mL) was added. N-Bromosuccinimide (7.8 g, 44 mmol) was added at 0° C., and reaction solution was stirred for 2.5 hours at room temperature. Reaction solution was quenched by adding water on ice bath, and organic layer was extracted by adding toluene. p-Toluenesulfonic acid monohydrate (0.5 g) was added to organic layer. Solution was reacted for 3 hours while heating under reflux, then, water was added to the reaction solution to separate organic layer. Organic layer was washed with saturated aqueous solution of sodium chloride, and dried over magnesium sulfate, then, solvent was distilled off under reduced pressure to obtain the crude product.

This was purified by silica-gel column chromatography to obtain the desired 2-bromo-4-(1-naphthyl)-5-methylindene (9.8 g, yield: 87%).

(10-3) Synthesis of 2-{2-(5-methylfuryl)}-4-(1-naphthyl)-5-methylindene

2-Methylfuran (3.6 g, 44.3 mmol) was dissolved in dimethoxyethane (60 mL), and solution of n-butyllithium in n-hexane (1.54 M, 28.5 mL) was dropped at −76° C. reaction solution was stirred for 3 hours at −30° C., then, triisopropyl borate (11 mL, 47 mmol) was dropped, and solution was stirred for 16 hours at room temperature. By adding water (10 mL), reaction solution was stirred for 10 minutes. Then, aqueous solution (100 mL) of sodium carbonate (6.2 g, 58.5 mmol), solution of 2-bromo-4-(1-naphthyl)-5-methylindene (9.8 g, 29.3 mmol) dissolved in dimethoxyethane (40 mL), tetrakis(triphenylphosphine)palladium (0.8 g) were sequentially added, and solution was reacted for 3 hours while heating under reflux. Water was added to the reaction solution to separate organic layer, and organic layer was washed with saturated aqueous solution of sodium chloride, and dried over magnesium sulfate, then, solvent was distilled off under reduced pressure.

The obtained crude product was purified by silica-gel column chromatography to obtain the desired 2-{2-(5-methylfuryl)}-4-(1-naphthyl)-5-methylindene (4.5 g, yield 46%).

(10-4) Synthesis of dimethylbis[2-{2-(5-methylfuryl)}-4-(1-naphthyl)-5-methylindenyl]silane The obtained 2-{2-(5-methylfuryl)}-4-(1-naphthyl)-5-methylindene (4.5 g, 13.3 mmol) was dissolved in tetrahydrofuran (60 mL), and solution of n-butyllithium in n-hexane (1.54 M, 8.7 mL) was dropped at −76° C. After elevating temperature up to room temperature, reaction solution was stirred for 3 hours, then N-methylimidazole (0.02 mL) was added, and dichlorodimethylsilane (0.8 mL, 6.7 mmol) was dropped at −76° C. Reaction solution was stirred for 1 hour at room temperature, and water was added to separate organic layer. Organic layer was washed with saturated solution of sodium chloride, and dried over magnesium sulfate, then, solvent was distilled off under reduced pressure to obtain the crude product.

This was purified by silica-gel column chromatography to obtain the desired dimethylbis[2-{2-(5-methylfuryl)}-4-(1-naphthyl)-5-methylindenyl]silane (3.9 g, yield 80%).

(10-5) Synthesis of dimethylsilylenebis[2-{2-(5-methylfuryl)}-4-(1-naphthyl)-5-methylindenyl]zirconium dichloride The obtained dimethylbis[2-(2-{5-methylfuryl)}-4-(1-naphthyl)-5-methylindenyl]silane (3.9 g, 5.4 mmol) was dissolved in diethyl ether (160 mL), and solution of n-butyllithium in n-hexane (1.65 M, 6.5 mL) was dropped at −76° C. After stirring for 2 hours at room temperature, solvent was distilled off under reduced pressure. Diethyl ether (8 mL), toluene (160 mL) were sequentially added, and reaction solution was cooled at −50° C., and zirconium tetrachloride (1.2 g, 5.1 mmol) was added. After elevating temperature up to room temperature immediately, reaction solution was stirred for 3 hours. Resulting reaction solution was once concentrated, was extracted with toluene, and concentrated again to dryness. This was re-extracted with diethyl ether therefrom, and sequentially washed with n-hexane, small amount of diethyl ether.

Further, this was extracted with diethyl ether to obtain the mixture (0.5 g) of desired racemic form of dimethylsilylenebis[2-{2-(5-methylfuryl)}-4-(1-naphthyl)-5-methylindenyl]zirconium dichloride and isomer thereof.

$^1$H-NMR (400 MHz, CDCl$_3$, rac isomer).1.12 (s, 6H, Si(CH$_3$)$_2$), 2.04 (s, 6H, Furyl-CH$_3$), 2.38 (s, 6H, Indenyl-5-CH$_3$), 6.00 (d, 2H, Furyl-H), 6.16 (d, 2H, Furyl-H), 6.27 (s, 2H, Cp-H), 6.71 (d, 2H, Indenyl-H), 6.85 (d, 2H, Indenyl-H), 7.0-8.0 (m, 14H, Naphtyl-H).

(10-6) Preparation of Catalyst Using Metallocene Complex J (Catalyst J)

Catalyst J was obtained by the same operation as the preparation of catalyst described in [Example 3](3-6) except that 75 µmol of metallocene complex J instead of metallocene complex C was used.

Magnification ratio of pre-polymerization in this case (value of amount of pre-polymerized polymer divided by the amount of solid catalyst) was 1.26.

(10-7) Propylene-propylene•ethylene Block Copolymerization by Catalyst J 100 mg of catalyst J was used instead of catalyst A, the operation similar to [Example 1](1-8) was carried out. The average gas molar composition in reactor became propylene/ethylene=46/54 when polymerizing propylene/ethylene in the second step. As a result, 129 g of propylene-propylene•ethylene block copolymer was obtained.

From the result of CFC-IR, block copolymer obtained in the above had 59% by weight of rubber content (CP content), 30 mol % of ethylene content in rubber (CP), and 420,000 of weight average molecular weight in CP (Mw). In addition, rubber polymerization activity (CP activity) was 670 (g-CP/g-Cat/hr). Tm of the other collected propylene homo-polymer was 152° C.

Example 11

Metallocene Complex K

Synthesis of dimethylsilylenebis(2-(2-(5-methylfuryl))-4-(2-naphthyl)-5-methylindenyl)zirconium dichloride (11-1) Synthesis of 4-(2-naphthyl)-5-methylindene To mixed solution of 2-naphthylboronic acid (5 g, 29 mmol) and DME (100 mL), aqueous solution (30 mL) of cesium carbonate (12 g, 36.8 mmol)(30 mL) and 5-methyl-4-bromoindene (4.3 g, 21 mmol), tetrakis(triphenylphosphino)palladium (0.9 g) were added, and heated under reflux. After 16 hours, reaction solution was poured into 1N HCl-ice water to separate organic layer after stirring. Organic layer was washed with saturated solution of sodium chloride after filtering through Celite, and dried over magnesium sulfate, and solvent was distilled off under reduced pressure. The obtained crude product was purified by column chromatography (Silica-gel: produced by Kanto Chemical Co., Inc., hexane) to obtain the desired 4-(2-naphthyl)-5-methylindene (3.9 g, yield: 74%).

(11-2) Synthesis of 2-bromo-4-(2-naphthyl)-5-methylindene 4-(2-naphthyl)-5-methylindene (3.9 g, 15.2 mmol) synthesized in the above was dissolved in DMSO (50 mL) and distilled water (1 mL), and N-bromosuccinimide (3.7 g) was added under cooling on ice bath, and reaction solution was stirred for 2 hours at room temperature. And reaction solution was quenched by adding water, and organic layer was separated by adding toluene. Subsequently, to organic layer of toluene, catalyst amount of p-toluenesulfonic acid was added, and reaction solution was heated for 2 hours under reflux. Organic layer was separated by adding water to the reaction solution, and washed with saturated solution of sodium chloride, was dried over magnesium sulfate, and solvent was distilled off under reduced pressure.

The obtained crude product was purified by column chromatography (Silica-gel, hexane-ether: produced by Kanto Chemical co., Inc.,) to obtain the desired 2-bromo-4-(2-naphthyl)-5-methylindene (3 g, yield: 79%).

(11-3) Synthesis of 2-(2-(5-methylfuryl))-4-(2-naphthyl)-5-methylindene

Solution of 2-methylfuran (1.4 g, 17.0 mmol) in absolute DME was cooled at −70° C., and solution of n-butyllithium in n-hexane (1.66 M, 10 mL) was dropped. Reaction solution was stirred for 2 hours at low temperature of about −30° C. as it was, subsequently, triisopropyl borate (4.2 ml, 18 mmol) was added, and reaction solution was stirred at room temperature day and night. After stirring, distilled water (5 mL) was added to hydrolyze, and aqueous solution (20 mL) of sodium carbonate (2.4 g, 22.6 mmol), 2-bromo-4-(2-naphthyl)-5-methylindene (3.8 g, 11.3 mmol) synthesized in the above, further, tetrakis(triphenylphosphino)palladium (0.9 g) were added, and heated for 2.5 hours under reflux. Reaction solution was added to water to separate organic layer, and organic layer was filtered through Celite, and washed with saturated solution of sodium chloride, and dried over magnesium sulfate, and solvent was distilled off under reduced pressure.

The obtained crude product was purified by column chromatography (Silica-gel, hexane: produced by Kanto Chemical co., Inc) to obtain the desired 2-(2-(5-methylfuryl))-4-(2-naphthyl)-5-methylindene (3.4 g, yield: 90%).

(11-4) Synthesis of dimethylbis(2-(2-(5-methylfuryl))-4-(2-naphthyl)-5-methylindenyl)silane 2-(2-(5-Methyl)-furyl)-4-(2-naphthyl)-5-methylindene (3.4 g) was dissolved in absolute THF (50 mL), solution of n-butyllithium in n-hexane (1.65 M, 6.1 mL) was dropped at −72° C. After dropping, temperature was elevated up to room temperature, and reaction solution was stirred for about 2.5 hours, then, N-methylimidazol (0.2 mL) was added, and dichlorodimethylsilane (0.6 mL, 5 mmol) was dropped at −72° C. After dropping, temperature was elevated up to room temperature, and reaction solution was stirred day and night. After completing reaction, distilled water was added, then, aqueous layer was removed. Organic layer was dried over magnesium sulfate, then, solvent was distilled off under reduced pressure.

The obtained crude product was purified by column chromatography (silica-gel, hexane: produced by Kanto Chemical Co., Inc) to obtain dimethylbis(2-(2-(5-methylfuryl))-4-(2-naphthyl)-5-methylindenyl)silane (2.4 g, yield: 65%).

(11-5) Synthesis of dimethylsilylenebis(2-(2-(5-methylfuryl))-4-(2-naphthyl)-5-methylindenyl)zirconium dichloride Dimethylbis(2-(2-(5-methylfuryl))-4-(2-naphthyl)-5-methylindenyl)silane (2.4 g) was dissolved in absolute ether (100 mL) and cooled at −72° C., and solution of n-butyllithium in n-hexane (1.65 M, 4.0 mL) was dropped. After elevating temperature up to room temperature, reaction solution was stirred for 2 hours, then, solvent was distilled off under reduced pressure, and absolute ether (5 mL) and absolute toluene (100 mL) were added, and reaction solution was cooled down to −70° C. again, and tetrachlorozirconium (0.76 g, 3.3 mmol) was added. After elevating temperature up to room temperature immediately, reaction solution was stirred for 2 hours.

After completing reaction, solvent was once distilled off, and washed with ether, and extracted with toluene, and subsequently washed with hexane to obtain racemic form complex of the desired dimethylsilylenebis(2-(2-(5-methylfuryl))-4-(2-naphthyl)-5-methylindenyl)zirconium dichloride (0.8 g, yield: 27%).

$^1$H-NMR (400 MHz, CDCl$_3$) δ 1.11 (s, 6H, SiMe$_2$), 2.29 (dr, 6H, 5-Me), 2.40 (s, 6H, furyl-Me), 6.04 (d, J=3.3 Hz, 2H, furyl), 6.21 (d, J=3.0 Hz, 2H, furyl), 6.4-6.6 (m, 2H, Cp), 6.69 (d, J=9.1 Hz, 2H, ind), 6.81 (d, J=8.8 Hz, 2H, ind), 7.2-8.3 (m, 14H, Ph)

(11-6) Preparation of Catalyst Using Metallocene Complex K (Catalyst K)

Catalyst K was obtained by the same operation as the preparation of catalyst according to [Example 3](3-6) except that 75 μmol of metallocene complex K instead of metallocene complex C was used.

Magnification ratio of pre-polymerization in this case (value of amount of pre-polymerized polymer divided by the amount of solid catalyst) was 0.23.

(11-7) Propylene-propylene•ethylene Block Copolymerization by Catalyst K 30 mg of catalyst K was used instead of catalyst A, and the operation similar to [Example 1](1-8) was carried out. The average gas molar composition in reactor became propylene/ethylene=49/51 when polymerizing propylene/ethylene in the second step. As a result, 15 g of propylene-propylene•ethylene block copolymer was obtained.

From the result of CFC-IR, block copolymer obtained in the above had 11% by weight of rubber content (CP content), 44 mol % of ethylene content in rubber (CP), and 408,000 of weight average molecular weight in CP (Mw). In addition, rubber polymerization activity (CP activity) was 55 (g-CP/g-Cat/hr). Tm of the other collected propylene homo-polymer was 157° C.

Example 12

Metallocene Complex L

Synthesis of dimethylsilylenebis(2-(5-methyl-2-furyl)-4-(4-biphenylyl)-5-methyl-indenyl)zirconium dichloride (12-1) Synthesis of 4-(4-biphenylyl)-5-methylindene 4-Biphenylylboronic acid (6.8 g, 34.5 mmol) was added to dimethoxyethane (120 mL) and water (25 mL), and cesium carbonate (15 g, 46 mmol), 4-bromo-5methylindene (5.09 g, 23 mmol), tetrakis(triphenylphosphine)palladium (0.8 g, 0.69 mmol) were sequentially added. Reaction solution was intermittently reacted for 23 hours while heating under reflux, then, was washed with diluted hydrochloric acid and water, and organic layer was extracted with diethyl ether. After solvent was distilled off, reaction solution was filtered with silica-gel using hexane-dichloromethane (1:1), and solvent was distilled off to obtain the crude product (7.0 g).

This was re-crystallized using heptane (50 mL) to obtain the desired 4-biphenylyl-5-methylindene (4.47 g, yield: 68%).

(12-2) Synthesis of 2-bromo-4-(4-biphenylyl)-5-methylindene

The obtained 4-biphenylyl-5-methylindene (4.47 g, 15.8 mmol) was dissolved in dimethylsulfoxide (40 mL), and water (1.1 g) was added. N-Bromosuccinimide (NBS) (3.37 g, 18.96 mmol) was added at 5 to 10° C., and after elevating temperature naturally, reaction solution was stirred for 1 hour at room temperature. Reaction solution was slowly added to the mixed solution of toluene and water at room temperature, then, aqueous phase was separated. Organic layer was washed with diluted hydrochloric acid to remove aqueous phase, then, p-toluenesulfonic acid monohydrate (0.45 g, 2.37 mmol) was added. Solution was reacted for 1.5 hours while heating under reflux, then, was cooled, and washed with aqueous solution of sodium hydroxide (1 N) and water, and organic layer was extracted. Organic layer was dried over magnesium sulfate, then, solvent was distilled off under reduced pressure to obtain the crude product (5.5 g).

This was re-crystallized using heptane (80 mL), and purified to obtain the desired 2-bromo-4-biphenylyl-5-methylindene (4.5 g, yield: 79%).

(12-3) Synthesis of 2-(2-(5-methylfuryl))-4-(4-biphenylyl)-5-methylindene

2-Methylfuran (1.47 mL, 16.25 mmol) was dissolved in dimethoxyethane (30 mL), and solution of n-butyllithium in n-hexane (9.8 mL, 16.25 mmol) was dropped at −30° C. After elevating temperature naturally, reaction solution was stirred for 4 hours at room temperature, then, was repeatedly cooled at −30° C., and solution of triisopropyl borate (4.0 mL, 17.5 mmoL) in dimethoxyethane (10 mL) was dropped. Reaction solution was stirred for 1 hour at −30° C., and for 15 hours at room temperature, then, water (20 mL), sodium carbonate (3.5 g, 32.5 mmol), 2-bromo-4-biphenylyl-5-methylindene (4.5 g, 12.5 mmol) obtained in the above, tetrakis(triphenylphosphine)palladium (0.72 g, 0.625 mmol) were sequentially added, and solution was reacted for 3 hours while heating under reflux, then, was washed with diluted hydrochloric acid, and organic layer was extracted by adding diethyl ether. Organic layer was dried over magnesium sulfate, then, solvent was distilled off under reduced pressure to obtain the crude product (5.11 g).

This was re-crystallized using heptane (80 mL) and toluene (30 mL) to obtain the desired 2-methylfuryl-4-biphenylyl-5-methylindene (4.32 g, yield: 96%).

(12-4) Synthesis of dimethylbis(2-(2-(5-methylfuryl))-4-(4-biphenylyl)-5-methylindenyl)silane 2-(2-(5-methylfuryl))-4-biphenylyl-5-methylindene (2.19 g, 6.05 mmol) was dissolved in tetrahydrofuran (30 mL), and solution of n-butyllithium in n-hexane (3.7 mL, 6.05 mmol) was dropped at −60° C. Reaction solution was stirred for 1 hour at −60° C., and for 2 hours at room temperature, then, N-methylimidazole (15 µL, 0.15 mmol) was added, and dichlorodimethylsilane (0.35 mL, 2.9 mmol) was dropped at −30° C. Reaction solution was stirred for 15 minutes at −30° C. and for 2 hours at room temperature, and diluted hydrochloric acid was added to remove aqueous layer. Organic layer was dried over magnesium sulfate, then, solvent was distilled off under reduced pressure to obtain the crude product (2.93 g).

This was dissolved in toluene and filtered through silica-gel to obtain the desired dimethylbis{2-2-(5-methylfuryl))-4-biphenylyl)-5-methylindenyl}silane (2.09 g, yield 93%).

(12-5) Synthesis of dimethylsilylenebis(2-(2-(5-methylfuryl))-4-(4-biphenylyl)-5-methylindenyl)zirconium dichloride Dimethylbis{2-2-(5-methylfuryl)}-4-biphenylyl}-5-methylindenyl}silane (2.09 g, 2.67 mmol) was dissolved in diethyl ether (20 mL), and solution of n-butyllithium in n-hexane (3.2 mL, 5.35 mmol) was dropped at −20° C. Reaction solution was stirred for 30 minutes at −20° C. and for 3 hours at room temperature, then, toluene (75 mL) was added, and cooled at −20° C., and zirconium tetrachloride (0.62 g, 2.67 mmol) was added. After elevating temperature naturally, reaction solution was stirred for 1.5 hours at room temperature. Soluble part was separated by decantation from resulting reaction solution, and insoluble part and soluble part were separated.

Thereafter, soluble part was washed with dichloromethane (100 mL), ethanol (15 mL) to obtain the desired dichlorodimethylsilylenebis(2-(5-methyl-2-furyl)-4-(4-biphenylyl)-5-methyl-indenyl)zirconium (1.60 g, yield: 64%).

$^1$H-NMR (400 MHz, CDCl$^3$).1.10 (s, 6H, Me$_2$Si), 2.31 (s, 3H, CH$_3$), 2.41 (s, 3H, CH$_3$), 6.04 (brs, 1H), 6.24 (brs, 1H), 6.62 (s, 1H), 6.68 (d, 1H, J=9 Hz), 6.77 (d, 1H, J=9 Hz), 7.35-7.8 (m, 22H, arom).

(12-6) Preparation of Catalyst Using Metallocene Complex L (Catalyst L)

Catalyst L was obtained by the same operation as the preparation of catalyst described in [Example 3](3-6) except that 75 µmol of metallocene complex L instead of metallocene complex C was used.

Magnification ratio of pre-polymerization in this case (value of amount of pre-polymerized polymer divided by the amount of solid catalyst) was 1.76.

(12-7) Propylene-propylene•ethylene Block Copolymerization by Catalyst L 50 mg of catalyst L was used instead of catalyst A, and the operation similar to [Example 1](1-8) was carried out. The average gas molar composition in reactor became propylene/ethylene=45/55 when polymerizing propylene/ethylene in the second step. As a result, 207 g of propylene-propylene•ethylene block copolymer was obtained.

From the result of CFC-IR, block copolymer obtained in the above had 32% by weight of rubber content (CP content), 39 mol % of ethylene content in rubber (CP), and 350,000 of weight average molecular weight in CP (Mw). In addition, rubber polymerization activity (CP activity) was 2700 (g-CP/q-Cat/hr). Tm of the other collected propylene homo-polymer was 155° C.

Example 13

Metallocene Complex M

Synthesis of dimethylsilylenebis(2-(2-(5-methylfuryl))-4-(4-methoxyphenyl)-5-methylindenyl)zirconium dichloride (13-1) Synthesis of 4-(4-methoxyphenyl)-5-methylindene To mixed solution of 4-methoxyphenylboronic acid (10 g, 66 mmol) and DME (100 mL), aqueous solution (100 mL) of cesium carbonate (28.6 g, 88 mmol) and 5-methyl-4-bromoindene (9.2 g, 44 mmol), tetrakis(triphenylphosphino)palladium (2 g) were added, and reaction solution was heated under reflux. After 19.5 hours, reaction solution was poured into 1N HCl-icewater, after stirring, ether was added to separate organic layer. Organic layer was filtered through Celite, and washed with saturated solution of sodium chloride, and dried over magnesium sulfate, and solvent was distilled off under reduced pressure.

The obtained crude product was purified by column chromatography (Silica-gel: Kanto Chemical Co., Inc, hexane) to obtain the desired 4-(4-methoxyphenyl)-5-methylindene (8 g, yield: 78%).

(13-2) Synthesis of 2-bromo-4-(4-methoxyphenyl)-5-methylindene 4-(4-Methoxyphenyl)-5-methylindene (4 g, 16.9 mmol) synthesized in the above was dissolved in DMSO (50 mL) and distilled water (1 mL), and N-bromosuccinimide (3.9 g) was added under cooling on ice bath, and reaction solution was stirred for 2 hours at room temperature. Reaction solution was quenched by adding water on ice bath, and organic layer was separated by adding toluene. Subsequently, catalyst amount of p-toluenesulfonic acid was added to toluene organic layer, and reaction solution was heated for 1 hour under reflux. Water was added to the reaction solution to separate organic layer, and washed with saturated solution of sodium chloride, and dried over magnesium sulfate, and solvent was distilled off under reduced pressure to obtain the crude product of 2-bromo-4-(4-methoxyphenyl)-5-methylindene.

(13-3) Synthesis of 2-(2-(5-methylfuryl)-4-(4-methoxyphenyl)-5-methylindene

Solution of 2-methylfuran (1.9 g, 23 mmol) in absolute DME was cooled at −70° C., and solution of n-butyllithium in n-hexane (1.66 M, 14 mL) was dropped. Reaction solution was stirred for 3 hours at low temperature of about −30° C. as it was, subsequently, triisopropyl borate (5.9 mL, 25.5 mmol) was added, and reaction solution was stirred at room temperature day and night. After stirring, distilled water (5 mL) was added to hydrolyze, and aqueous solution (20 mL) of sodium carbonate (4.8 g, 45 mmol), crude product of 2-bromo-4-(4-methoxyphenyl)-5-methylindene synthesized in the above, further, tetrakis(triphenylphosphino)palladium (0.6 g) were added, and heated for 2.5 hours under reflux. Water was added to the reaction solution to separate organic layer, organic layer was filtered through Celite, and washed with saturated solution of sodium chloride, and dried over magnesium sulfate, and solvent was distilled off under reduced pressure.

The obtained crude product was purified by column chromatography (Silica-gel: produced by Kanto Chemical Co., Inc, hexane) to obtain the desired 2-(2-(5-methylfuryl))-4-(4-methoxyphenyl)-5-methylindene (4.2 g, yield: 75%).

(13-4) Synthesis of dimethylbis(2-(2-(5-methylfuryl))-4-(4-methoxyphenyl)-5-methylindenyl)silane The synthesized 2-(2-(5-methylfuryl))-4-(4-methoxyphenyl)-5-methylindene (7.3 g) was dissolved in absolute THF (100 mL), and solution of n-butyllithium in n-hexane (1.66 M, 13.9 mL) was dropped at −72° C. After dropping, temperature was elevated up to room temperature, and reaction solution was stirred for 3 hours, then, N-methylimidazol (0.2 mL) was added, and dichlorodimethylsilane (1.4 mL, 11.5 mmol) was dropped at −72° C. After dropping, temperature was elevated up to room temperature, and reaction solution was stirred day and night. After completing reaction, distilled water was added, then, aqueous layer was removed. Organic layer was dried over magnesium sulfate, then, solvent was distilled off under reduced pressure.

The obtained crude product was purified by column chromatography (Silica-gel: produced by Kanto Chemical Co., Inc, hexane) to obtain the desired dimethylbis(2-(2-(5-methylfuryl)-4-(4-methoxyphenyl)-5-methylindenyl)silane (7.1 g, yield: 89%).

(13-5) Synthesis of dimethylsilylenebis(2-(2-(5-methylfuryl))-4-(4-methoxyphenyl)-5-methylindenyl)zirconium dichloride Ligand (3.5 g) was dissolved in absolute ether (200 mL), and cooled at −72° C., and solution of n-butyllithium in n-hexane (1.65 M, 6.2 mL) was dropped. After elevating temperature up to room temperature, reaction solution was stirred for 2 hours, then, solvent was distilled off, and absolute ether (10 mL) and absolute toluene (200 mL) were added, and reaction solution was cooled at −70° C. again, and tetrachlorozirconium (1.2 g, 5.1 mmol) was added. After elevating temperature up to room temperature immediately, reaction solution was stirred for 2 hours.

After completing reaction, solvent was once distilled off, and reaction solution was extracted with toluene, subsequently, hexane washing, ether washing, toluene washing, ether washing were carried out to obtain the desired racemic form of dimethylsilylenebis(2-(2-(5-methylfuryl))-4-(4-methoxyphenyl)-5-methylindenyl)zirconium dichloride (1.6 g, yield: 37%).

$^1$H-NMR (400 MHz, CDCl$_3$) δ 1.08 (s, 6H, SiMe$_2$), 2.25 (s, 6H, furyl-Me), 2.40 (s, 6H, 5-Me), 3.83 (s, 6H, MeO—), 6.03 (s, 2H, furyl), 6.20 (s, 2H, furyl), 6.54 (s, 2H, Cp), 6.64 (d, J=8.8 Hz, 2H, ind), 6.75 (d, J=8.8 Hz, 2H, ind), 6.8-7.7 (m, 8H, Ph).

(13-6) Preparation of Catalyst Using Metallocene Complex M (Catalyst M)

Catalyst M was obtained by the same operation as the preparation of catalyst described in [Example 3](3-6) except that 75 μmol of metallocene complex M instead of metallocene complex C was used.

Magnification ratio of pre-polymerization in this case (value of amount of pre-polymerized polymer divided by the amount of solid catalyst) was 0.99.

(13-7) Propylene-propylene•ethylene Block Copolymerization by Catalyst M

By using 75 mg of catalyst M instead of catalyst A, the operation similar to [Example 1](1-8) was carried out. The average gas molar composition in reactor became propylene/ethylene=53/47 when polymerizing propylene/ethylene in the second step. As a result, 228 g of propylene-propylene•ethylene block copolymer was obtained.

From the result of CFC-IR, block copolymer obtained in the above had 72% by weight of rubber content (CP content), 39 mol % of ethylene content in rubber (CP), and 220,000 of weight average molecular weight in CP (Mw). In addition, rubber polymerization activity (CP activity) was 4,400 (g-CP/g-Cat/hr). Tm of the other collected propylene homopolymer was 155° C.

Example 14

Metallocene Complex N

Synthesis of dimethylsilylenebis[2-{2-(5-methylfuryl)}-4-(4-trifluoromethylphenyl)-5-methylindenyl]zirconium dichloride

(14-1) Synthesis of 4-(4-trifluoromethylphenyl)-5-methylindene

4-Trifluoromethylphenylboronic acid (10.00 g, 52.7 mmol) was dissolved in dimethoxyethane (250 mL), and aqueous solution of cesium carbonate (1.03 M, 70 mL), 4-bromo-5-methylindene (8.05 g, 38.5 mmol), tetrakis(triphenylphosphine)palladium (1.40 g, 1.21 mmol) ware sequentially added. Solution was reacted for 16 hours while heating under reflux, then, was washed with hydrochloric acid and water, and organic layer was extracted with diethyl ether. Organic layer was dried over magnesium sulfate, then, solvent was distilled off under reduced pressure to obtain the crude product.

This was purified by silica-gel column chromatography to obtain the desired 4-(4-trifluoromethylphenyl)-5-methylindene (6.44 g, 23.5 mmol).

(14-2) Synthesis of 2-bromo-4-(4-trifluoromethylphenyl)-5-methylindene

The obtained 4-(4-trifluoromethylphenyl)-5-methylindene (6.44 g, 23.5 mmol) was dissolved in dimethylsulfoxide (55 mL), and water (1.70 mL, 94.3 mmol) was added. N-Bromosuccinimide (5.46 g, 30.7 mmol) was added at 10° C., and after elevating temperature naturally, reaction solution was stirred for 19 hours. After the mixed solution of toluene and water was slowly added to the reaction solution, aqueous phase was separated, then, organic layer was washed with hydrochloric acid and water, and aqueous phase was removed, then, p-toluenesulfonic acid monohydrate (0.70 g, 3.7 mmol) was added. Solution was reacted for 2 hours while heating under reflux, then, was washed with aqueous solution of sodium hydroxide and water, and organic layer was extracted with diethyl ether. Organic layer was dried over magnesium sulfate, then, solvent was distilled off under reduced pressure to obtain the crude product.

This was purified by silica-gel column chromatography to obtain the desired 2-bromo-4-(4-trifluoromethylphenyl)-5-methylindene (7.18 g, 20.3 mmol).

(14-3) Synthesis of 2-{2-(5-methylfuryl)}-4-(4-trifluoromethylphenyl)-5-methylindene 2-Methylfuran (2.60 mL, 29.0 mmol) was dissolved in dimethoxyethane (45 mL), and solution of n-butyllithium in n-hexane (1.66 M, 18.40 mL) was dropped at −76° C. After elevating temperature naturally, reaction solution was stirred for 2 hours at room temperature, then, was cooled at −76° C. again, and solution of triisopropyl borate (7.35 mL, 32.0 mmol) dissolved in dimethoxyethane (5 mL) was dropped. After elevating temperature naturally, reaction solution was stirred for 16 hours at room temperature, then, water (12.0 mL, 666 mmol) was added, reaction solution was stirred for 1 hour. Thereafter, aqueous solution of sodium carbonate (1.47 M, 40 mL), solution of 2-bromo-4-(4-trifluoromethylphenyl)-5-methylindene (7.18 g, 20.3 mmol) dissolved in dimethoxyethane (10 mL), tetrakis(triphenylphosphine)palladium (1.25 g, 1.08 mmol) were sequentially added, and solution was reacted for 5 hours while heating under reflux, then, solution was washed with hydrochloric acid and water, organic layer was extracted with diethyl ether. Organic layer was dried over magnesium sulfate, then, solvent was distilled off under reduced pressure to obtain the crude product.

This was re-crystallized in hexane to obtain the desired 2-{2-(5-methylfuryl)}-4-(4-trifluoromethylphenyl)-5-methylindene (6.26 g, 17.7 mmol).

(14-4) Synthesis of dimethylbis[2-(2-{5-methylfuryl)}-4-(4-trifluoromethylphenyl)-5-methylindenyl]silane The obtained 2-{2-(5-methylfuryl)}-4-(4-trifluoromethylphenyl)-5-methylindene (6.26 g, 17.7 mmol) was dissolved in tetrahydrofuran (90 mL), and solution of n-butyllithium in n-hexane (1.54 M, 12.10 mL) was dropped at −75° C. After elevating temperature naturally, reaction solution was stirred for 2 hours at room temperature, then, N-methylimidazole (71.0 μL, 0.891 mmol) was added, solution of dichlorodimethylsilane (1.10 mL, 9.03 mmol) dissolved in tetrahydrofuran (10 mL) was dropped at −75° C. After elevating temperature naturally, reaction solution was stirred for 15 hours at room temperature, and water (5.50 mL, 305 mmol) was added to remove aqueous layer. Organic layer was dried over magnesium sulfate, then, solvent was distilled off under reduced pressure to obtain the crude product.

This was purified by silica-gel column chromatography to obtain the desired dimethylbis[2-{2-(5-methylfuryl)}-4-(4-trifluoromethylphenyl)-5-methylindenyl]silane (3.73 g, 4.88 mmol).

(14-5) Synthesis of dimethylsilylenebis[2-{2-(5-methylfuryl)}-4-(4-trifluoromethylphenyl)-5-methylindenyl]zirconium dichloride The obtained dimethylbis[2-{2-(5-methylfuryl)}-4-(4-trifluoromethylphenyl)-5-methylindenyl]silane (3.73 g, 4.88 mmol) was dissolved in diethyl ether (120 mL), and solution of n-butyllithium in n-hexane (1.54 M, 6.65 mL) was dropped at −76° C. After elevating temperature naturally, reaction solution was stirred for 2 hours at room temperature, then, solvent was distilled off under reduced pressure. Diethyl ether (6.0 mL), toluene (120 mL) were sequentially added, and reaction solution was cooled at −75° C., and zirconium tetrachloride (1.15 g, 4.93 mmol) was added. After elevating temperature naturally, reaction solution was stirred for 12 hours at room temperature. The obtained reaction solution was once concentrated, and extracted with toluene, and concentrated again to dryness. This was sequentially washed with n-hexane, cyclohexane, n-hexane, further, re-precipitation was carried out using toluene as rich solvent, n-hexane as poor solvent.

As a result, racemic form (0.67 g) of the desired dimethylsilylenebis[2-{2-(5-methylfuryl)}-4-(4-trifluoromethylphenyl)-5-methylindenyl]zirconium dichloride was obtained.

$^1$H-NMR (400 MHz, CDCl$_3$, rac isomer) 1.10 (s, 6H, Si(CH$_3$)$_2$), 2.23 (s, 6H, Furyl-CH$_3$), 2.41 (s, 6H, Indenyl-CH$_3$), 6.05 (dd, 2H, Furyl-H), 6.21 (d, 2H, Furyl-H), 6.47 (s, 2H, Indenyl-H), 6.67 (d, 2H, Indenyl-H), 6.81 (d, 2H, Indenyl-H), 7.17-7.26 (m, 2H, Ph-H), 7.62-7.81 (m, 6H, Ph-H).

(14-6) Preparation of catalyst using metallocene complex N(Catalyst N)

Catalyst N was obtained by the same operation as the preparation of catalyst described in [Example 3](3-6) except that 75 μmol of metallocene complex N instead of metallocene complex C was used.

Magnification ratio of pre-polymerization in this case (value of amount of pre-polymerized polymer divided by the amount of solid catalyst) was 0.15.

(14-7) Propylene-propylene•ethylene block copolymerization by catalyst N 200 mg of catalyst N was used instead of catalyst A, and the operation similar to [Example 1](1-8) was carried out. The average gas molar composition in reactor became propylene/ethylene=50/50 when polymerizing propylene/ethylene in the second step. As a result, 100 g of propylene-propylene•ethylene block copolymer was obtained.

From the result of CFC-IR, block copolymer obtained in the above had 26% by weight of rubber content (CP content), 46 mol % of ethylene content in rubber (CP), and 240,000 of weight average molecular weight in CP (Mw). In addition, rubber polymerization activity (CP activity) was 260 (g-CP/g-Cat/hr). Tm of the other collected propylene homo-polymer was 154° C.

Example 15

Metallocene Complex O

Synthesis of dimethylsilylenebis[2-{2-(5-methylfuryl)}-4-(3,5-dimethoxyphenyl)-5-methylindenyl] zirconium dichloride (15-1) Synthesis of 4-(3,5-dimethoxyphenyl)-5-methylindene 3,5-Dimethoxyphenylboronic acid (10 g, 55 mmol) was dissolved in dimethoxyethane (200 mL), and aqueous solution (60 mL) of cesium carbonate (24 g, 73 mmol), 4-bromo-5-methylindene (7.6 g, 36 mmol), tetrakis(triphenylphosphine)palladium (1.6 g) were sequentially added. Solution was reacted for 18 hours while heating under reflux, then, reaction solution was poured into HCl-ice water, after stirring, organic layer was extracted with diethyl ether, and washed with saturated solution of sodium chloride, and dried over magnesium sulfate, then, solvent was distilled off under reduced pressure to obtain the crude product.

This was purified by silica-gel column chromatography to obtain the desired 4-(3,5-dimethoxyphenyl)-5-methylindene (7.7 g, yield: 80%).

(15-2) Synthesis of 2-bromo-4-(3,5-dimethoxyphenyl)-5-methylindene

The obtained 4-(3,5-dimethoxyphenyl)-5-methylindene (3.5 g, 13.1 mmol) was dissolved in dimethylsulfoxide (50 mL), and water (1 mL) was added. N-Bromosuccinimide (3.5 g, 19.7 mmol) was added at 0° C., and reaction solution was stirred for 2 hours at room temperature. Reaction solution was quenched by adding water on ice bath, and organic layer was extracted by adding toluene. p-Toluenesulfonic acid monohydrate (0.7 g, 3.7 mmol) was added to organic layer. After solution was reacted for 2 hours while heating under reflux, water was added to reaction solution to separate organic layer. Organic layer was washed with saturated solution of sodium chloride, and dried over magnesium sulfate, then, solvent was distilled off under reduced pressure to obtain the crude product.

This was purified by silica-gel column chromatography to obtain the desired 2-bromo-4-(3,5-dimethoxyphenyl)-5-methylindene (0.5 g, yield: 11%).

(15-3) Synthesis of 2-{2-(5-methylfuryl)}-4-(3,5-dimethoxyphenyl)-5-methylindene 2-Methylfuran (1.4 g, 17.0 mmol) was dissolved in dimethoxyethane (10 mL), and solution of n-butyllithium in n-hexane (1.66 M, 10.2 mL) was dropped at −76° C. After stirring for 3 hours at −30° C., triisopropyl borate (3.4 g, 18.1 mmol) was dropped, and reaction solution was stirred for 16 hours at room temperature. Water (5 mL) was added, and reaction solution was stirred for 1 hour. Then, aqueous solution (30 mL) of sodium carbonate (2.4 g, 22.6 mmol), solution of 2-bromo-4-(3,5-dimethoxyphenyl)-5-methylindene (3.9 g, 11.3 mmol) dissolved in dimethoxyethane (30 mL), tetrakis(triphenylphosphine)palladium (0.3 g) were sequentially added, and solution was reacted for 1 hour while heating under reflux. Organic layer was separated by adding water to the reaction solution, was washed with saturated solution of sodium chloride, and dried over magnesium sulfate, then, solvent was distilled off under reduced pressure.

The obtained crude product was purified by silica-gel column chromatograph to obtain the desired 2-{2-(5-methylfuryl)}-4-(3,5-dimethoxyphenyl)-5-methylindene (2.9 g, yield: 74%).

(15-4) Synthesis of dimethylbis[2-{2-(5-methylfuryl)}-4-(3,5-dimethoxyphenyl)-5-methylindenyl] silane The obtained 2-{2-(5-methylfuryl)}-4-(3,5-dimethoxyphenyl)-5-methylindene (2.9 g, 8.4 mmol) was dissolved in tetrahydrofuran (50 mL), and solution of n-butyllithium in n-hexane (1.65 M, 5.1 mL) was dropped at −76° C. By elevating temperature up to room temperature, reaction solution was stirred for 3 hours, then, N-methylimidazole (0.02 mL) was added, dichlorodimethylsilane (0.5 mL, 4.1 mmol) was dropped at −76° C. Reaction solution was stirred for 2.5 hours at room temperature, and water was added to separate organic layer. Organic layer was washed with saturated sodium chloride, and dried over magnesium sulfate, then, solvent was distilled off under reduced pressure to obtain the crude product.

This was purified by silica-gel column chromatograph to obtain the desired dimethylbis[2-{2-(5-methylfuryl)}-4-(3,5-dimethoxyphenyl)-5-methylindenyl]silane (2.5 g, yield: 80%).

(15-5) Synthesis of [2-{2-(5-methylfuryl)}-4-(3,5-dimethoxyphenyl)-5-methylindenyl]zirconium dichloride The obtained dimethylbis[2-{(2-(5-methylfuryl)}-4-(3,5-dimethoxyphenyl)-5-methylindenyl]silane (2.5 g, 3.3 mmol) was dissolved in diethyl ether (150 mL), and solution of n-butyllithium in n-hexane (1.66 M, 4.0 mL) was dropped at −76° C. Reaction solution was stirred for 2 hours at room temperature, then, solvent was distilled off under reduced pressure. Diethyl ether (6 mL), toluene (120 mL) were sequentially added, and cooled at −50° C., and zirconium tetrachloride (0.78 g, 3.3 mmol) was added. After elevating temperature naturally, reaction solution was stirred for 2 hours at room temperature. The obtained reaction solution was once concentrated, and extracted with toluene, and concentrated again to dryness. This was extracted with diisopropyl ether again, and washed with n-hexane, diethyl ether.

Subsequently, this was re-crystallized with toluene-hexane solvent, and the obtained crystal was washed with hexane to obtain racemic form (0.25 g) of the desired dimethylsilylenebis(2-(2-(5-methylfuryl))-4-(3,5-dimethoxyphenyl)-5-methylindenyl)zirconium dichloride.

$^1$H-NMR (400 MHz, CDCl$_3$, rac isomer) 1.08 (s, 6H, Si(CH$_3$)$_2$), 2.29 (s, 6H, Furyl-CH$_3$), 2.40 (s, 6H, Indenyl-5-CH$_3$), 3.74 (s, 12H, —OMe), 6.04 (dd, 2H, Furyl-H), 6.21 (d, 2H, Furyl-H), 6.34 (s, 2H, Cp-H), 6.44 (m, 2H, Ph-H), 6.59 (s, 2H, Ph-H), 6.65 (d, 2H, Indenyl-H), 6.76 (d, 2H, Indenyl-H), 6.94 (s, 2H, Ph-H).

(15-6) Preparation of Catalyst Using Metallocene Complex O(Catalyst O)

Catalyst O was obtained by the same operation as the preparation of catalyst described in [Example 3](3-6) except that 75 µmol of metallocene complex O instead of metallocene complex C was used.

Magnification ratio of pre-polymerization in this case (value of amount of pre-polymerized polymer divided by the amount of solid catalyst) was 0.37.

(15-7) Propylene-propylene•ethylene Block Copolymerization by Catalyst O 75 mg of catalyst O was used instead of catalyst A, the operation similar to [Example 1](1-8) was carried out. The average gas molar composition in reactor became propylene/ethylene=50/50 when polymerizing propylene/ethylene in the second step. As a result, 132 g of propylene-propylene•ethylene block copolymer was obtained.

From the result of CFC-IR, block copolymer obtained in the above had 23% by weight of rubber content (CP content), 44 mol % of ethylene content in rubber (CP), and 230,000 of weight average molecular weight in CP (Mw). In addition, rubber polymerization activity (CP activity) was 800 (g-CP/g-Cat/hr). Tm of the other collected propylene homo-polymer was 154° C.

Example 16

Metallocene Complex P

Synthesis of dimethylsilylenebis[2-{2-(5-methylfuryl)}-4-(3,5-dimethyl-4-methoxyphenyl)-5-methylindenyl]zirconium dichloride

(16-1) Synthesis of 4-(3,5-dimethyl-4-methoxyphenyl)-5-methylindene 3,5-Dimethyl-4-methoxyphenylboronic acid (10 g, 55.5 mmol) was dissolved in dimethoxyethane (200 mL), and aqueous solution of cesium carbonate (24.1 g, 74 mmol), 4-bromo-5-methylindene (7.7 g, 37 mmol), tetrakis(triphenylphosphine)palladium (1.7 g) were sequentially added. Solution was reacted for 24 hours while heating under reflux, then, reaction solution was poured into 1N hydrochloric acid-ice water, after stirring, was extracted with diethyl ether. Organic layer was washed saturated solution of sodium chloride, and dried over magnesium sulfate, then, solvent was distilled off to obtain the crude product.

This was purified by silica-gel column chromatography to obtain the desired 4-(3,5-dimethyl-4-methoxyphenyl)-5-methylindene (8.2 g, yield: 84%).

(16-2) Synthesis of 2-bromo-4-(3,5-dimethyl-4-methoxyphenyl)-5-methylindene The obtained 4-(3,5-dimethyl-4-methoxyphenyl)-5-methylindene (8.2 g, 31.0 mmol) was dissolved in dimethylsulfoxide (100 mL), and water (2 mL) was added. N-Bromosuccinimide (7.2 g, 40.4 mmol) was added at 0° C., and reaction solution was stirred for 2 hours at room temperature, and quenched by adding water on ice bath, and organic layer was extracted by adding toluene. p-Toluenesulfonic acid monohydrate (0.7 g, 3.7 mmol) was added to organic layer. Solution was reacted for 2 hours while heating under reflux, then, water was added to the reaction solution to separate organic layer. Organic layer was washed with saturated solution of sodium chloride, and dried over magnesium sulfate, then, solvent was distilled off under reduced pressure to obtain the crude product.

This was purified by silica-gel column chromatography to obtain 2-bromo-4-(3,5-dimethyl-4-methoxyphenyl)-5-methylindene (7.8 g, yield: 72%).

(16-3) Synthesis of 2-{2-(5-methylfuryl)}-4-(3,5-dimethyl-4-methoxyphenyl)-5-methylindene 2-Methylfuran (3.9 g, 47.5 mmol) was dissolved in dimethoxyethane (50 mL), and solution of n-butyllithium in n-hexane (1.66 M, 28.6 mL) was dropped at −76° C. Reaction solution was stirred for 3 hours at −30° C., then, triisopropyl borate (12 mL, 52 mmol) was dropped, and reaction solution was stirred for 16 hours at room temperature. Water was added, and reaction solution was stirred for 1 hour. Then, aqueous solution (70 mL) of sodium carbonate (4.8 g, 45.3 mmol), solution of 2-bromo-4-(3,5-dimethyl-4-methoxyphenyl)-5-methylindene (7.8 g, 22.5 mmol) dissolved in dimethoxyethane (40 mL), tetrakis(triphenylphosphine)palladium (0.65 g) were sequentially added, and solution was reacted for 2 hours while heating under reflux. Water was added to the reaction solution to separate organic layer, and organic layer was washed with saturated solution of sodium chloride, and dried over magnesium sulfate, then, solvent was distilled off under reduced pressure.

The obtained crude product was purified by silica-gel column chromatography to obtain the desired 2-{2-(5-methylfuryl)}-4-(3,5-dimethyl-4-methoxyphenyl)-5-methylindene (6.1 g, yield: 78%).

(16-4) Synthesis of dimethylbis[2-(2-(5-methylfuryl))-4-(3,5-dimethyl-4-methoxyphenyl)-5-methylindenyl]silane The obtained 2-{2-(5-methylfuryl)}-4-(3,5-dimethyl-4-methoxyphenyl)-5-methylindene (3.5 g, 10.2 mmol) was dissolved in tetrahydrofuran (60 mL), and solution of n-butyllithium in n-hexane (1.66 M, 6.1 mL) was dropped at −76° C. After elevating temperature up to room temperature, reaction solution was stirred for hours, then, N-methylimidazole (0.02 mL) was added, dichlorodimethylsilane (0.6 mL, 5.1 mmol) was dropped at −76° C. Reaction solution was stirred for 1.5 hours at room temperature, and water was added to separate organic layer. Organic layer was washed with saturated solution of sodium chloride, and dried over magnesium sulfate, then, solvent was distilled off under reduced pressure to obtain the crude product.

This was purified by silica-gel column chromatography to obtain the desired dimethylbis[2-{2-(5-methylfuryl)}-4-(3,5-dimethyl-4-methoxyphenyl)-5-methylindenyl]silane (3.2 g, yield: 85%).

(16-5) Synthesis of dimethylsilylenebis[2-{2-(5-methylfuryl)}-4-(3,5-dimethyl-4-methoxyphenyl)-5-methylindenyl]zirconium dichloride The obtained dimethylbis[2-{2-(5-methylfuryl)}-4-(3,5-dimethyl-4-methoxyphenyl)-5-methylindenyl]silane (3.2 g, 4.3 mmol) was dissolved in diethyl ether (120 mL), and solution of n-butyllithium in n-hexane (1.66 M, 5.2 mL) was dropped at −76° C. Reaction solution was stirred for 2 hours at room temperature, then, solvent was distilled off under reduced pressure. Diethyl ether (6 mL), toluene (120 mL) were sequentially added, and reaction solution was cooled at −50° C., zirconium tetrachloride (1.0 g, 4.3 mmol) was added. After elevating temperature up to room temperature immediately, reaction solution was stirred for 2 hours. The obtained reaction solution was once concentrated, and extracted with toluene, and concentrated again to dryness. Re-crystallization was carried out with toluene-hexane, and the obtained solid was sequentially washed with hexane, diisopropyl ether, and reaction solution was extracted with toluene again.

Further, solid was sequentially washed with hexane, diethyl ether to obtain racemic form (0.78 g) of the desired dimethylsilylenebis[2-{2-(5-methylfuryl)}-4-(3,5-dimethyl-4-methoxyphenyl)-5-methylindenyl]zirconium dichloride.

$^1$H-NMR (400 MHz, CDCl$_3$, rac isomer).1.05 (s, 6H, Si(CH$_3$)$_2$), 2.26 (s, 6H, tol-CH$_3$), 2.29 (s, 6H, Furyl-CH$_3$), 2.32 (s, 6H, tol-CH$_3$), 2.39 (s, 6H, Indenyl-5-CH$_3$), 3.74 (s, 6H, —OMe), 6.04 (d, 2H, Furyl-H), 6.21 (d, 2H, Furyl-H), 6.59 (s, 2H, Cp-H), 6.64 (d, 2H, Indenyl-H), 6.74 (d, 2H, Indenyl-H), 6.80 (s, 2H, Ph-H), 7.39 (s, 2H, Ph-H).

(16-6) Preparation of Catalyst Using Metallocene complex P (catalyst P)

Catalyst P was obtained by the same operation as the preparation of catalyst described in [Example 3](3-6) except that 75 μmol of metallocene complex P instead of metallocene complex C was used.

Magnification ratio of pre-polymerization in this case (value of amount of pre-polymerized polymer divided by the amount of solid catalyst) was 0.38.

(16-7) Propylene-propylene•ethylene Block Copolymerization by Catalyst P 100 mg of catalyst P was used instead of catalyst A, and the operation similar to [Example 1](1-8) was carried out. The average gas molar composition in reactor became propylene/ethylene=50/50 when polymerizing propylene/ethylene in the second step. As a result, 139 g of propylene-propylene•ethylene block copolymer was obtained.

From the result of CFC-IR, block copolymer obtained in the above had 26% by weight of rubber content (CP content), 42 mol % of ethylene content in rubber (CP), and 330,000 of weight average molecular weight in CP (Mw). In addition, rubber polymerization activity (CP activity) was 730 (g-CP/g-Cat/hr). Tm of the other collected propylene homo-polymer was 158° C.

Example 17

Metallocene Complex Q

Synthesis of dimethylsilylenebis[2-{2-(5-methylfuryl)}-4-(4-chloro-3,5-dimethylphenyl)-5-methylindenyl]zirconium dichloride (17-1) Synthesis of 5-bromo-2-chloro-1,3-dimethylbenzene 4-Bromo-2,6-dimethylaniline (20 g, 0.1 mol) was dispersed in 7N hydrochloric acid (50 mL), and reaction solution was cooled down to 0° C., aqueous solution (50 mL) of sodium nitrite (7.6 g, 0.11 mol) was added, and reaction solution was stirred for 20 minutes, then, dispersion solution (100 mL) of cuprous chloride (11 g, 0.11 mol) in 7N hydrochloric acid was added little by little. Then, reaction solution was stirred while heating at 70° C., subsequently, was stirred for 16 hours at room temperature. Reaction solution was poured into ice-water, and extracted with diethyl ether after stirring. Organic layer was washed with aqueous solution of 1N sodium hydroxide and saturated solution of sodium chloride, and dried over magnesium sulfate, then, solvent was distilled off under reduced pressure to obtain the crude product.

This was purified by silica-gel column chromatography to obtain the desired 5-bromo-2-chloro-1,3-dimethylbenzene (16.7 g, yield: 76%).

(17-2) Synthesis of 4-(4-chloro-3,5-dimethylphenyl)-5-methylindene

5-Bromo-2-chloro-1,3-dimethylbenzene (6.7 g, 30.5 mmol) was dissolved in diethyl ether (100 mL), and cooled at 0° C., and solution of n-butyllithium in n-hexane (1.65 M, 18.5 mL) was dropped, and solution was stirred for 2 hours at room temperature. Reaction solution was cooled at −72° C. again, and triisopropyl borate (7.7 mL, 33 mmol) was dropped, and reaction solution was stirred for 16 hours at room temperature. Water (5 mL) was added, then, reaction solution was stirred for 1 hour, and extracted with diethyl ether. Organic layer was washed with saturated solution of sodium chloride, and dried over magnesium sulfate, then, solvent was distilled off under reduced pressure. The obtained white solid (2 g) was dissolved in dimethoxyethane (50 mL), and aqueous solution (50 mL) of cesium carbonate (5.0 g, 15 mmol), 4-bromo-5-methylindene (1.6 g, 7.6 mmol), tetrakis(triphenylphosphine)palladium (0.2 g) were sequentially added. Solution was reacted for 6 hours while heating under reflux, then, reaction solution was poured into 1N hydrochloric acid-ice water, and extracted with diethyl ether after stirring. Organic layer was washed with saturated solution of sodium chloride, and dried over magnesium sulfate, then, solvent was distilled off under reduced pressure to obtain the crude product.

This was purified with silica-gel column chromatography to obtain the desired 4-(4-chloro-3,5-dimethylphenyl)-5-methylindene (1.8 g, yield: 88%).

(17-3) Synthesis of 2-bromo-4-(4-chloro-3,5-dimethylphenyl)-5-methylindene

The obtained 4-(4-chloro-3,5-dimethylphenyl)-5-methylindene (2.5 g, 9.3 mmol) was dissolved in dimethylsulfoxide (50 mL), and water (2 mL) was added. N-Bromosuccinimide (2.1 g, 11.8 mmol) was added at 0° C., and reaction solution was stirred for 2 hours at room temperature. Reaction solution was quenched by adding water on ice bath, and organic layer was extracted by adding toluene. p-Toluenesulfonic acid monohydrate (0.5 g) was added to organic layer. Solution was reacted for 1 hour while heating under reflux, then, water was added to the reaction solution to separate organic layer. Organic layer was washed with saturated solution of sodium chloride, and dried over magnesium sulfate, then, solvent was distilled off under reduced pressure to obtain the crude product.

This was purified by silica-gel column chromatography to obtain 2-bromo-4-(4-chloro-3,5-dimethylphenyl)-5-methylindene (2.8 g, yield: 87%).

(17-4) Synthesis of 2-{2-(5-methylfuryl)}-4-(4-chloro-3,5-dimethylphenyl)-5-methylindene 2-Methylfuran (1.4 g, 17.0 mmol) was dissolved in dimethoxyethane (10 mL), and solution of n-butyllithium in n-hexane (1.65 M, 10.3 mL) was dropped at −76° C. Reaction solution was stirred for 2 hours, then, temperature was elevated up to −30° C., and triisopropyl borate (12 mL, 52 mmol) was dropped, and reaction solution was stirred for 16 hours at room temperature. Water (10 mL) was added, and reaction solution was stirred for 1 hour. Then, aqueous solution (30 mL) of sodium carbonate (1.7 g, 16 mmol), solution of 2-bromo-4-(4-chloro-3,5-dimethylphenyl)-5-methylindene (2.5 g, 8.0 mmol) dissolved in dimethoxyethane (20 mL), tetrakis(triphenylphosphine)palladium (0.2 g) were sequentially added, solution was reacted for 3 hours while heating under reflux. Water was added to the reaction solution to separate organic layer, and organic layer was washed with saturated solution of sodium chloride, and dried over magnesium sulfate, then, solvent was distilled off under reduced pressure.

The obtained crude product was purified by silica-gel column chromatography to obtain the desired 2-{2-(5-methylfuryl)}-4-(4-chloro-3,5-dimethylphenyl)-5-methylindene (1.2 g, yield: 43%).

(17-5) Synthesis of dimethylbis[2-{2-(5-methylfuryl)}-4-(4-chloro-3,5-dimethylphenyl)-5-methylindenyl]silane The obtained 2-[2-(5-methylfuryl)]-4-(4-chloro-3,5-dimethylphenyl)-5-methylindene (2.9 g, 8.3 mmol) was dissolved in tetrahydrofuran (40 mL), and solution of n-butyllithium in n-hexane (1.65 M, 5.0 mL) was dropped at $-76°$ C. After elevating temperature up to room temperature, reaction solution was stirred for 3 hours, then, N-methylimidazole (0.02 mL) was added, dichlorodimethylsilane (0.5 mL, 4.1 mmol) was dropped at $-76°$ C. Reaction solution was stirred for 2 hours at room temperature, and water was added to separate organic layer. Organic layer was washed with saturated solution of sodium chloride, and dried over magnesium sulfate, then, solvent was distilled off under reduced pressure to obtain the crude product.

This was purified by silica-gel column chromatography to obtain the desired dimethylbis[2-{2-(5-methylfuryl)}-4-(4-chloro-3,5-dimethylphenyl)-5-methylindenyl]silane (2.0 g, yield: 64%).

(17-6) Synthesis of dimethylsilylenebis[2-{2-(5-methylfuryl)}-4-(4-chloro-3,5-dimethylphenyl)-5-methylindenyl]zirconium dichloride The obtained dimethylbis[2-{2-(5-methylfuryl)}-4-(4-chloro-3,5-dimethylphenyl)-5-methylindenyl]silane (2.0 g, 2.6 mmol) was dissolved in diethyl ether (100 mL), and solution of n-butyllithium in n-hexane (1.65 M, 3.2 mL) was dropped at $-76°$ C. Reaction solution was stirred for 2 hours at room temperature, then, solvent was distilled off under reduced pressure. Diethyl ether (5 mL), toluene (100 mL) were sequentially added, and reaction solution was cooled at $-50°$ C., and zirconium tetrachloride (0.6 g, 2.6 mmol) was added. After elevation up to room temperature immediately, reaction solution was stirred for 2 hours. The obtained reaction solution was once concentrated, then, and extracted with toluene, and concentrated again to dryness.

Hexane extraction was repeatedly carried out from this solution to remove the impurities having low solubility little by little, then, reaction solution was cooled to re-crystallize, and the desired compound, racemic form (0.5 g) of dimethylsilylenebis[2-{2-(5-methylfuryl)}-4-(4-chloro-3,5-dimethylphenyl)-5-methylindenyl]zirconium dichloride was obtained.

$^1$H-NMR (400 MHz, CDCl$_3$) 1.07 (s, 6H, Si(CH$_3$)$_2$), 2.26 (s, 6H, Furyl-CH$_3$), 2.35 (s, 6H, tol-CH$_3$), 2.40 (s, 6H, Indenyl-5-CH$_3$), 2.41 (s, 6H, tol-CH$_3$), 6.04 (dd, 2H, Furyl-H), 6.21 (d, 2H, Furyl-H), 6.53 (s, 2H, Cp-H), 6.64 (d, 2H, Indenyl-H), 6.75 (d, 2H, Indenyl-H), 6.87 (s, 2H, Ph-H), 7.45 (s, 2H, Ph-H).

(17-7) Preparation of Catalyst Using Metallocene Complex Q (Catalyst Q)

Catalyst Q was obtained by the same operation as the preparation of catalyst described in [Example 3](3-6) except that 75 µmol of metallocene complex Q instead of metallocene complex C was used.

Magnification ratio of pre-polymerization in this case (value of amount of pre-polymerized polymer divided by the amount of solid catalyst) was 1.47.

(17-8) Propylene-propylene•ethylene Block Copolymerization by Catalyst Q 260 mg of catalyst Q was used instead of catalyst A, and the operation similar to [Example 1](1-8) was carried out. The average gas molar composition in reactor became propylene/ethylene=51/49 when polymerizing propylene/ethylene in the second step. As a result, 175 g of propylene-propylene•ethylene block copolymer was obtained.

From the result of CFC-IR, block copolymer obtained in the above had 13% by weight of rubber content (CP content), 35 mol % of ethylene content in rubber (CP), and 500,000 of weight average molecular weight in CP (Mw). In addition, rubber polymerization activity (CP activity) was 900 (g-CP/g-Cat/hr). Tm of the other collected propylene homo-polymer was 156° C.

Comparative Example 1

Metallocene Complex R

Synthesis of dimethylsilylenebis(2-(2-(5-methylfuryl))-4-phenyl-indenyl)zirconium dichloride Comparative Example 1-1

Synthesis of Metallocene Complex R

Metallocene complex R was synthesized according to the method described in example 1 of JP-A-2002-128832 to obtain the racemic form (purity: 99% or more).

Comparative Example 1-2

Preparation of Catalyst Using Metallocene Complex R (Catalyst R)

Catalyst R was obtained by the same operation as the preparation of catalyst described in [Example 1](1-7) except that 223 mg (293 μmol) of metallocene complex R instead of metallocene complex A was used.

Magnification ratio of pre-polymerization in this case (value of amount of pre-polymerized polymer divided by the amount of solid catalyst) was 1.80.

Comparative Example 1-3

Propylene-propylene•ethylene Block Copolymerization by Catalyst R 30 mg of catalyst R was used instead of catalyst A, the operation similar to [Example 1](1-8) was carried out. The average gas molar composition in reactor became propylene/ethylene=43/57 when polymerizing propylene/ethylene in the second step. As a result, 173 g of propylene-propylene•ethylene block copolymer was obtained.

From the result of CFC-IR, block copolymer obtained in the above had 9% by weight of rubber content (CP content), 51 mol % of ethylene content in rubber (CP), and 121,000 of weight average molecular weight in CP (Mw). In addition, rubber polymerization activity (CP activity) was 1,200 (g-CP/g-Cat/hr). Tm of the other collected propylene homo-polymer was 154° C., MFR was 162 (dg/min).

Comparative Example 2

Metallocene Complex S

Synthesis of dimethylsilylene(2-methyl-4-(4-t-butylphenyl)indenyl)(2-i-propyl-4-(4-t-butylphenyl)indenyl)zirconium dichloride Comparative Example 2-1

Synthesis of Metallocene Complex S

Metallocene complex S was synthesized with reference to the method according to JP-A-2003-533550 to obtain the racemic form (purity: 99% or more).

Comparative Example 2-2

Preparation of Catalyst Using Metallocene Complex S (Catalyst S)

Catalyst S was obtained by the same operation as the preparation of catalyst described in [Example 1](1-7) except that 244 mg (322 μmol) of metallocene complex S instead of metallocene complex A was used.

Magnification ratio of pre-polymerization in this case (value of amount of pre-polymerized polymer divided by the amount of solid catalyst) was 1.88.

Comparative Example 2-3

Propylene-propylene•ethylene Block Copolymerization by Catalyst S 20 mg of catalyst S was used instead of catalyst A, and the operation similar to [Example 1](1-8) was carried out. The average gas molar composition in reactor became propylene/ethylene=36/64 when polymerizing propylene/ethylene in the second step. As a result, 435 g of propylene-propylene•ethylene block copolymer was obtained.

From the result of CFC-IR, block copolymer obtained in the above had 11% by weight of rubber content (CP content), 44 mol % of ethylene content in rubber (CP), and 182,000 of weight average molecular weight in CP (Mw), and ethylene content soluble at 100° C. was 0.6%. In addition, rubber polymerization activity (CP activity) was 2,900 (g-CP/g-Cat/hr). Tm of the other collected propylene homo-polymer was 155° C., MFR was 138 (dg/min).

Comparative Example 3

Metallocene Complex T

Synthesis of dimethylsilylenebis(2-methyl-4-phenyl-indenyl)zirconium dichloride

Comparative Example 3-1

Synthesis of Metallocene Complex T

Metallocene complex T was synthesized with reference to the method according to Organometallics 1994, 13, 954-963 to obtain racemic form (purity: 99% or more)

Comparative Example 3-2

Preparation of Catalyst Using Metallocene Complex T (Catalyst T)

Catalyst T was obtained by the same operation as the preparation of catalyst described in [Example 1](1-7) except that 244 mg (322 μmol) of metallocene complex T instead of metallocene complex A was used.

Magnification ratio of pre-polymerization in this case (value of amount of pre-polymerized polymer divided by the amount of solid catalyst) was 2.11.

Comparative Example 3-3

Propylene-propylene•ethylene Block Copolymerization by Catalyst T

The operation similar to [Example 1](1-8) was carried out except that 20 mg of catalyst T was used instead of catalyst A and the average gas molar composition in reactor was adjusted so as to be propylene/ethylene=33/66 when polymerizing propylene/ethylene in the second step.

As a result, 136 g of propylene-propylene•ethylene block copolymer was obtained.

From the result of CFC-IR, block copolymer obtained in the above had 61% by weight of rubber content (CP content), 49 mol % of ethylene content in rubber (CP), and 63,000 of weight average molecular weight in CP (Mw). In addition, rubber polymerization activity (CP activity) was 10,200 (g-CP/g-Cat/hr). Tm of the other collected propylene homo-polymer was 149° C., MFR was 2 (dg/min).

TABLE 1

| Example No | Catalyst No | Ethylene content in gas at CP polymerization | Ethylene content in CP | CP polymerization activity (g-CP/g-cat · hr) | Molecular weight (Mw) | MP of propylene homo-polymer |
|---|---|---|---|---|---|---|
| 1 | A | 46 | 34 | 340 | 508,000 | 156 |
| 2-(1) | B | 46 | 32 | 500 | 507,000 | 156 |
| 2-(2) | B | 47 | 28 | 6,700 | 483,000 | 156 |
| 2-(3) | B | 68 | 51 | 1,600 | 778,000 | 156 |
| 3 | C | 55 | 38 | 320 | 430,000 | 155 |
| 4 | D | 50 | 50 | 117 | 476,000 | 149 |
| 5 | E | 52 | 34 | 2,200 | 300,000 | 153 |
| 6 | F | 48 | 37 | 1,200 | 607,000 | 157 |
| 7 | G | 49 | 34 | 600 | 520,000 | 154 |
| 8 | H | 49 | 33 | 250 | 540,000 | 153 |
| 9 | I | 53 | 36 | 1,000 | 600,000 | 150 |
| 10 | J | 54 | 30 | 670 | 420,000 | 152 |
| 11 | K | 51 | 44 | 55 | 408,000 | 157 |
| 12 | L | 55 | 39 | 2,700 | 350,000 | 155 |
| 13 | M | 47 | 39 | 4,400 | 220,000 | 155 |
| 14 | N | 50 | 46 | 260 | 240,000 | 154 |
| 15 | O | 50 | 44 | 800 | 230,000 | 154 |
| 16 | P | 50 | 42 | 730 | 330,000 | 158 |
| 17 | Q | 49 | 35 | 900 | 500,000 | 156 |
| Comp. Exp 1 | R | 57 | 51 | 1200 | 121,000 | 154 |
| Comp. Exp 2 | S | 64 | 44 | 2900 | 182,000 | 155 |
| Comp. Exp 3 | T | 66 | 49 | 10,200 | 63,000 | 149 | metallocene complex (A): dimethylsilylenebis(2-(2-(5-methylfuryl))-4-phenyl-5-methylindenyl)zirconium dichloride;

metallocene complex (B): dimethylsilylenebis(2-(2-(5-methylfuryl))-4-(4-t-butylphenyl)-5-ethylindenyl)zirconium dichloride;

metallocene complex (C): dimethylsilylenebis(2-(2-(5-methylfuryl))-4-(3-t-butylphenyl)-5-methylindenyl)zirconium dichloride;

metallocene complex (D): dimethylsilylenebis(2-(2-(5-methylfuryl))-4-(2-methylphenyl)-5-methylindenyl)zirconium dichloride;

metallocene complex (E): dimethylsilylenebis(2-(2-(5-methylfuryl))-4-(2,5-dimethylphenyl)-5-methylindenyl)zirconium dichloride;

metallocene complex (F): dimethylsilylenebis(2-(2-(5-methylfuryl))-4-(3,5-dimethylphenyl)-5-methylindenyl)zirconium dichloride;

metallocene complex (G): dimethylsilylenebis(2-(2-(5-methylfuryl))-4-(3,5-diisopropylphenyl)-5-methylindenyl)zirconium dichloride;

metallocene complex (H): dimethylsilylenebis[2-{2-(5-methylfuryl)}-4-(3,5-di-t-butylphenyl)-5-methylindenyl]zirconium dichloride;

metallocene complex (I): dimethylsilylenebis[2-{2-(5-methylfuryl)}-4-[2-methyl-4-(t-butyl)phenyl]-5-methylindenyl]zirconium dichloride;

metallocene complex (J): dimethylsilylenebis[2-{2-(5-methylfuryl)}-4-(1-naphthyl)-5-methylindenyl]zirconium dichloride;

metallocene complex (K): dimethylsilylenebis(2-(2-(5-methylfuryl))-4-(2-naphthyl)-5-methylindenyl)zirconium dichloride;

metallocene complex (L): dimethylsilylenebis(2-(5-methyl-2-furyl)-4-(4-biphenylyl)-5-methyl-indenyl)zirconium dichloride;

metallocene complex (M): dimethylsilylenebis(2-(2-(5-methylfuryl))-4-(4-methoxyphenyl)-5-methylindenyl)zirconium dichloride;

metallocene complex (N): dimethylsilylenebis[2-{(2-(5-methylfuryl)}-4-(4-trifluoromethylphenyl)-5-methylindenyl]zirconium dichloride;

metallocene complex (O): dimethylsilylenebis[2-{2-(5-methylfuryl)}-4-(3,5-dimethoxyphenyl)-5-methylindenyl]zirconium dichloride;

metallocene complex (P): dimethylsilylenebis[2-{2-(5-methylfuryl)}-4-(3,5-dimethyl-4-methoxyphenyl)-5-methylindenyl]zirconium dichloride;

metallocene complex (Q): dimethylsilylenebis[2-[2-(5-methylfuryl)]-4-(4-chloro-3,5-dimethylphenyl)-5-methylindenyl]zirconium dichloride;

metallocene complex (R): dimethylsilylenebis(2-(2-(5-methylfuryl))-4-phenyl-indenyl)zirconium dichloride metallocene complex (S): dimethylsilylene(2-methyl-4-(4-t-butylphenyl)indenyl)(2-i-propyl-4-(4-t-butylphenyl)indenyl)zirconium dichloride;

metallocene complex (T): dimethylsilylenebis(2-methyl-4-phenylindenyl)zirconium dichloride;

INDUSTRIAL APPLICABILITY

By the metallocene complex of the present invention and the catalyst containing the same and the polymerization method of olefin, rubber component having high molecular weight can be produced, and propylene-propylene (ethylene or α-olefin) block copolymer having high content of ethylene or α-olefin can be efficiently produced. In addition, rubber component can be produced with high-activity, therefore, the present invention is significantly useful.

The invention claimed is:
1. A metallocene complex represented by the following general formula [I]:

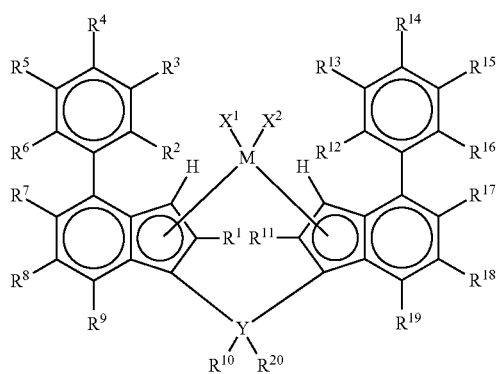

[I]

wherein M is Ti, Zr or Hf, Y is a carbon, a silicon or a germanium, $X^1$ and $X^2$ are each independently a ligand forming σ-bond with M, $R^1$ and $R^{11}$ may be each other same or different, and are hydrogen, alkyl group having 1 to 6 carbon number, alkoxy group having 1 to 6 carbon number, furyl group, thienyl group, furyl group having substituent, or thienyl group having substituent, and one or both of $R^1$ and $R^{11}$ are any of furyl group, thienyl group, furyl group having substituent, or thienyl group having substituent, $R^7$ and $R^{17}$ may be the same or different, and are hydrogen, halogen atom, alkyl group having 1 to 6 carbon number, alkoxy group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number or halogen-containing aryl group having 6 to 18 carbon number, wherein when any one of $R^7$ and $R^{17}$ is hydrogen, the other group is a substituent group except hydrogen, $R^2$, $R^3$, $R^4$, $R^5$, $R^6$, $R^8$, $R^9$, $R^{12}$, $R^{13}$, $R^{14}$, $R^{15}$, $R^{16}$, $R^{18}$ and $R^{19}$ may be same or different, and are hydrogen, halogen atom, alkyl group having 1 to 6 carbon number, alkoxy group having 1 to 6 carbon number, alkenyl group having 1 to 6 carbon number, halogen-containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen-containing aryl group having 6 to 18 carbon number, or heterocyclic group constituting 5-membered ring or 6-membered ring which may have substituent, in addition, 6 to 7-membered ring may be formed together with both of the adjacently located R and 6 to 7-membered ring may have unsaturated bond, $R^{10}$ and $R^{20}$ may be same or different, and are hydrogen, alkyl group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number, halogen-containing aryl group having 6 to 18 carbon number, or heterocyclic group forming 5-membered ring or 6-membered ring which may have substituent, 4 to 7-membered ring may be formed together with $R^{10}$ and $R^{20}$.

2. The metallocene complex according to claim 1, wherein in formula[I], $R^1$ and $R^{11}$ may be the same or different, and are hydrogen, alkyl group having 1 to 6 carbon number, alkoxy group having 1 to 6 carbon number or substituent represented by formula[II], and one or both of $R^1$ and $R^{11}$ are the substituent represented by formula[II]:

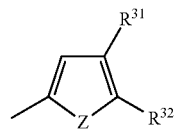

[II]

wherein Z is oxygen atom or sulfur atom, $R^{31}$ and $R^{32}$ may be same or different, and are hydrogen, halogen atom, alkyl group having 1 to 6 carbon number, alkoxy group having 1 to 6 carbon number, alkenyl group having 1 to 6 carbon number, halogen containing alkyl group having 1 to 6 carbon number, alkyl group having 1 to 6 carbon number containing trialkylsilyl group, silyl group containing hydrocarbon group having 1 to 6 carbon number, aryl group having 6 to 18 carbon number or halogen-containing aryl group having 6 to 18 carbon number, and $R^{31}$ and $R^{32}$ may form 6-membered ring, and 6-membered ring may comprise unsaturated bond.

3. The metallocene complex according to claim 2, wherein in the above-described general formula[I], $R^1$ and $R^{11}$ may be same or different, and are substituents represented by formula [II].

4. The metallocene complex according to claim 2, wherein in the above-described general formula [I], $R^7$ and $R^{17}$ may be same or different, and are alkyl group having 1 to 6 carbon number.

5. The metallocene complex according to claim 4, wherein in the above-described general formula [I], $R^7$ and $R^{17}$ are methyl groups.

6. The metallocene complex according to claim 4, wherein in the above-described general formula [I], $R^2$, $R^3$, $R^4$, $R^5$, $R^6$, $R^8$, $R^9$, $R^{12}$, $R^{13}$, $R^{14}$, $R^{15}$, $R^{16}$, $R^{18}$ and $R^{19}$ may be each other same or different, and are hydrogen, halogen atom, alkyl group having 1 to 6 carbon number, alkoxy group having 1 to 6 carbon number, aryl group having 6 to 18 carbon number, or halogen-containing aryl group having 6 to 18 carbon number, in addition, 6 to 7-membered ring may be formed together with the adjacently located R, and 6 to 7-membered ring may comprise unsaturated bond.

7. The metallocene complex according to claim 6, wherein in the above-described general formula [I], $R^8$, $R^9$, $R^{18}$ and $R^{19}$ are hydrogen.

8. The metallocene complex according to claim 6, wherein in the above-described general formula [I], $R^2$, $R^8$, $R^9$, $R^{12}$, $R^{18}$ and $R^{19}$ are hydrogen.

9. A catalyst for olefin polymerization comprising a metallocene complex according to claim 1.

10. A catalyst for olefin polymerization, in comprising (A), (B) and (C): wherein
component (A) is a metallocene complex according to claim 1;
component (B) is a compound to form ionic pair by reacting with component (A) or ion-exchanging layered silicate, and
component (C) is an organic aluminum compound.

11. The catalyst for olefin polymerization according to claim 10, wherein component (B) is ion-exchanging layered silicate.

12. The catalyst for olefin polymerization according to claim 9, wherein pre-polymerization is carried out when producing the catalyst.

13. A olefin polymerization method wherein olefin polymerization or copolymerization is carried out in the presence of the catalyst for olefin polymerization according to claim 9.

14. A multi-step polymerization method comprises (i) polymerizing 90 to 100% by weight of propylene, 10% by weight or less of ethylene and/or α-olefin having 4 or more carbon number relative to total monomer component; and (ii) polymerizing 10 to 90% by weight of propylene, 10 to 90% by weight of ethylene and/or α-olefin having 4 or more carbon number relative to total monomer component;

wherein at least one of (i) and (ii) are conducted in the presence of a catalyst for olefin polymerization according to claim 9.

15. A two-step polymerization method according to claim 14, wherein (i) comprises a bulk polymerization wherein propylene is the solvent or gas-phase polymerization maintaining the monomers as gas state in which 90 to 100% by weight of propylene, 10% by weight or less of ethylene and/or α-olefin having 4 or more carbon number relative to total monomer component; and (ii) comprises a gas-phase polymerization in which 10 to 90% by weight of propylene, 10 to 90% by weight of ethylene and/or α-olefin having 4 or more carbon number relative to total monomer component are carried out.

16. The two-step polymerization method according to claim 15, wherein 100% by weight of propylene is present relative to the total monomer component in (i).

* * * * *